United States Patent [19]
Yanaka et al.

[11] Patent Number: 5,739,131
[45] Date of Patent: Apr. 14, 1998

[54] BENZENE DERIVATIVES AND PHARMACEUTICAL COMPOSITION

[75] Inventors: Mikiro Yanaka, Matsudo; Fuyuhiko Nishijima, Tokyo; Hiroyuki Enari, Tokyo; Toshikazu Dewa, Tokyo; Toru Yamazaki, Tokyo; Michihito Ise, Kawagoe, all of Japan

[73] Assignee: Kureha Chemical Industry Co., Ltd., Tokyo, Japan

[21] Appl. No.: 841,621

[22] Filed: Apr. 30, 1997

Related U.S. Application Data

[62] Division of Ser. No. 457,147, Jun. 1, 1995, Pat. No. 5,696,118.

[30] Foreign Application Priority Data

Jun. 1, 1994 [JP] Japan ................... 6-142276

[51] Int. Cl.$^6$ ................... A61K 31/535; C07D 295/192
[52] U.S. Cl. ................... 514/237.5; 544/58.4; 544/132; 544/165; 544/391; 546/226; 548/253; 548/539; 548/953; 560/48; 562/457
[58] Field of Search ................... 544/165; 514/237.5

[56] References Cited

U.S. PATENT DOCUMENTS 3,829,487  8/1974  Mrozik.

FOREIGN PATENT DOCUMENTS

| 0138720 | 4/1984 | European Pat. Off. |
| 0185368 | 6/1986 | European Pat. Off. |
| 0425921 | 5/1991 | European Pat. Off. |
| 1479207 | 5/1967 | France. |
| 874443 | 3/1953 | Germany. |
| 2733156 | 2/1978 | Germany. |
| 205901 | 1/1994 | Germany. |
| 302372 | 10/1954 | Switzerland. |

OTHER PUBLICATIONS

Kubo et al., "Nonpeptide Angiotensin II Receptor Antagonists. Synethesis and Biological Activity of Benzimidazoles", *J. Med. Chem.*, 36:1772–1784, 1993.

Cambanis et al., "Potential Anticancer Agents. V. New Aromatic Nitrogen Mustards Related to 3–[N, N–Bis(2–chloroethyl)amino]–4–methylbenzoic Acid", *J. Med. Chem.*, 12(1):161–164, 1969.

Radek et al., "Contrast Media. V. Iodinated Metanilic Acid Derivative", *Chem. Abstracts*, 70:299, Abstract No. 114759e, 1969.

Kondo et al., "Preparation of Antibacterial Rifamycin Derivatives", *Chem. Abstracts*, 109:704, Abstract No. 14229h, 1988.

*Primary Examiner*—Robert W. Ramsuer
*Attorney, Agent, or Firm*—Sughrue, Mion, Zinn, Macpeak & Seas, PLLC

[57] ABSTRACT

A benzene derivative of the formula (I):

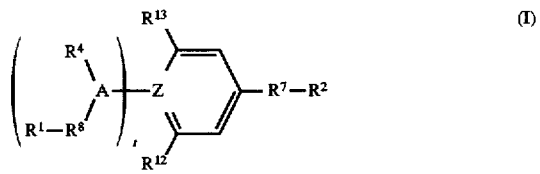

wherein $R^1$ is hydrogen, $C_{1-6}$-alkyl, $C_{1-6}$-haloalkyl, $-NH_2$, $-NHR^{21}$; $R^2$ is hydroxyl, $-OR^{22}$, three- to seven-membered saturated cycloaliphatic amino optionally interrupted by one or more nitrogen, oxygen or sulfur atoms, $-NHR^{23}$, $-N(R^{24})_2$, $-NH_2$; $R^4$ is hydrogen, $C_{1-6}$-alkyl, or $-C(=O)R^{25}$; $R^7$ is $-CO-$, $-SO_2-$; $R^8$ is $-CO-$, single bond; $R^{12}$ is $-R^{11}-R^5$; $R^{11}$ is $-N(R^5)-$, $-NH-$, $-O-$, $-N(R^{26})-$, $-N(C(=O)R^{27})-$, $-N(C(=O)NH_2)-$, $-N(C(=O)NHR^{28})-$; $R^{13}$ is hydrogen, $C_{1-6}$-alkyl, $C_{1-6}$-haloalkyl, $-NHC(=O)(CH_2)_mC_6H_5$, $-NHC(=O)R^{29}$, $-NHC(=O)CH(C_6H_5)_2$, $-NH_2$, $-NHR^{30}$, $-(CH_2)_nC_6H_5$; Z is C, CH, N; A is CH, N; $R^5$ is hydrogen, $-CH_2C_6H_4COOH$, $-CH_2C_6H_4COOR^{31}$, $-CH_2C_6H_4OH$, $-CH_2C_6H_4OR^{32}$, $-CH_2C_6H_4NH_2$, $-CH_2C_6H_4N(R^{33})_2$, $-CH_2C_6H_4$-azole, $-CH_2C_6H_4NHR^{34}$, $-CH_2C_6H_4C_6H_4R^{14}$; $R^{14}$ is azole, $-COOH$; $R^{21}$ to $R^{34}$ are independently $C_{1-6}$-alkyl or $C_{1-6}$-haloalkyl; m is 0 to 6; n is 0 to 6; t is 0 or 1, with the proviso that when Z is N, $R^5$ is hydrogen, $-CH_2C_6H_4COOH$, $-CH_2C_6H_4COOR^{31}$, $-CH_2C_6H_4OH$, $-CH_2C_6H_4OR^{32}$, $-CH_2C_6H_4NH_2$, $-CH_2C_6H_4N(R^{33})_2$, $-CH_2C_6H_4$-azole, or $-CH_2C_6H_4NHR^{34}$, or a salt thereof, and a pharmaceutical composition comprising said benzene derivative or a pharmaceutically acceptable salt thereof, and a pharmaceutically acceptable carrier are disclosed.

8 Claims, No Drawings

BENZENE DERIVATIVES AND PHARMACEUTICAL COMPOSITION

This is a division of U.S. Ser. No. 08/457,147, filed 1 Jun. 1995 now U.S. Pat. No. 5,696,118.

BACKGROUND OF THE INVENTION

1. Field of the Invention

The present invention relates to a novel benzene derivative or a salt thereof, and a pharmaceutical composition, particularly, an agent for treating a kidney disease, containing said benzene derivative or a pharmaceutically acceptable salt thereof. Although the benzene derivative of the present invention exhibits substantially no or very weak antagonism to the angiotensin II receptor subtype 1 which participates in action to depress blood pressure, it can sufficiently improve a kidney disease.

2. Description of the Related Art

Recently, there is an increasing tendency of patients suffering from renal dysfunction. The reason is believed that a development of drugs appropriate to treat kidney diseases is behind with an increasing aged population or changes in living environment. Therefore, the drugs appropriate to treat kidney diseases have been strongly desired.

More particularly, a method for treating lesions accompanying diseases, i.e., the nosotropic treatment, is mainly used as yet for kidney diseases, such as nephritis, diabetic nephropathy or renal failure. For example, an antihypertensive, diuretic or anti-inflammatory agent, or dietary treatment, kinesitherapy or the like is mainly used. Because kidney diseases are accompanied with hypertension and the hypertension is believed to be one of factors aggravating kidney diseases, the antihypertensive agents are often used. Of the antihypertensive agents, the agents to inhibit production or function of angiotensin II are attempted in many cases. This is because that angiotensin II is believed to be a factor aggravating kidney diseases due to its activities to raise blood pressure and accelerate growth of interstitial cells in the kidney, and elimination of such a factor as much as possible is believed to improve the kidney diseases.

It is reported in J. Clin. Pharmacol., 30:155–158, 1990 that when the antihypertensive agent (such as enalapril or captoril), namely, the agent to inhibit the enzyme to convert angiotensin I to angiotensin II which exhibits the activity to raise blood pressure (angiotensin converting enzyme; ACE), i.e., the angiotensin converting enzyme inhibitor (ACEI), is used, blood pressure is lowered and the progress of renal dysfunction is improved. U.S. Pat. No. 5,071,867 suggests that because the improvement of the renal dysfunction is observed in rats suffering therefrom by administering the antihypertensive agent in an amount larger than that usually used to lower blood pressure, human will become endurable to a large dose if the dose is carefully and gradually increased, and to thereby enjoy the benefit of curing the renal dysfunction in human. On the other hand, it is pointed out in "Saishin Igaku (Latest Medicine)", 48:1404–1409, 1993 that such agents have side effects such as dry-cough as their inherent properties, or are attended with danger to lower blood pressure and then cause acute renal failure, and therefore should be carefully administered.

Thereafter, an angiotensin II receptor antagonist (AGIIRA) was developed as a antihypertensive agent. Two kinds of the angiotensin II receptors, the subtype 1 and the subtype 2, are known at the present. Although the functions of the subtype 2 are not sufficiently elucidated, the subtype 1 is known to participate in blood pressure. Therefore, the subtype 1 receptor antagonist is a target of the development of the antihypertensive agent.

As the compounds which are antihypertensive agents exhibiting a strong antagonizing activity to the angiotensin II receptor, and at the same time, are examined for their action to kidney diseases, the imidazole derivative, 2-butyl-4-chloro-5-(hydroxymethyl)-1-[[2'-(1H-tetrazol-5-yl) biphenyl-4-yl]methyl]imidazole (Dup753 or MK954) is known. When the imidazole derivative was administered to renal dysfunction model rats, it was effective against proteinuria and glomerulosclerosis, but at the same time the reduction of blood pressure accompanied (J. Clinical Invest., 90:766–771, 1992). Further, when the above imidazole derivative was administered to hyperlipemia model rats, the kidney disease was improved in a lower dose without practical effect to blood pressure, but an evident reduction of blood pressure was observed at a large dose more effective against the kidney disease (Nephron, 65:426–432, 1993).

Further, compounds having the structures similar to that of the above imidazole derivative are disclosed in Japanese Unexamined Patent Publication No. 63-23868, and U.S. Pat. No. 5,153,197, U.S. Pat. No. 5,128,355 and U.S. Pat. No. 5,155,118. Japanese Unexamined Patent Publication No. 63-23868 discloses that such compounds are effective against hypertension and congestive heart failure. U.S. Pat. No. 5,153,197 discloses that such compounds are effective against hypertension. U.S. Pat. No. 5,128,355 discloses that such compounds are effective against heart failure. U.S. Pat. No. 5,155,118 discloses that such compounds are effective against renal failure caused by non-steroid anti-inflammatory agent. However, all the imidazole derivatives disclosed in said Japanese Unexamined Patent Publication and US Patents are characterized by a strong angiotensin II receptor antagonism, and have an activity to lower blood pressure.

EP 058829A2 and EP 0475206A2 disclose the compounds having a benzene skeleton and its application to kidney diseases. However, the benzene compounds are characterized by a strong angiotensin II receptor antagonism accompanied by the lowering function of blood pressure. Further, it is reported in J. Pharmacol. Experimental Therapeutics, 267:657–663, 1993 that when one of the benzene analogues, 2-[N-propyl-N-[[2'-(1H-tetrazol-5-yl) biphenyl-4-yl]methyl]amino]pyridine-3-carboxylic acid (A-81988), was administered to kidney disease model rats, proteinuria was improved, but at the same time, the reduction of blood pressure was observed. The above benzene analogues exhibits the function to lower blood pressure due to the strong angiotensin II receptor antagonism, and therefore, there is a fear of acute renal failure or the like when administered to the person suffering from kidney diseases.

As above, hitherto, drugs having the function to strongly lower blood pressure were basically desired in the treatment of the kidney diseases by the antihypertensive agent. In the kidney disease, the hypertension is an important symptom to be improved. However, mere lowering of blood pressure is not favorable. It is important to maintain appropriate blood pressure. Thus, it is necessary to adjust blood pressure by combining the kinds and the doses of the antihypertensive agents in view of the symptom. However, continuous treatment with a sufficient dose is desired for the kidney diseases per se. Therefore, so long as a conventional antihypertensive agent is used, it is fundamentally impossible to appropriately adjust blood pressure and at the same time to effectively cure the kidney disease by the sole antihypertensive agent. One of such problems is, for example, the above acute renal failure caused by the antihypertensive agent used.

SUMMARY OF THE INVENTION

The inventors of the present invention engaged in intensive studies to find the compounds having the properties which were completely unknown in the past, namely the compounds sufficiently effective in improvement of the renal dysfunction without any function to blood pressure, and as a result, found novel benzene derivatives which are sufficiently effective in improvement of the renal dysfunction while the antagonism thereof to the angiotensin II receptor subtype 1 is one-hundredth (1/100) to one-thousandth (1/1000) or less as large as that of the conventional antagonist having a standard activity as a antihypertensive agent. The present invention is based on the finding.

Accordingly, the present invention relates to a benzene derivative of the formula (I):

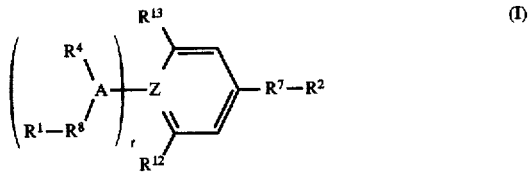

wherein $R^1$ is a hydrogen atom, alkyl of 1 to 6 carbon atoms, haloalkyl of 1 to 6 carbon atoms, $-NH_2$, or $-NHR^{21}$ group; $R^2$ is a hydroxyl, $-OR^{22}$, three- to seven-membered saturated cycloaliphatic amino group which may be interrupted by one or more nitrogen, oxygen or sulfur atoms, $-NHR^{23}$, $-N(R^{24})_2$, or $-NH_2$ group; $R^4$ is a hydrogen atom, alkyl of 1 to 6 carbon atoms, or $-C(=O)R^{25}$ group; $R^7$ is a $-CO-$ or $-SO_2-$; $R^8$ is a $-CO-$ or single bond; $R^{12}$ is $-R^{11}-R^5$; $R^{11}$ is $-N(R^5)-$, $-NH-$, $-O-$, $-N(R^{26})-$, $-N(C(=O)R^{27})-$, $-N(C(=O)NH_2)-$, or $-N(C(=O)NHR^{28})-$; $R^{13}$ is a hydrogen atom, alkyl of 1 to 6 carbon atoms, haloalkyl of 1 to 6 carbon atoms, $-NHC(=O)(CH_2)_mC_6H_5$, $-NHC(=O)R^{29}$, $-NHC(=O)CH(C_6H_5)_2$, $-NH_2$, $-NHR^{30}$, or $-(CH_2)_nC_6H_5$; Z is C, CH, or N; A is CH or N; $R^5$ is a hydrogen atom, $-CH_2C_6H_4COOH$, $-CH_2C_6H_4COOR^{31}$, $-CH_2C_6H_4OH$, $-CH_2C_6H_4OR^{32}$, $-CH_2C_6H_4NH_2$, $-CH_2C_6H_4N(R^{33})_2$, $-CH_2C_6H_4$-azole, $-CH_2C_6H_4NHR^{34}$, or $-CH_2C_6H_4C_6H_4R^{14}$ group; $R^{14}$ is an azole or $-COOH$ group; $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$ and $R^{34}$, are independently an alkyl of 1 to 6 carbon atoms or haloalkyl group of 1 to 6 carbon atoms; m is 0 or an integer of 1 to 6; n is 0 or an integer of 1 to 6; t is 0 or 1, with the proviso that when Z is N, $R^5$ is a hydrogen atom, $-CH_2C_6H_4COOH$, $-CH_2C_6H_4COOR^{31}$, $-CH_2C_6H_4OH$, $-CH_2C_6H_4OR^{32}$, $-CH_2C_6H_4NH_2$, $-CH_2C_6H_4N(R^{33})_2$, $-CH_2C_6H_4$-azole, or $-CH_2C_6H_4NHR^{34}$ group, or a salt thereof.

Further, the present invention relates to a pharmaceutical composition comprising a benzene derivative of the formula (I) or a pharmaceutically acceptable salt thereof and a pharmaceutically acceptable carrier or diluent.

DETAILED DESCRIPTION OF THE PREFERRED EMBODIMENTS

The term "alkyl" as used herein includes straight-chain and branched alkyl groups, for example, an alkyl group of 1 to 4 carbon atoms, such as methyl, ethyl, n-propyl, i-propyl, n-butyl, i-butyl, s-butyl or t-butyl; an alkyl group of 1 to 5 carbon atoms, such as those as mentioned above, n-pentyl, i-pentyl, neopentyl, t-pentyl, 1-methylbutyl, 2-methylbutyl, 1,2-dimethylpropyl or 1-ethylpropyl; and an alkyl group of 1 to 6 carbon atoms, such as those as mentioned above, n-hexyl, i-hexyl or 2-ethylbutyl.

The haloalkyl group of 1 to 6 carbon atoms is the above alkyl group of 1 to 6 carbon atoms substituted with 1 to 13 halogen atoms as mentioned above. The halogen atom is, for example, a chlorine, bromine, fluorine or iodine atom. The preferred haloalkyl group is, for example, a trifluoromethyl, pentafluoroethyl, or 4,4,4-trifluorobutyl.

The azole group is a 5-membered cyclic group containing 2 to 4 heteroatoms, such as a nitrogen, oxygen or sulfur atom, such as a group of imidazole, oxazole, thiazole, pyrazole, isoxazole, isothiazole, triazole, oxadiazole, thiadiazole, tetrazole, oxatriazole or thiatriazole. The preferred azole group is a tetrazole group.

The three- to seven-membered saturated cycloaliphatic amino group is an alkyleneamino group which may be optionally interrupted by one or more heteroatoms such as nitrogen, oxygen or sulfur atoms, for example, 1-azetidinyl, 1-pyrrolidinyl, piperidino, morpholino, thiomorpholino, or 1-piperazinyl group.

The compound of the formula (I) wherein $R^1$ is a hydrogen atom, alkyl of 1 to 5 carbon atoms, haloalkyl of 1 to 5 carbon atoms, or $-NHR^{21}$ group; $R^2$ is a hydroxyl, $-OR^{22}$, three- to six-membered saturated cycloaliphatic amino group which may be interrupted by one or more nitrogen, oxygen or sulfur atoms, $-NHR^{23}$, $-N(R^{24})_2$, or $-NH_2$ group; $R^4$ is a hydrogen atom, alkyl of 1 to 4 carbon atoms, or $-C(=O)R^{25}$ group; $R^7$ is a $-CO-$ or $-SO_2-$; $R^8$ is a $-CO-$ or single bond; $R^{12}$ is $-R^{11}-R^5$; $R^{11}$ is $-N(R^5)-$, $-NH-$, $-O-$, $-N(R^{26})-$, $-N(C(=O)R^{27})-$, $-N(C(=O)NH_2)-$, or $-N(C(=O)NHR^{28})-$; $R^{13}$ is a hydrogen atom, alkyl of 1 to 4 carbon atoms, haloalkyl of 1 to 4 carbon atoms, $-NHC(=O)(CH_2)_mC_6H_5$, $-NHC(=O)R^{29}$, $-NHC(=O)CH(C_6H_5)_2$, $-NH_2$, $-NHR^{30}$, or $-(CH_2)_nC_6H_5$; Z is C, CH, or N; A is CH or N; $R^5$ is a hydrogen atom, $-CH_2C_6H_4COOH$, $-CH_2C_6H_4COOR^{31}$, $-CH_2C_6H_4OH$, $-CH_2C_6H_4OR^{32}$, $-CH_2C_6H_4NH_2$, $-CH_2C_6H_4N(R^{33})_2$, $-CH_2C_6H_4$-azole, $-CH_2C_6H_4NHR^{34}$, or $-CH_2C_6H_4C_6H_4R^{14}$ group; $R^{14}$ is an 1H-tetrazole or $-COOH$ group; $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, and $R^{34}$, are independently an alkyl of 1 to 4 carbon atoms or haloalkyl group of 1 to 4 carbon atoms; m is 0 or an integer of 1 to 4; n is 0 or an integer of 1 to 4; t is 0 or 1, with the proviso that when Z is N, $R^5$ is a hydrogen atom, $-CH_2C_6H_4COOH$, $-CH_2C_6H_4COOR^{31}$, $-CH_2C_6H_4OH$, $-CH_2C_6H_4OR^{32}$, $-CH_2C_6H_4NH_2$, $-CH_2C_6H_4N(R^{33})_2$, $-CH_2C_6H_4$-azole, or $-CH_2C_6H_4NHR^{34}$ group, or a salt thereof is preferable.

The compound of the formula (I) wherein $R^5$ is $-CH_2C_6H_4COOH$, or a salt thereof is more preferable.

The compound of the formula (I) wherein $R^5$ is $-CH_2C_6H_4$-4-COOH, or a salt thereof is most preferable.

The salt of the compound of the present invention includes a salt with an inorganic or organic acid or a salt with an inorganic or organic base, preferably a pharmaceutically acceptable salt. As an acid additive salt, there may be mentioned, for example, hydrochloride, sulfate, methanesulfonate or p-toluenesulfonate; a salt with a dicarboxylic acid, such as oxalic, malonic, succinic, maleic or fumaric acid; or a salt with a monocarboxylic acid, such as acetic, propionic or butyric acid. The inorganic base suitable to form a salt of the compound of the present invention is, for example, a hydroxide, carbonate or bicarbonate of ammonium, sodium, lithium, calcium, magnesium or aluminum. As the salt with the organic base, there may be mentioned, for example, a salt with a mono-, di- or trialkylamine, such as methylamine, dimethylamine or triethylamine; a salt with a mono-, di- or trihydroxyalkylamine, guanidine, N-methylglucosamine or amino acid salt.

As the typical examples of the compounds according to the present invention, the structures of Compounds No. 1 to 717 are shown in the following Tables 1 to 21. The compounds listed in the following Tables are sometimes referred to the numbers in the following Tables. In the following Tables, Me is methyl, Et is ethyl, Pr is propyl, Bu is butyl, Pen is pentyl, Hex is hexyl, Ph is phenyl, $CN_4H$ is 1H-tetrazol-5-yl, SB is single bond, $NC_4H_8O$ is morpholino, $NC_4H_8S$ is thiomorpholino, $NC_5H_{10}$ is piperidino, $NC_4H_8$ is 1-pyrrolidinyl, $NC_3H_6$ is 1-azetidinyl, $N_2C_4H_9$ is 1-piperazinyl, $CH_2PhPh$-2-$CN_4H$ is [2'-(1H-tetrazol-5-yl)biphenyl-4-yl]methyl, CO is carbonyl, and Ph-4- is 4-substituted phenylene.

TABLE 1

| No. | $R^1$ | A | Z | $R^2$ | $R^4$ | $R^7$ | $R^8$ | $R^{12}$ | $R^{13}$ |
|---|---|---|---|---|---|---|---|---|---|
| 1 | nBu | N | C | $NC_4H_8O$ | H | CO | CO | $NHCH_2Ph$-4-COOH | H |
| 2 | nBu | N | C | $NC_3H_6$ | H | CO | CO | $NHCH_2Ph$-4-COOH | H |
| 3 | nBu | N | C | $NC_4H_8$ | H | CO | CO | $NHCH_2Ph$-4-COOH | H |
| 4 | nBu | N | C | $NC_5H_{10}$ | H | CO | CO | $NHCH_2Ph$-4-COOH | H |
| 5 | nBu | N | C | $N_2C_4H_9$ | H | CO | CO | $NHCH_2Ph$-4-COOH | H |
| 6 | nBu | N | C | $NC_4H_8S$ | H | CO | CO | $NHCH_2Ph$-4-COOH | H |
| 7 | nBu | N | C | $NH_2$ | H | CO | CO | $NHCH_2Ph$-4-COOH | H |
| 8 | nBu | N | C | NHMe | H | CO | CO | $NHCH_2Ph$-4-COOH | H |
| 9 | nBu | N | C | NHEt | H | CO | CO | $NHCH_2Ph$-4-COOH | H |
| 10 | nBu | N | C | $NMe_2$ | H | CO | CO | $NHCH_2Ph$-4-COOH | H |
| 11 | nBu | N | C | $NEt_2$ | H | CO | CO | $NHCH_2Ph$-4-COOH | H |
| 12 | nBu | N | C | OH | H | CO | CO | $NHCH_2Ph$-4-COOH | H |
| 13 | nBu | N | C | OMe | H | CO | CO | $NHCH_2Ph$-4-COOH | H |
| 14 | nBu | N | C | OEt | H | CO | CO | $NHCH_2Ph$-4-COOH | H |
| 15 | H | N | C | $NC_4H_8O$ | H | CO | CO | $NHCH_2Ph$-4-COOH | H |
| 16 | Me | N | C | $NC_4H_8O$ | H | CO | CO | $NHCH_2Ph$-4-COOH | H |
| 17 | Et | N | C | $NC_4H_8O$ | H | CO | CO | $NHCH_2Ph$-4-COOH | H |
| 18 | nPr | N | C | $NC_4H_8O$ | H | CO | CO | $NHCH_2Ph$-4-COOH | H |
| 19 | nPen | N | C | $NC_4H_8O$ | H | CO | CO | $NHCH_2Ph$-4-COOH | H |
| 20 | nHex | N | C | $NC_4H_8O$ | H | CO | CO | $NHCH_2Ph$-4-COOH | H |
| 21 | MeNH | N | C | $NC_4H_8O$ | H | CO | CO | $NHCH_2Ph$-4-COOH | H |
| 22 | EtNH | N | C | $NC_4H_8O$ | H | CO | CO | $NHCH_2Ph$-4-COOH | H |
| 23 | nPrNH | N | C | $NC_4H_8O$ | H | CO | CO | $NHCH_2Ph$-4-COOH | H |
| 24 | nBuNH | N | C | $NC_4H_8O$ | H | CO | CO | $NHCH_2Ph$-4-COOH | H |
| 25 | nPenNH | N | C | $NC_4H_8O$ | H | CO | CO | $NHCH_2Ph$-4-COOH | H |
| 26 | Et | N | C | $N_2C_4H_9$ | H | CO | CO | $NHCH_2Ph$-4-COOH | H |
| 27 | nHex | N | C | $N_2C_4H_9$ | H | CO | CO | $NHCH_2Ph$-4-COOH | H |
| 28 | nPenNH | N | C | $N_2C_4H_9$ | H | CO | CO | $NHCH_2Ph$-4-COOH | H |
| 29 | Et | N | C | $NC_4H_8$ | H | CO | CO | $NHCH_2Ph$-4-COOH | H |
| 30 | nHex | N | C | $NC_4H_8$ | H | CO | CO | $NHCH_2Ph$-4-COOH | H |
| 31 | nPenNH | N | C | $NC_4H_8$ | H | CO | CO | $NHCH_2Ph$-4-COOH | H |
| 32 | Et | N | C | $NEt_2$ | H | CO | CO | $NHCH_2Ph$-4-COOH | H |
| 33 | nHex | N | C | $NEt_2$ | H | CO | CO | $NHCH_2Ph$-4-COOH | H |
| 34 | nPenNH | N | C | $NEt_2$ | H | CO | CO | $NHCH_2Ph$-4-COOH | H |
| 35 | Et | N | C | OH | H | CO | CO | $NHCH_2Ph$-4-COOH | H |

TABLE 2

| No. | $R^1$ | A | Z | $R^2$ | $R^4$ | $R^7$ | $R^8$ | $R^{12}$ | $R^{13}$ |
|---|---|---|---|---|---|---|---|---|---|
| 36 | nHex | N | C | OH | H | CO | CO | $NHCH_2Ph$-4-COOH | H |
| 37 | nPenNH | N | C | OH | H | CO | CO | $NHCH_2Ph$-4-COOH | H |
| 38 | Et | N | C | $NC_4H_8O$ | H | CO | SB | $NHCH_2Ph$-4-COOH | H |
| 39 | nBu | N | C | $NC_4H_8O$ | H | CO | SB | $NHCH_2Ph$-4-COOH | H |
| 40 | nHex | N | C | $NC_4H_8O$ | H | CO | SB | $NHCH_2Ph$-4-COOH | H |
| 41 | nPen | N | C | $NC_4H_8O$ | Me | CO | SB | $NHCH_2Ph$-4-COOH | H |
| 42 | nPen | N | C | $NC_3H_6$ | Me | CO | SB | $NHCH_2Ph$-4-COOH | H |
| 43 | nPen | N | C | $NC_4H_8$ | Me | CO | SB | $NHCH_2Ph$-4-COOH | H |
| 44 | nPen | N | C | $NC_5H_{10}$ | Me | CO | SB | $NHCH_2Ph$-4-COOH | H |
| 45 | nPen | N | C | $N_2C_4H_9$ | Me | CO | SB | $NHCH_2Ph$-4-COOH | H |
| 46 | nPen | N | C | $NC_4H_8S$ | Me | CO | SB | $NHCH_2Ph$-4-COOH | H |
| 47 | nPen | N | C | $NH_2$ | Me | CO | SB | $NHCH_2Ph$-4-COOH | H |
| 48 | nPen | N | C | NHMe | Me | CO | SB | $NHCH_2Ph$-4-COOH | H |
| 49 | nPen | N | C | NHEt | Me | CO | SB | $NHCH_2Ph$-4-COOH | H |
| 50 | nPen | N | C | $NMe_2$ | Me | CO | SB | $NHCH_2Ph$-4-COOH | H |
| 51 | nPen | N | C | $NEt_2$ | Me | CO | SB | $NHCH_2Ph$-4-COOH | H |
| 52 | nPen | N | C | OH | Me | CO | SB | $NHCH_2Ph$-4-COOH | H |
| 53 | nPen | N | C | OMe | Me | CO | SB | $NHCH_2Ph$-4-COOH | H |
| 54 | nPen | N | C | OEt | Me | CO | SB | $NHCH_2Ph$-4-COOH | H |
| 55 | H | N | C | $NC_4H_8O$ | Me | CO | SB | $NHCH_2Ph$-4-COOH | H |
| 56 | Me | N | C | $NC_4H_8O$ | Me | CO | SB | $NHCH_2Ph$-4-COOH | H |
| 57 | Et | N | C | $NC_4H_8O$ | Me | CO | SB | $NHCH_2Ph$-4-COOH | H |
| 58 | nPr | N | C | $NC_4H_8O$ | Me | CO | SB | $NHCH_2Ph$-4-COOH | H |

TABLE 2-continued

| No. | R¹ | A | Z | R² | R⁴ | R⁷ | R⁸ | R¹² | R¹³ |
|---|---|---|---|---|---|---|---|---|---|
| 59 | nBu | N | C | NC₄H₈O | Me | CO | SB | NHCH₂Ph-4-COOH | H |
| 60 | nHex | N | C | NC₄H₈O | Me | CO | SB | NHCH₂Ph-4-COOH | H |
| 61 | Et | N | C | N₂C₄H₉ | Me | CO | SB | NHCH₂Ph-4-COOH | H |
| 62 | nHex | N | C | N₂C₄H₉ | Me | CO | SB | NHCH₂Ph-4-COOH | H |
| 63 | Et | N | C | NC₄H₈ | Me | CO | SB | NHCH₂Ph-4-COOH | H |
| 64 | nHex | N | C | NC₄H₈ | Me | CO | SB | NHCH₂Ph-4-COOH | H |
| 65 | Et | N | C | NEt₂ | Me | CO | SB | NHCH₂Ph-4-COOH | H |
| 66 | nHex | N | C | NEt₂ | Me | CO | SB | NHCH₂Ph-4-COOH | H |
| 67 | Et | N | C | OH | Me | CO | SB | NHCH₂Ph-4-COOH | H |
| 68 | nHex | N | C | OH | Me | CO | SB | NHCH₂Ph-4-COOH | H |
| 69 | Et | N | C | NC₄H₈O | Et | CO | SB | NHCH₂Ph-4-COOH | H |
| 70 | H | CH | C | NC₄H₈O | H | CO | SB | NHCH₂Ph-4-COOH | H |

TABLE 3

| No. | R¹ | A | Z | R² | R⁴ | R⁷ | R⁸ | R¹² | R¹³ |
|---|---|---|---|---|---|---|---|---|---|
| 71 | Me | CH | C | NC₄H₈O | H | CO | SB | NHCH₂Ph-4-COOH | H |
| 72 | Et | CH | C | NC₄H₈O | H | CO | SB | NHCH₂Ph-4-COOH | H |
| 73 | nPr | CH | C | NC₄H₈O | H | CO | SB | NHCH₂Ph-4-COOH | H |
| 74 | nBu | CH | C | NC₄H₈O | H | CO | SB | NHCH₂Ph-4-COOH | H |
| 75 | nPen | CH | C | NC₄H₈O | H | CO | SB | NHCH₂Ph-4-COOH | H |
| 76 | nPen | CH | C | N₂C₄H₉ | H | CO | SB | NHCH₂Ph-4-COOH | H |
| 77 | nPen | CH | C | NC₄H₈ | H | CO | SB | NHCH₂Ph-4-COOH | H |
| 78 | nPen | CH | C | NEt₂ | H | CO | SB | NHCH₂Ph-4-COOH | H |
| 79 | nPen | CH | C | OH | H | CO | SB | NHCH₂Ph-4-COOH | H |
| 80 | Me | CH | C | NC₄H₈O | Me | CO | SB | NHCH₂Ph-4-COOH | H |
| 81 | Et | CH | C | NC₄H₈O | Et | CO | SB | NHCH₂Ph-4-COOH | H |
| 82 | H | CH | C | N₂C₄H₉ | H | CO | SB | NHCH₂Ph-4-COOH | H |
| 83 | H | CH | C | NC₄H₈ | H | CO | SB | NHCH₂Ph-4-COOH | H |
| 84 | H | CH | C | NEt₂ | H | CO | SB | NHCH₂Ph-4-COOH | H |
| 85 | H | CH | C | OH | H | CO | SB | NHCH₂Ph-4-COOH | H |
| 86 | Me | CH | C | N₂C₄H₉ | Me | CO | SB | NHCH₂Ph-4-COOH | H |
| 87 | Me | CH | C | NC₄H₈ | Me | CO | SB | NHCH₂Ph-4-COOH | H |
| 88 | Me | CH | C | NEt₂ | Me | CO | SB | NHCH₂Ph-4-COOH | H |
| 89 | Me | CH | C | OH | Me | CO | SB | NHCH₂Ph-4-COOH | H |
| 90 | — | — | CH | NC₄H₈O | — | CO | — | N(CO—nBu)CH₂Ph-4-COOH | H |
| 91 | — | — | CH | NC₃H₆ | — | CO | — | N(CO—nBu)CH₂Ph-4-COOH | H |
| 92 | — | — | CH | NC₄H₈ | — | CO | — | N(CO—nBu)CH₂Ph-4-COOH | H |
| 93 | — | — | CH | NC₅H₁₀ | — | CO | — | N(CO—nBu)CH₂Ph-4-COOH | H |
| 94 | — | — | CH | NC₄H₈S | — | CO | — | N(CO—nBu)CH₂Ph-4-COOH | H |
| 95 | — | — | CH | N₂C₄H₉ | — | CO | — | N(CO—nBu)CH₂Ph-4-COOH | H |
| 96 | — | — | CH | NH₂ | — | CO | — | N(CO—nBu)CH₂Ph-4-COOH | H |
| 97 | — | — | CH | NHMe | — | CO | — | N(CO—nBu)CH₂Ph-4-COOH | H |
| 98 | — | — | CH | NHEt | — | CO | — | N(CO—nBu)CH₂Ph-4-COOH | H |
| 99 | — | — | CH | NMe₂ | — | CO | — | N(CO—nBu)CH₂Ph-4-COOH | H |
| 100 | — | — | CH | NEt₂ | — | CO | — | N(CO—nBu)CH₂Ph-4-COOH | H |
| 101 | — | — | CH | OH | — | CO | — | N(CO—nBu)CH₂Ph-4-COOH | H |
| 102 | — | — | CH | OMe | — | CO | — | N(CO—nBu)CH₂Ph-4-COOH | H |
| 103 | — | — | CH | OEt | — | CO | — | N(CO—nBu)CH₂Ph-4-COOH | H |
| 104 | — | — | CH | NC₄H₈O | — | CO | — | N(CO—Me)CH₂Ph-4-COOH | H |
| 105 | — | — | CH | NC₄H₈O | — | CO | — | N(CO—Et)CH₂Ph-4-COOH | H |

TABLE 4

| No. | R¹ | A | Z | R² | R⁴ | R⁷ | R⁸ | R¹² | R¹³ |
|---|---|---|---|---|---|---|---|---|---|
| 106 | — | — | CH | NC₄H₈O | — | CO | — | N(CO—nPr)CH₂Ph-4-COOH | H |
| 107 | — | — | CH | NC₄H₈O | — | CO | — | N(CO—nPen)CH₂Ph-4-COOH | H |
| 108 | — | — | CH | NC₄H₈O | — | CO | — | N(CO—nHex)CH₂Ph-4-COOH | H |
| 109 | — | — | CH | N₂C₄H₉ | — | CO | — | N(CO—Me)CH₂Ph-4-COOH | H |
| 110 | — | — | CH | NC₄H₈ | — | CO | — | N(CO—Me)CH₂Ph-4-COOH | H |
| 111 | — | — | CH | NEt₂ | — | CO | — | N(CO—Me)CH₂Ph-4-COOH | H |
| 112 | — | — | CH | OH | — | CO | — | N(CO—Me)CH₂Ph-4-COOH | H |
| 113 | — | — | CH | N₂C₄H₉ | — | CO | — | N(CO—Et)CH₂Ph-4-COOH | H |
| 114 | — | — | CH | NC₄H₈ | — | CO | — | N(CO—Et)CH₂Ph-4-COOH | H |
| 115 | — | — | CH | NEt₂ | — | CO | — | N(CO—Et)CH₂Ph-4-COOH | H |
| 116 | — | — | CH | OH | — | CO | — | N(CO—Et)CH₂Ph-4-COOH | H |
| 117 | — | — | CH | N₂C₄H₉ | — | CO | — | N(CO—nPr)CH₂Ph-4-COOH | H |
| 118 | — | — | CH | NC₄H₈ | — | CO | — | N(CO—nPr)CH₂Ph-4-COOH | H |
| 119 | — | — | CH | NEt₂ | — | CO | — | N(CO—nPr)CH₂Ph-4-COOH | H |
| 120 | — | — | CH | OH | — | CO | — | N(CO—nPr)CH₂Ph-4-COOH | H |

TABLE 4-continued

| No. | R$^1$ | A | Z | R$^2$ | R$^4$ | R$^7$ | R$^8$ | R$^{12}$ | R$^{13}$ |
|---|---|---|---|---|---|---|---|---|---|
| 121 | — | — | CH | N$_2$C$_4$H$_9$ | — | CO | — | N(CO—nPen)CH$_2$Ph-4-COOH | H |
| 122 | — | — | CH | NC$_4$H$_8$ | — | CO | — | N(CO—nPen)CH$_2$Ph-4-COOH | H |
| 123 | — | — | CH | NEt$_2$ | — | CO | — | N(CO—nPen)CH$_2$Ph-4-COOH | H |
| 124 | — | — | CH | OH | — | CO | — | N(CO—nPen)CH$_2$Ph-4-COOH | H |
| 125 | — | — | CH | N$_2$C$_4$H$_9$ | — | CO | — | N(CO—nHex)CH$_2$Ph-4-COOH | H |
| 126 | — | — | CH | NC$_4$H$_8$ | — | CO | — | N(CO—nHex)CH$_2$Ph-4-COOH | H |
| 127 | — | — | CH | NEt$_2$ | — | CO | — | N(CO—nHex)CH$_2$Ph-4-COOH | H |
| 128 | — | — | CH | OH | — | CO | — | N(CO—nHex)CH$_2$Ph-4-COOH | H |
| 129 | — | — | CH | NC$_4$H$_8$O | — | CO | — | N(CONH—Me)CH$_2$Ph-4-COOH | H |
| 130 | — | — | CH | NC$_4$H$_8$O | — | CO | — | N(CONH—Et)CH$_2$Ph-4-COOH | H |
| 131 | — | — | CH | NC$_4$H$_8$O | — | CO | — | N(CONH—nPr)CH$_2$Ph-4-COOH | H |
| 132 | — | — | CH | NC$_4$H$_8$O | — | CO | — | N(CONH—nBu)CH$_2$Ph-4-COOH | H |
| 133 | — | — | CH | NC$_4$H$_8$O | — | CO | — | N(CONH—nPen)CH$_2$Ph-4-COOH | H |
| 134 | — | — | CH | N$_2$C$_4$H$_9$ | — | CO | — | N(CONH—Me)CH$_2$Ph-4-COOH | H |
| 135 | — | — | CH | NC$_4$H$_8$ | — | CO | — | N(CONH—Me)CH$_2$Ph-4-COOH | H |
| 136 | — | — | CH | NEt$_2$ | — | CO | — | N(CONH—Me)CH$_2$Ph-4-COOH | H |
| 137 | — | — | CH | OH | — | CO | — | N(CONH—Me)CH$_2$Ph-4-COOH | H |
| 138 | — | — | CH | N$_2$C$_4$H$_9$ | — | CO | — | N(CONH—Et)CH$_2$Ph-4-COOH | H |
| 139 | — | — | CH | NC$_4$H$_8$ | — | CO | — | N(CONH—Et)CH$_2$Ph-4-COOH | H |
| 140 | — | — | CH | NEt$_2$ | — | CO | — | N(CONH—Et)CH$_2$Ph-4-COOH | H |

TABLE 5

| No. | R$^1$ | A | Z | R$^2$ | R$^4$ | R$^7$ | R$^8$ | R$^{12}$ | R$^{13}$ |
|---|---|---|---|---|---|---|---|---|---|
| 141 | — | — | CH | OH | — | CO | — | N(CONH—Et)CH$_2$Ph-4-COOH | H |
| 142 | — | — | CH | N$_2$C$_4$H$_9$ | — | CO | — | N(CONH—nPr)CH$_2$Ph-4-COOH | H |
| 143 | — | — | CH | NC$_4$H$_8$ | — | CO | — | N(CONH—nPr)CH$_2$Ph-4-COOH | H |
| 144 | — | — | CH | NEt$_2$ | — | CO | — | N(CONH—nPr)CH$_2$Ph-4-COOH | H |
| 145 | — | — | CH | OH | — | CO | — | N(CONH—nPr)CH$_2$Ph-4-COOH | H |
| 146 | — | — | CH | N$_2$C$_4$H$_9$ | — | CO | — | N(CONH—nBu)CH$_2$Ph-4-COOH | H |
| 147 | — | — | CH | NC$_4$H$_8$ | — | CO | — | N(CONH—nBu)CH$_2$Ph-4-COOH | H |
| 148 | — | — | CH | NEt$_2$ | — | CO | — | N(CONH—nBu)CH$_2$Ph-4-COOH | H |
| 149 | — | — | CH | OH | — | CO | — | N(CONH—nBu)CH$_2$Ph-4-COOH | H |
| 150 | — | — | CH | N$_2$C$_4$H$_9$ | — | CO | — | N(CONH—nPen)CH$_2$Ph-4-COOH | H |
| 151 | — | — | CH | NC$_4$H$_8$ | — | CO | — | N(CONH—nPen)CH$_2$Ph-4-COOH | H |
| 152 | — | — | CH | NEt$_2$ | — | CO | — | N(CONH—nPen)CH$_2$Ph-4-COOH | H |
| 153 | — | — | CH | OH | — | CO | — | N(CONH—nPen)CH$_2$Ph-4-COOH | H |
| 154 | — | — | CH | NC$_4$H$_8$O | — | CO | — | N(Me)CH$_2$Ph-4-COOH | H |
| 155 | — | — | CH | NC$_4$H$_8$O | — | CO | — | N(Et)CH$_2$Ph-4-COOH | H |
| 156 | — | — | CH | NC$_4$H$_8$O | — | CO | — | N(nPr)CH$_2$Ph-4-COOH | H |
| 157 | — | — | CH | NC$_4$H$_8$O | — | CO | — | N(nBu)CH$_2$Ph-4-COOH | H |
| 158 | — | — | CH | NC$_4$H$_8$O | — | CO | — | N(nPen)CH$_2$Ph-4-COOH | H |
| 159 | — | — | CH | NC$_4$H$_8$O | — | CO | — | N(nHex)CH$_2$Ph-4-COOH | H |
| 160 | — | — | CH | N$_2$C$_4$H$_9$ | — | CO | — | N(Me)CH$_2$Ph-4-COOH | H |
| 161 | — | — | CH | NC$_4$H$_8$ | — | CO | — | N(Me)CH$_2$Ph-4-COOH | H |
| 162 | — | — | CH | NEt$_2$ | — | CO | — | N(Me)CH$_2$Ph-4-COOH | H |
| 163 | — | — | CH | OH | — | CO | — | N(Me)CH$_2$Ph-4-COOH | H |
| 164 | — | — | CH | N$_2$C$_4$H$_9$ | — | CO | — | N(Et)CH$_2$Ph-4-COOH | H |
| 165 | — | — | CH | NC$_4$H$_8$ | — | CO | — | N(Et)CH$_2$Ph-4-COOH | H |
| 166 | — | — | CH | NEt$_2$ | — | CO | — | N(Et)CH$_2$Ph-4-COOH | H |
| 167 | — | — | CH | OH | — | CO | — | N(Et)CH$_2$Ph-4-COOH | H |
| 168 | — | — | CH | N$_2$C$_4$H$_9$ | — | CO | — | N(nPr)CH$_2$Ph-4-COOH | H |
| 169 | — | — | CH | NC$_4$H$_8$ | — | CO | — | N(nPr)CH$_2$Ph-4-COOH | H |
| 170 | — | — | CH | NEt$_2$ | — | CO | — | N(nPr)CH$_2$Ph-4-COOH | H |
| 171 | — | — | CH | OH | — | CO | — | N(nPr)CH$_2$Ph-4-COOH | H |
| 172 | — | — | CH | N$_2$C$_4$H$_9$ | — | CO | — | N(nBu)CH$_2$Ph-4-COOH | H |
| 173 | — | — | CH | NC$_4$H$_8$ | — | CO | — | N(nBu)CH$_2$Ph-4-COOH | H |
| 174 | — | — | CH | NEt$_2$ | — | CO | — | N(nBu)CH$_2$Ph-4-COOH | H |
| 175 | — | — | CH | OH | — | CO | — | N(nBu)CH$_2$Ph-4-COOH | H |

TABLE 6

| No. | R$^1$ | A | Z | R$^2$ | R$^4$ | R$^7$ | R$^8$ | R$^{12}$ | R$^{13}$ |
|---|---|---|---|---|---|---|---|---|---|
| 176 | — | — | CH | N$_2$C$_4$H$_9$ | — | CO | — | N(nPen)CH$_2$Ph-4-COOH | H |
| 177 | — | — | CH | NC$_4$H$_8$ | — | CO | — | N(nPen)CH$_2$Ph-4-COOH | H |
| 178 | — | — | CH | NEt$_2$ | — | CO | — | N(nPen)CH$_2$Ph-4-COOH | H |
| 179 | — | — | CH | OH | — | CO | — | N(nPen)CH$_2$Ph-4-COOH | H |
| 180 | — | — | CH | N$_2$C$_4$H$_9$ | — | CO | — | N(nHex)CH$_2$Ph-4-COOH | H |
| 181 | — | — | CH | NC$_4$H$_8$ | — | CO | — | N(nHex)CH$_2$Ph-4-COOH | H |
| 182 | — | — | CH | NEt$_2$ | — | CO | — | N(nHex)CH$_2$Ph-4-COOH | H |

TABLE 6-continued

| No. | R¹ | A | Z | R² | R⁴ | R⁷ | R⁸ | R¹² | R¹³ |
|---|---|---|---|---|---|---|---|---|---|
| 183 | — | — | CH | OH | — | CO | — | N(nHex)CH₂Ph-4-COOH | H |
| 184 | Me | N | C | NC₄H₈O | Me | CO | SB | N(CO—nBu)CH₂Ph-4-COOH | H |
| 185 | Me | N | C | NC₃H₆ | Me | CO | SB | N(CO—nBu)CH₂Ph-4-COOH | H |
| 186 | Me | N | C | NC₄H₈ | Me | CO | SB | N(CO—nBu)CH₂Ph-4-COOH | H |
| 187 | Me | N | C | NC₅H₁₀ | Me | CO | SB | N(CO—nBu)CH₂Ph-4-COOH | H |
| 188 | Me | N | C | NC₄H₈S | Me | CO | SB | N(CO—nBu)CH₂Ph-4-COOH | H |
| 189 | Me | N | C | N₂C₄H₉ | Me | CO | SB | N(CO—nBu)CH₂Ph-4-COOH | H |
| 190 | Me | N | C | NH₂ | Me | CO | SB | N(CO—nBu)CH₂Ph-4-COOH | H |
| 191 | Me | N | C | NHMe | Me | CO | SB | N(CO—nBu)CH₂Ph-4-COOH | H |
| 192 | Me | N | C | NHEt | Me | CO | SB | N(CO—nBu)CH₂Ph-4-COOH | H |
| 193 | Me | N | C | NMe₂ | Me | CO | SB | N(CO—nBu)CH₂Ph-4-COOH | H |
| 194 | Me | N | C | NEt₂ | Me | CO | SB | N(CO—nBu)CH₂Ph-4-COOH | H |
| 195 | Me | N | C | OH | Me | CO | SB | N(CO—nBu)CH₂Ph-4-COOH | H |
| 196 | Me | N | C | OMe | Me | CO | SB | N(CO—nBu)CH₂Ph-4-COOH | H |
| 197 | Me | N | C | OEt | Me | CO | SB | N(CO—nBu)CH₂Ph-4-COOH | H |
| 198 | Me | N | C | NC₄H₈O | Me | CO | SB | N(CO—Me)CH₂Ph-4-COOH | H |
| 199 | Me | N | C | NC₄H₈O | Me | CO | SB | N(CO—Et)CH₂Ph-4-COOH | H |
| 200 | Me | N | C | NC₄H₈O | Me | CO | SB | N(CO—nPr)CH₂Ph-4-COOH | H |
| 201 | Me | N | C | NC₄H₈O | Me | CO | SB | N(CO—nPen)CH₂Ph-4-COOH | H |
| 202 | Me | N | C | NC₄H₈O | Me | CO | SB | N(CO—nHex)CH₂Ph-4-COOH | H |
| 203 | Me | N | C | N₂C₄H₉ | Me | CO | SB | N(CO—Me)CH₂Ph-4-COOH | H |
| 204 | Me | N | C | NC₄H₈ | Me | CO | SB | N(CO—Me)CH₂Ph-4-COOH | H |
| 205 | Me | N | C | NEt₂ | Me | CO | SB | N(CO—Me)CH₂Ph-4-COOH | H |
| 206 | Me | N | C | OH | Me | CO | SB | N(CO—Me)CH₂Ph-4-COOH | H |
| 207 | Me | N | C | N₂C₄H₉ | Me | CO | SB | N(CO—Et)CH₂Ph-4-COOH | H |
| 208 | Me | N | C | NC₄H₈ | Me | CO | SB | N(CO—Et)CH₂Ph-4-COOH | H |
| 209 | Me | N | C | NEt₂ | Me | CO | SB | N(CO—Et)CH₂Ph-4-COOH | H |
| 210 | Me | N | C | OH | Me | CO | SB | N(CO—Et)CH₂Ph-4-COOH | H |

TABLE 7

| No. | R¹ | A | Z | R² | R⁴ | R⁷ | R⁸ | R¹² | R¹³ |
|---|---|---|---|---|---|---|---|---|---|
| 211 | Me | N | C | N₂C₄H₉ | Me | CO | SB | N(CO—nPr)CH₂Ph-4-COOH | H |
| 212 | Me | N | C | NC₄H₈ | Me | CO | SB | N(CO—nPr)CH₂Ph-4-COOH | H |
| 213 | Me | N | C | NEt₂ | Me | CO | SB | N(CO—nPr)CH₂Ph-4-COOH | H |
| 214 | Me | N | C | OH | Me | CO | SB | N(CO—nPr)CH₂Ph-4-COOH | H |
| 215 | Me | N | C | N₂C₄H₉ | Me | CO | SB | N(CO—nPen)CH₂Ph-4-COOH | H |
| 216 | Me | N | C | NC₄H₈ | Me | CO | SB | N(CO—nPen)CH₂Ph-4-COOH | H |
| 217 | Me | N | C | NEt₂ | Me | CO | SB | N(CO—nPen)CH₂Ph-4-COOH | H |
| 218 | Me | N | C | OH | Me | CO | SB | N(CO—nPen)CH₂Ph-4-COOH | H |
| 219 | Me | N | C | N₂C₄H₉ | Me | CO | SB | N(CO—nHex)CH₂Ph-4-COOH | H |
| 220 | Me | N | C | NC₄H₈ | Me | CO | SB | N(CO—nHex)CH₂Ph-4-COOH | H |
| 221 | Me | N | C | NEt₂ | Me | CO | SB | N(CO—nHex)CH₂Ph-4-COOH | H |
| 222 | Me | N | C | OH | Me | CO | SB | N(CO—nHex)CH₂Ph-4-COOH | H |
| 223 | Me | N | C | NC₄H₈O | Me | CO | SB | N(CONH—Me)CH₂Ph-4-COOH | H |
| 224 | Me | N | C | NC₄H₈O | Me | CO | SB | N(CONH—Et)CH₂Ph-4-COOH | H |
| 225 | Me | N | C | NC₄H₈O | Me | CO | SB | N(CONH—nPr)CH₂Ph-4-COOH | H |
| 226 | Me | N | C | NC₄H₈O | Me | CO | SB | N(CONH—nBu)CH₂Ph-4-COOH | H |
| 227 | Me | N | C | NC₄H₈O | Me | CO | SB | N(CONH—nPen)CH₂Ph-4-COOH | H |
| 228 | Me | N | C | N₂C₄H₉ | Me | CO | SB | N(CONH—Me)CH₂Ph-4-COOH | H |
| 229 | Me | N | C | NC₄H₈ | Me | CO | SB | N(CONH—Me)CH₂Ph-4-COOH | H |
| 230 | Me | N | C | NEt₂ | Me | CO | SB | N(CONH—Me)CH₂Ph-4-COOH | H |
| 231 | Me | N | C | OH | Me | CO | SB | N(CONH—Me)CH₂Ph-4-COOH | H |
| 232 | Me | N | C | N₂C₄H₉ | Me | CO | SB | N(CONH—Et)CH₂Ph-4-COOH | H |
| 233 | Me | N | C | NC₄H₈ | Me | CO | SB | N(CONH—Et)CH₂Ph-4-COOH | H |
| 234 | Me | N | C | NEt₂ | Me | CO | SB | N(CONH—Et)CH₂Ph-4-COOH | H |
| 235 | Me | N | C | OH | Me | CO | SB | N(CONH—Et)CH₂Ph-4-COOH | H |
| 236 | Me | N | C | N₂C₄H₉ | Me | CO | SB | N(CONH—nPr)CH₂Ph-4-COOH | H |
| 237 | Me | N | C | NC₄H₈ | Me | CO | SB | N(CONH—nPr)CH₂Ph-4-COOH | H |
| 238 | Me | N | C | NEt₂ | Me | CO | SB | N(CONH—nPr)CH₂Ph-4-COOH | H |
| 239 | Me | N | C | OH | Me | CO | SB | N(CONH—nPr)CH₂Ph-4-COOH | H |
| 240 | Me | N | C | N₂C₄H₉ | Me | CO | SB | N(CONH—nBu)CH₂Ph-4-COOH | H |
| 241 | Me | N | C | NC₄H₈ | Me | CO | SB | N(CONH—nBu)CH₂Ph-4-COOH | H |
| 242 | Me | N | C | NEt₂ | Me | CO | SB | N(CONH—nBu)CH₂Ph-4-COOH | H |
| 243 | Me | N | C | OH | Me | CO | SB | N(CONH—nBu)CH₂Ph-4-COOH | H |
| 244 | Me | N | C | N₂C₄H₉ | Me | CO | SB | N(CONH—nPen)CH₂Ph-4-COOH | H |
| 245 | Me | N | C | NC₄H₈ | Me | CO | SB | N(CONH—nPen)CH₂Ph-4-COOH | H |

TABLE 8

| No. | R¹ | A | Z | R² | R⁴ | R⁷ | R⁸ | R¹² | R¹³ |
|---|---|---|---|---|---|---|---|---|---|
| 246 | Me | N | C | NEt₂ | Me | CO | SB | N(CONH—nPen)CH₂Ph-4-COOH | H |
| 247 | Me | N | C | OH | Me | CO | SB | N(CONH—nPen)CH₂Ph-4-COOH | H |
| 248 | Me | N | C | NC₄H₈O | Me | CO | SB | N(Me)CH₂Ph-4-COOH | H |
| 249 | Me | N | C | NC₄H₈O | Me | CO | SB | N(Et)CH₂Ph-4-COOH | H |
| 250 | Me | N | C | NC₄H₈O | Me | CO | SB | N(nPr)CH₂Ph-4-COOH | H |
| 251 | Me | N | C | NC₄H₈O | Me | CO | SB | N(nBu)CH₂Ph-4-COOH | H |
| 252 | Me | N | C | NC₄H₈O | Me | CO | SB | N(nPen)CH₂Ph-4-COOH | H |
| 253 | Me | N | C | NC₄H₈O | Me | CO | SB | N(nHex)CH₂Ph-4-COOH | H |
| 254 | Me | N | C | N₂C₄H₉ | Me | CO | SB | N(Me)CH₂Ph-4-COOH | H |
| 255 | Me | N | C | NC₄H₈ | Me | CO | SB | N(Me)CH₂Ph-4-COOH | H |
| 256 | Me | N | C | NEt₂ | Me | CO | SB | N(Me)CH₂Ph-4-COOH | H |
| 257 | Me | N | C | OH | Me | CO | SB | N(Me)CH₂Ph-4-COOH | H |
| 258 | Me | N | C | N₂C₄H₉ | Me | CO | SB | N(Et)CH₂Ph-4-COOH | H |
| 259 | Me | N | C | NC₄H₈ | Me | CO | SB | N(Et)CH₂Ph-4-COOH | H |
| 260 | Me | N | C | NEt₂ | Me | CO | SB | N(Et)CH₂Ph-4-COOH | H |
| 261 | Me | N | C | OH | Me | CO | SB | N(Et)CH₂Ph-4-COOH | H |
| 262 | Me | N | C | N₂C₄H₉ | Me | CO | SB | N(nPr)CH₂Ph-4-COOH | H |
| 263 | Me | N | C | NC₄H₈ | Me | CO | SB | N(nPr)CH₂Ph-4-COOH | H |
| 264 | Me | N | C | NEt₂ | Me | CO | SB | N(nPr)CH₂Ph-4-COOH | H |
| 265 | Me | N | C | OH | Me | CO | SB | N(nPr)CH₂Ph-4-COOH | H |
| 266 | Me | N | C | N₂C₄H₉ | Me | CO | SB | N(nBu)CH₂Ph-4-COOH | H |
| 267 | Me | N | C | NC₄H₈ | Me | CO | SB | N(nBu)CH₂Ph-4-COOH | H |
| 268 | Me | N | C | NEt₂ | Me | CO | SB | N(nBu)CH₂Ph-4-COOH | H |
| 269 | Me | N | C | OH | Me | CO | SB | N(nBu)CH₂Ph-4-COOH | H |
| 270 | Me | N | C | N₂C₄H₉ | Me | CO | SB | N(nPen)CH₂Ph-4-COOH | H |
| 271 | Me | N | C | NC₄H₈ | Me | CO | SB | N(nPen)CH₂Ph-4-COOH | H |
| 272 | Me | N | C | NEt₂ | Me | CO | SB | N(nPen)CH₂Ph-4-COOH | H |
| 273 | Me | N | C | OH | Me | CO | SB | N(nPen)CH₂Ph-4-COOH | H |
| 274 | Me | N | C | N₂C₄H₉ | Me | CO | SB | N(nHex)CH₂Ph-4-COOH | H |
| 275 | Me | N | C | NC₄H₈ | Me | CO | SB | N(nHex)CH₂Ph-4-COOH | H |
| 276 | Me | N | C | NEt₂ | Me | CO | SB | N(nHex)CH₂Ph-4-COOH | H |
| 277 | Me | N | C | OH | Me | CO | SB | N(nHex)CH₂Ph-4-COOH | H |
| 278 | H | CH | C | NC₄H₈O | H | CO | SB | N(CO—nBu)CH₂Ph-4-COOH | H |
| 279 | H | CH | C | NC₃H₆ | H | CO | SB | N(CO—nBu)CH₂Ph-4-COOH | H |
| 280 | H | CH | C | NC₄H₈ | H | CO | SB | N(CO—nBu)CH₂Ph-4-COOH | H |

TABLE 9

| No. | R¹ | A | Z | R² | R⁴ | R⁷ | R⁸ | R¹² | R¹³ |
|---|---|---|---|---|---|---|---|---|---|
| 281 | H | CH | C | NC₅H₁₀ | H | CO | SB | N(CO—nBu)CH₂Ph-4-COOH | H |
| 282 | H | CH | C | NC₄H₈S | H | CO | SB | N(CO—nBu)CH₂Ph-4-COOH | H |
| 283 | H | CH | C | N₂C₄H₉ | H | CO | SB | N(CO—nBu)CH₂Ph-4-COOH | H |
| 284 | H | CH | C | NH₂ | H | CO | SB | N(CO—nBu)CH₂Ph-4-COOH | H |
| 285 | H | CH | C | NHMe | H | CO | SB | N(CO—nBu)CH₂Ph-4-COOH | H |
| 286 | H | CH | C | NHEt | H | CO | SB | N(CO—nBu)CH₂Ph-4-COOH | H |
| 287 | H | CH | C | NMe₂ | H | CO | SB | N(CO—nBu)CH₂Ph-4-COOH | H |
| 288 | H | CH | C | NEt₂ | H | CO | SB | N(CO—nBu)CH₂Ph-4-COOH | H |
| 289 | H | CH | C | OH | H | CO | SB | N(CO—nBu)CH₂Ph-4-COOH | H |
| 290 | H | CH | C | OMe | H | CO | SB | N(CO—nBu)CH₂Ph-4-COOH | H |
| 291 | H | CH | C | OEt | H | CO | SB | N(CO—nBu)CH₂Ph-4-COOH | H |
| 292 | H | CH | C | NC₄H₈O | H | CO | SB | N(CO—Me)CH₂Ph-4-COOH | H |
| 293 | H | CH | C | NC₄H₈O | H | CO | SB | N(CO—Et)CH₂Ph-4-COOH | H |
| 294 | H | CH | C | NC₄H₈O | H | CO | SB | N(CO—nPr)CH₂Ph-4-COOH | H |
| 295 | H | CH | C | NC₄H₈O | H | CO | SB | N(CO—nPen)CH₂Ph-4-COOH | H |
| 296 | H | CH | C | NC₄H₈O | H | CO | SB | N(CO—nHex)CH₂Ph-4-COOH | H |
| 297 | H | CH | C | N₂C₄H₉ | H | CO | SB | N(CO—Me)CH₂Ph-4-COOH | H |
| 298 | H | CH | C | NC₄H₈ | H | CO | SB | N(CO—Me)CH₂Ph-4-COOH | H |
| 299 | H | CH | C | NEt₂ | H | CO | SB | N(CO—Me)CH₂Ph-4-COOH | H |
| 300 | H | CH | C | OH | H | CO | SB | N(CO—Me)CH₂Ph-4-COOH | H |
| 301 | H | CH | C | N₂C₄H₉ | H | CO | SB | N(CO—Et)CH₂Ph-4-COOH | H |
| 302 | H | CH | C | NC₄H₈ | H | CO | SB | N(CO—Et)CH₂Ph-4-COOH | H |
| 303 | H | CH | C | NEt₂ | H | CO | SB | N(CO—Et)CH₂Ph-4-COOH | H |
| 304 | H | CH | C | OH | H | CO | SB | N(CO—Et)CH₂Ph-4-COOH | H |
| 305 | H | CH | C | N₂C₄H₉ | H | CO | SB | N(CO—nPr)CH₂Ph-4-COOH | H |
| 306 | H | CH | C | NC₄H₈ | H | CO | SB | N(CO—nPr)CH₂Ph-4-COOH | H |
| 307 | H | CH | C | NEt₂ | H | CO | SB | N(CO—nPr)CH₂Ph-4-COOH | H |
| 308 | H | CH | C | OH | H | CO | SB | N(CO—nPr)CH₂Ph-4-COOH | H |
| 309 | H | CH | C | N₂C₄H₉ | H | CO | SB | N(CO—nPen)CH₂Ph-4-COOH | H |
| 310 | H | CH | C | NC₄H₈ | H | CO | SB | N(CO—nPen)CH₂Ph-4-COOH | H |
| 311 | H | CH | C | NEt₂ | H | CO | SB | N(CO—nPen)CH₂Ph-4-COOH | H |
| 312 | H | CH | C | OH | H | CO | SB | N(CO—nPen)CH₂Ph-4-COOH | H |
| 313 | H | CH | C | N₂C₄H₉ | H | CO | SB | N(CO—nHex)CH₂Ph-4-COOH | H |

TABLE 9-continued

| No. | R¹ | A | Z | R² | R⁴ | R⁷ | R⁸ | R¹² | R¹³ |
|-----|----|----|----|-----|-----|-----|-----|------|------|
| 314 | H | CH | C | NC₄H₈ | H | CO | SB | N(CO—nHex)CH₂Ph-4-COOH | H |
| 315 | H | CH | C | NEt₂ | H | CO | SB | N(CO—nHex)CH₂Ph-4-COOH | H |

TABLE 10

| No. | R¹ | A | Z | R² | R⁴ | R⁷ | R⁸ | R¹² | R¹³ |
|-----|----|----|----|-----|-----|-----|-----|------|------|
| 316 | H | CH | C | OH | H | CO | SB | N(CO—nHex)CH₂Ph-4-COOH | H |
| 317 | H | CH | C | NC₄H₈O | H | CO | SB | N(CONH—Me)CH₂Ph-4-COOH | H |
| 318 | H | CH | C | NC₄H₈O | H | CO | SB | N(CONH—Et)CH₂Ph-4-COOH | H |
| 319 | H | CH | C | NC₄H₈O | H | CO | SB | N(CONH—nPr)CH₂Ph-4-COOH | H |
| 320 | H | CH | C | NC₄H₈O | H | CO | SB | N(CONH—nBu)CH₂Ph-4-COOH | H |
| 321 | H | CH | C | NC₄H₈O | H | CO | SB | N(CONH—nPen)CH₂Ph-4-COOH | H |
| 322 | H | CH | C | N₂C₄H₉ | H | CO | SB | N(CONH—Me)CH₂Ph-4-COOH | H |
| 323 | H | CH | C | NC₄H₈ | H | CO | SB | N(CONH—Me)CH₂Ph-4-COOH | H |
| 324 | H | CH | C | NEt₂ | H | CO | SB | N(CONH—Me)CH₂Ph-4-COOH | H |
| 325 | H | CH | C | OH | H | CO | SB | N(CONH—Me)CH₂Ph-4-COOH | H |
| 326 | H | CH | C | N₂C₄H₉ | H | CO | SB | N(CONH—Et)CH₂Ph-4-COOH | H |
| 327 | H | CH | C | NC₄H₈ | H | CO | SB | N(CONH—Et)CH₂Ph-4-COOH | H |
| 328 | H | CH | C | NEt₂ | H | CO | SB | N(CONH—Et)CH₂Ph-4-COOH | H |
| 329 | H | CH | C | OH | H | CO | SB | N(CONH—Et)CH₂Ph-4-COOH | H |
| 330 | H | CH | C | N₂C₄H₉ | H | CO | SB | N(CONH—nPr)CH₂Ph-4-COOH | H |
| 331 | H | CH | C | NC₄H₈ | H | CO | SB | N(CONH—nPr)CH₂Ph-4-COOH | H |
| 332 | H | CH | C | NEt₂ | H | CO | SB | N(CONH—nPr)CH₂Ph-4-COOH | H |
| 333 | H | CH | C | OH | H | CO | SB | N(CONH—nPr)CH₂Ph-4-COOH | H |
| 334 | H | CH | C | N₂C₄H₉ | H | CO | SB | N(CONH—nBu)CH₂Ph-4-COOH | H |
| 335 | H | CH | C | NC₄H₈ | H | CO | SB | N(CONH—nBu)CH₂Ph-4-COOH | H |
| 336 | H | CH | C | NEt₂ | H | CO | SB | N(CONH—nBu)CH₂Ph-4-COOH | H |
| 337 | H | CH | C | OH | H | CO | SB | N(CONH—nBu)CH₂Ph-4-COOH | H |
| 338 | H | CH | C | N₂C₄H₉ | H | CO | SB | N(CONH—nPen)CH₂Ph-4-COOH | H |
| 339 | H | CH | C | NC₄H₈ | H | CO | SB | N(CONH—nPen)CH₂Ph-4-COOH | H |
| 340 | H | CH | C | NEt₂ | H | CO | SB | N(CONH—nPen)CH₂Ph-4-COOH | H |
| 341 | H | CH | C | OH | H | CO | SB | N(CONH—nPen)CH₂Ph-4-COOH | H |
| 342 | H | CH | C | NC₄H₈O | H | CO | SB | N(Me)CH₂Ph-4-COOH | H |
| 343 | H | CH | C | NC₄H₈O | H | CO | SB | N(Et)CH₂Ph-4-COOH | H |
| 344 | H | CH | C | NC₄H₈O | H | CO | SB | N(nPr)CH₂Ph-4-COOH | H |
| 345 | H | CH | C | NC₄H₈O | H | CO | SB | N(nBu)CH₂Ph-4-COOH | H |
| 346 | H | CH | C | NC₄H₈O | H | CO | SB | N(nPen)CH₂Ph-4-COOH | H |
| 347 | H | CH | C | NC₄H₈O | H | CO | SB | N(nHex)CH₂Ph-4-COOH | H |
| 348 | H | CH | C | N₂C₄H₉ | H | CO | SB | N(Me)CH₂Ph-4-COOH | H |
| 349 | H | CH | C | NC₄H₈ | H | CO | SB | N(Me)CH₂Ph-4-COOH | H |
| 350 | H | CH | C | NEt₂ | H | CO | SB | N(Me)CH₂Ph-4-COOH | H |

TABLE 11

| No. | R¹ | A | Z | R² | R⁴ | R⁷ | R⁸ | R¹² | R¹³ |
|-----|----|----|----|-----|-----|-----|-----|------|------|
| 351 | H | CH | C | OH | H | CO | SB | N(Me)CH₂Ph-4-COOH | H |
| 352 | H | CH | C | N₂C₄H₉ | H | CO | SB | N(Et)CH₂Ph-4-COOH | H |
| 353 | H | CH | C | NC₄H₈ | H | CO | SB | N(Et)CH₂Ph-4-COOH | H |
| 354 | H | CH | C | NEt₂ | H | CO | SB | N(Et)CH₂Ph-4-COOH | H |
| 355 | H | CH | C | OH | H | CO | SB | N(Et)CH₂Ph-4-COOH | H |
| 356 | H | CH | C | N₂C₄H₉ | H | CO | SB | N(nPr)CH₂Ph-4-COOH | H |
| 357 | H | CH | C | NC₄H₈ | H | CO | SB | N(nPr)CH₂Ph-4-COOH | H |
| 358 | H | CH | C | NEt₂ | H | CO | SB | N(nPr)CH₂Ph-4-COOH | H |
| 359 | H | CH | C | OH | H | CO | SB | N(nPr)CH₂Ph-4-COOH | H |
| 360 | H | CH | C | N₂C₄H₉ | H | CO | SB | N(nBu)CH₂Ph-4-COOH | H |
| 361 | H | CH | C | NC₄H₈ | H | CO | SB | N(nBu)CH₂Ph-4-COOH | H |
| 362 | H | CH | C | NEt₂ | H | CO | SB | N(nBu)CH₂Ph-4-COOH | H |
| 363 | H | CH | C | OH | H | CO | SB | N(nBu)CH₂Ph-4-COOH | H |
| 364 | H | CH | C | N₂C₄H₉ | H | CO | SB | N(nPen)CH₂Ph-4-COOH | H |
| 365 | H | CH | C | NC₄H₈ | H | CO | SB | N(nPen)CH₂Ph-4-COOH | H |
| 366 | H | CH | C | NEt₂ | H | CO | SB | N(nPen)CH₂Ph-4-COOH | H |
| 367 | H | CH | C | OH | H | CO | SB | N(nPen)CH₂Ph-4-COOH | H |
| 368 | H | CH | C | N₂C₄H₉ | H | CO | SB | N(nHex)CH₂Ph-4-COOH | H |
| 369 | H | CH | C | NC₄H₈ | H | CO | SB | N(nHex)CH₂Ph-4-COOH | H |
| 370 | H | CH | C | NEt₂ | H | CO | SB | N(nHex)CH₂Ph-4-COOH | H |
| 371 | H | CH | C | OH | H | CO | SB | N(nHex)CH₂Ph-4-COOH | H |
| 372 | Me | CH | C | NC₄H₈O | Me | CO | SB | N(CO—nBu)CH₂Ph-4-COOH | H |
| 373 | Me | CH | C | NC₃H₆ | Me | CO | SB | N(CO—nBu)CH₂Ph-4-COOH | H |
| 374 | Me | CH | C | NC₄H₈ | Me | CO | SB | N(CO—nBu)CH₂Ph-4-COOH | H |
| 375 | Me | CH | C | NC₅H₁₀ | Me | CO | SB | N(CO—nBu)CH₂Ph-4-COOH | H |

TABLE 11-continued

| No. | R¹ | A | Z | R² | R⁴ | R⁷ | R⁸ | R¹² | R¹³ |
|---|---|---|---|---|---|---|---|---|---|
| 376 | Me | CH | C | NC₄H₈S | Me | CO | SB | N(CO—nBu)CH₂Ph-4-COOH | H |
| 377 | Me | CH | C | N₂C₄H₉ | Me | CO | SB | N(CO—nBu)CH₂Ph-4-COOH | H |
| 378 | Me | CH | C | NH₂ | Me | CO | SB | N(CO—nBu)CH₂Ph-4-COOH | H |
| 379 | Me | CH | C | NHMe | Me | CO | SB | N(CO—nBu)CH₂Ph-4-COOH | H |
| 380 | Me | CH | C | NHEt | Me | CO | SB | N(CO—nBu)CH₂Ph-4-COOH | H |
| 381 | Me | CH | C | NMe₂ | Me | CO | SB | N(CO—nBu)CH₂Ph-4-COOH | H |
| 382 | Me | CH | C | NEt₂ | Me | CO | SB | N(CO—nBu)CH₂Ph-4-COOH | H |
| 383 | Me | CH | C | OH | Me | CO | SB | N(CO—nBu)CH₂Ph-4-COOH | H |
| 384 | Me | CH | C | OMe | Me | CO | SB | N(CO—nBu)CH₂Ph-4-COOH | H |
| 385 | Me | CH | C | OEt | Me | CO | SB | N(CO—nBu)CH₂Ph-4-COOH | H |

TABLE 12

| No. | R¹ | A | Z | R² | R⁴ | R⁷ | R⁸ | R¹² | R¹³ |
|---|---|---|---|---|---|---|---|---|---|
| 386 | Me | CH | C | NC₄H₈O | Me | CO | SB | N(CO—Me)CH₂Ph-4-COOH | H |
| 387 | Me | CH | C | NC₄H₈O | Me | CO | SB | N(CO—Et)CH₂Ph-4-COOH | H |
| 388 | Me | CH | C | NC₄H₈O | Me | CO | SB | N(CO—nPr)CH₂Ph-4-COOH | H |
| 389 | Me | CH | C | NC₄H₈O | Me | CO | SB | N(CO—nPen)CH₂Ph-4-COOH | H |
| 390 | Me | CH | C | NC₄H₈O | Me | CO | SB | N(CO—nHex)CH₂Ph-4-COOH | H |
| 391 | Me | CH | C | N₂C₄H₉ | Me | CO | SB | N(CO—Me)CH₂Ph-4-COOH | H |
| 392 | Me | CH | C | NC₄H₈ | Me | CO | SB | N(CO—Me)CH₂Ph-4-COOH | H |
| 393 | Me | CH | C | NEt₂ | Me | CO | SB | N(CO—Me)CH₂Ph-4-COOH | H |
| 394 | Me | CH | C | OH | Me | CO | SB | N(CO—Me)CH₂Ph-4-COOH | H |
| 395 | Me | CH | C | N₂C₄H₉ | Me | CO | SB | N(CO—Et)CH₂Ph-4-COOH | H |
| 396 | Me | CH | C | NC₄H₈ | Me | CO | SB | N(CO—Et)CH₂Ph-4-COOH | H |
| 397 | Me | CH | C | NEt₂ | Me | CO | SB | N(CO—Et)CH₂Ph-4-COOH | H |
| 398 | Me | CH | C | OH | Me | CO | SB | N(CO—Et)CH₂Ph-4-COOH | H |
| 399 | Me | CH | C | N₂C₄H₉ | Me | CO | SB | N(CO—nPr)CH₂Ph-4-COOH | H |
| 400 | Me | CH | C | NC₄H₈ | Me | CO | SB | N(CO—nPr)CH₂Ph-4-COOH | H |
| 401 | Me | CH | C | NEt₂ | Me | CO | SB | N(CO—nPr)CH₂Ph-4-COOH | H |
| 402 | Me | CH | C | OH | Me | CO | SB | N(CO—nPr)CH₂Ph-4-COOH | H |
| 403 | Me | CH | C | N₂C₄H₉ | Me | CO | SB | N(CO—nPen)CH₂Ph-4-COOH | H |
| 404 | Me | CH | C | NC₄H₈ | Me | CO | SB | N(CO—nPen)CH₂Ph-4-COOH | H |
| 405 | Me | CH | C | NEt₂ | Me | CO | SB | N(CO—nPen)CH₂Ph-4-COOH | H |
| 406 | Me | CH | C | OH | Me | CO | SB | N(CO—nPen)CH₂Ph-4-COOH | H |
| 407 | Me | CH | C | N₂C₄H₉ | Me | CO | SB | N(CO—nHex)CH₂Ph-4-COOH | H |
| 408 | Me | CH | C | NC₄H₈ | Me | CO | SB | N(CO—nHex)CH₂Ph-4-COOH | H |
| 409 | Me | CH | C | NEt₂ | Me | CO | SB | N(CO—nHex)CH₂Ph-4-COOH | H |
| 410 | Me | CH | C | OH | Me | CO | SB | N(CO—nHex)CH₂Ph-4-COOH | H |
| 411 | Me | CH | C | NC₄H₈O | Me | CO | SB | N(CONH—Me)CH₂Ph-4-COOH | H |
| 412 | Me | CH | C | NC₄H₈O | Me | CO | SB | N(CONH—Et)CH₂Ph-4-COOH | H |
| 413 | Me | CH | C | NC₄H₈O | Me | CO | SB | N(CONH—nPr)CH₂Ph-4-COOH | H |
| 414 | Me | CH | C | NC₄H₈O | Me | CO | SB | N(CONH—nBu)CH₂Ph-4-COOH | H |
| 415 | Me | CH | C | NC₄H₈O | Me | CO | SB | N(CONH—nPen)CH₂Ph-4-COOH | H |
| 416 | Me | CH | C | N₂C₄H₉ | Me | CO | SB | N(CONH—Me)CH₂Ph-4-COOH | H |
| 417 | Me | CH | C | NC₄H₈ | Me | CO | SB | N(CONH—Me)CH₂Ph-4-COOH | H |
| 418 | Me | CH | C | NEt₂ | Me | CO | SB | N(CONH—Me)CH₂Ph-4-COOH | H |
| 419 | Me | CH | C | OH | Me | CO | SB | N(CONH—Me)CH₂Ph-4-COOH | H |
| 420 | Me | CH | C | N₂C₄H₉ | Me | CO | SB | N(CONH—Et)CH₂Ph-4-COOH | H |

TABLE 13

| No. | R¹ | A | Z | R² | R⁴ | R⁷ | R⁸ | R¹² | R¹³ |
|---|---|---|---|---|---|---|---|---|---|
| 421 | Me | CH | C | NC₄H₈ | Me | CO | SB | N(CONH—Et)CH₂Ph-4-COOH | H |
| 422 | Me | CH | C | NEt₂ | Me | CO | SB | N(CONH—Et)CH₂Ph-4-COOH | H |
| 423 | Me | CH | C | OH | Me | CO | SB | N(CONH—Et)CH₂Ph-4-COOH | H |
| 424 | Me | CH | C | N₂C₄H₉ | Me | CO | SB | N(CONH—nPr)CH₂Ph-4-COOH | H |
| 425 | Me | CH | C | NC₄H₈ | Me | CO | SB | N(CONH—nPr)CH₂Ph-4-COOH | H |
| 426 | Me | CH | C | NEt₂ | Me | CO | SB | N(CONH—nPr)CH₂Ph-4-COOH | H |
| 427 | Me | CH | C | OH | Me | CO | SB | N(CONH—nPr)CH₂Ph-4-COOH | H |
| 428 | Me | CH | C | N₂C₄H₉ | Me | CO | SB | N(CONH—nBu)CH₂Ph-4-COOH | H |
| 429 | Me | CH | C | NC₄H₈ | Me | CO | SB | N(CONH—nBu)CH₂Ph-4-COOH | H |
| 430 | Me | CH | C | NEt₂ | Me | CO | SB | N(CONH—nBu)CH₂Ph-4-COOH | H |
| 431 | Me | CH | C | OH | Me | CO | SB | N(CONH—nBu)CH₂Ph-4-COOH | H |
| 432 | Me | CH | C | N₂C₄H₉ | Me | CO | SB | N(CONH—nPen)CH₂Ph-4-COOH | H |
| 433 | Me | CH | C | NC₄H₈ | Me | CO | SB | N(CONH—nPen)CH₂Ph-4-COOH | H |
| 434 | Me | CH | C | NEt₂ | Me | CO | SB | N(CONH—nPen)CH₂Ph-4-COOH | H |
| 435 | Me | CH | C | OH | Me | CO | SB | N(CONH—nPen)CH₂Ph-4-COOH | H |
| 436 | Me | CH | C | NC₄H₈O | Me | CO | SB | N(Me)CH₂Ph-4-COOH | H |
| 437 | Me | CH | C | NC₄H₈O | Me | CO | SB | N(Et)CH₂Ph-4-COOH | H |

TABLE 13-continued

| No. | R¹ | A | Z | R² | R⁴ | R⁷ | R⁸ | R¹² | R¹³ |
|---|---|---|---|---|---|---|---|---|---|
| 438 | Me | CH | C | NC₄H₈O | Me | CO | SB | N(nPr)CH₂Ph-4-COOH | H |
| 439 | Me | CH | C | NC₄H₈O | Me | CO | SB | N(nBu)CH₂Ph-4-COOH | H |
| 440 | Me | CH | C | NC₄H₈O | Me | CO | SB | N(nPen)CH₂Ph-4-COOH | H |
| 441 | Me | CH | C | NC₄H₈O | Me | CO | SB | N(nHex)CH₂Ph-4-COOH | H |
| 442 | Me | CH | C | N₂C₄H₉ | Me | CO | SB | N(Me)CH₂Ph-4-COOH | H |
| 443 | Me | CH | C | NC₄H₈ | Me | CO | SB | N(Me)CH₂Ph-4-COOH | H |
| 444 | Me | CH | C | NEt₂ | Me | CO | SB | N(Me)CH₂Ph-4-COOH | H |
| 445 | Me | CH | C | OH | Me | CO | SB | N(Me)CH₂Ph-4-COOH | H |
| 446 | Me | CH | C | N₂C₄H₉ | Me | CO | SB | N(Et)CH₂Ph-4-COOH | H |
| 447 | Me | CH | C | NC₄H₈ | Me | CO | SB | N(Et)CH₂Ph-4-COOH | H |
| 448 | Me | CH | C | NEt₂ | Me | CO | SB | N(Et)CH₂Ph-4-COOH | H |
| 449 | Me | CH | C | OH | Me | CO | SB | N(Et)CH₂Ph-4-COOH | H |
| 450 | Me | CH | C | N₂C₄H₉ | Me | CO | SB | N(nPr)CH₂Ph-4-COOH | H |
| 451 | Me | CH | C | NC₄H₈ | Me | CO | SB | N(nPr)CH₂Ph-4-COOH | H |
| 452 | Me | CH | C | NEt₂ | Me | CO | SB | N(nPr)CH₂Ph-4-COOH | H |
| 453 | Me | CH | C | OH | Me | CO | SB | N(nPr)CH₂Ph-4-COOH | H |
| 454 | Me | CH | C | N₂C₄H₉ | Me | CO | SB | N(nBu)CH₂Ph-4-COOH | H |
| 455 | Me | CH | C | NC₄H₈ | Me | CO | SB | N(nBu)CH₂Ph-4-COOH | H |

TABLE 14

| No. | R¹ | A | Z | R² | R⁴ | R⁷ | R⁸ | R¹² | R¹³ |
|---|---|---|---|---|---|---|---|---|---|
| 456 | Me | CH | C | NEt₂ | Me | CO | SB | N(nBu)CH₂Ph-4-COOH | H |
| 457 | Me | CH | C | OH | Me | CO | SB | N(nBu)CH₂Ph-4-COOH | H |
| 458 | Me | CH | C | N₂C₄H₉ | Me | CO | SB | N(nPen)CH₂Ph-4-COOH | H |
| 459 | Me | CH | C | NC₄H₈ | Me | CO | SB | N(nPen)CH₂Ph-4-COOH | H |
| 460 | Me | CH | C | NEt₂ | Me | CO | SB | N(nPen)CH₂Ph-4-COOH | H |
| 461 | Me | CH | C | OH | Me | CO | SB | N(nPen)CH₂Ph-4-COOH | H |
| 462 | Me | CH | C | N₂C₄H₉ | Me | CO | SB | N(nHex)CH₂Ph-4-COOH | H |
| 463 | Me | CH | C | NC₄H₈ | Me | CO | SB | N(nHex)CH₂Ph-4-COOH | H |
| 464 | Me | CH | C | NEt₂ | Me | CO | SB | N(nHex)CH₂Ph-4-COOH | H |
| 465 | Me | CH | C | OH | Me | CO | SB | N(nHex)CH₂Ph-4-COOH | H |
| 466 | Me | CH | C | OMe | Me | CO | SB | N(nHex)CH₂Ph-4-COOH | H |
| 467 | — | — | N | NC₄H₈O | — | CO | — | N(CO-nBu)CH₂Ph-4-COOH | H |
| 468 | — | — | N | NC₃H₆ | — | CO | — | N(CO-nBu)CH₂Ph-4-COOH | H |
| 469 | — | — | N | NC₄H₈ | — | CO | — | N(CO-nBu)CH₂Ph-4-COOH | H |
| 470 | — | — | N | NC₅H₁₀ | — | CO | — | N(CO-nBu)CH₂Ph-4-COOH | H |
| 471 | — | — | N | NC₄H₈S | — | CO | — | N(CO-nBu)CH₂Ph-4-COOH | H |
| 472 | — | — | N | N₂C₄H₉ | — | CO | — | N(CO-nBu)CH₂Ph-4-COOH | H |
| 473 | — | — | N | NH₂ | — | CO | — | N(CO-nBu)CH₂Ph-4-COOH | H |
| 474 | — | — | N | NHMe | — | CO | — | N(CO-nBu)CH₂Ph-4-COOH | H |
| 475 | — | — | N | NHEt | — | CO | — | N(CO-nBu)CH₂Ph-4-COOH | H |
| 476 | — | — | N | NMe₂ | — | CO | — | N(CO-nBu)CH₂Ph-4-COOH | H |
| 477 | — | — | N | NEt₂ | — | CO | — | N(CO-nBu)CH₂Ph-4-COOH | H |
| 478 | — | — | N | OH | — | CO | — | N(CO-nBu)CH₂Ph-4-COOH | H |
| 479 | — | — | N | OMe | — | CO | — | N(CO-nBu)CH₂Ph-4-COOH | H |
| 480 | — | — | N | OEt | — | CO | — | N(CO-nBu)CH₂Ph-4-COOH | H |
| 481 | — | — | N | NC₄H₈O | — | CO | — | N(CO-Me)CH₂Ph-4-COOH | H |
| 482 | — | — | N | NC₄H₈O | — | CO | — | N(CO-Et)CH₂Ph-4-COOH | H |
| 483 | — | — | N | NC₄H₈O | — | CO | — | N(CO-nPr)CH₂Ph-4-COOH | H |
| 484 | — | — | N | NC₄H₈O | — | CO | — | N(CO-nPen)CH₂Ph-4-COOH | H |
| 485 | — | — | N | NC₄H₈O | — | CO | — | N(CO-nHex)CH₂Ph-4-COOH | H |
| 486 | — | — | N | N₂C₄H₉ | — | CO | — | N(CO-Me)CH₂Ph-4-COOH | H |
| 487 | — | — | N | NC₄H₈O | — | CO | — | N(CO-Me)CH₂Ph-4-COOH | H |
| 488 | — | — | N | NEt₂ | — | CO | — | N(CO-Me)CH₂Ph-4-COOH | H |
| 489 | — | — | N | OH | — | CO | — | N(CO-Me)CH₂Ph-4-COOH | H |
| 490 | — | — | N | N₂C₄H₉ | — | CO | — | N(CO-Et)CH₂Ph-4-COOH | H |

TABLE 15

| No. | R¹ | A | Z | R² | R⁴ | R⁷ | R⁸ | R¹² | R¹³ |
|---|---|---|---|---|---|---|---|---|---|
| 491 | — | — | N | NC₄H₈ | — | CO | — | N(CO—Et)CH₂Ph-4-COOH | H |
| 492 | — | — | N | NEt₂ | — | CO | — | N(CO—Et)CH₂Ph-4-COOH | H |
| 493 | — | — | N | OH | — | CO | — | N(CO—Et)CH₂Ph-4-COOH | H |
| 494 | — | — | N | N₂C₄H₉ | — | CO | — | N(CO—nPr)CH₂Ph-4-COOH | H |
| 495 | — | — | N | NC₄H₈ | — | CO | — | N(CO—nPr)CH₂Ph-4-COOH | H |
| 496 | — | — | N | NEt₂ | — | CO | — | N(CO—nPr)CH₂Ph-4-COOH | H |
| 497 | — | — | N | OH | — | CO | — | N(CO—nPr)CH₂Ph-4-COOH | H |
| 498 | — | — | N | N₂C₄H₉ | — | CO | — | N(CO—nPen)CH₂Ph-4-COOH | H |
| 499 | — | — | N | NC₄H₈ | — | CO | — | N(CO—nPen)CH₂Ph-4-COOH | H |

TABLE 15-continued

| No. | R¹ | A | Z | R² | R⁴ | R⁷ | R⁸ | R¹² | R¹³ |
|---|---|---|---|---|---|---|---|---|---|
| 500 | — | — | N | NEt₂ | — | CO | — | N(CO—nPen)CH₂Ph-4-COOH | H |
| 501 | — | — | N | OH | — | CO | — | N(CO—nPen)CH₂Ph-4-COOH | H |
| 502 | — | — | N | N₂C₄H₉ | — | CO | — | N(CO—nHex)CH₂Ph-4-COOH | H |
| 503 | — | — | N | NC₄H₈ | — | CO | — | N(CO—nHex)CH₂Ph-4-COOH | H |
| 504 | — | — | N | NEt₂ | — | CO | — | N(CO—nHex)CH₂Ph-4-COOH | H |
| 505 | — | — | N | OH | — | CO | — | N(CO—nHex)CH₂Ph-4-COOH | H |
| 506 | — | — | N | NC₄H₈O | — | CO | — | N(CONH—Me)CH₂Ph-4-COOH | H |
| 507 | — | — | N | NC₄H₈O | — | CO | — | N(CONH—Et)CH₂Ph-4-COOH | H |
| 508 | — | — | N | NC₄H₈O | — | CO | — | N(CONH—nPr)CH₂Ph-4-COOH | H |
| 509 | — | — | N | NC₄H₈O | — | CO | — | N(CONH—nBu)CH₂Ph-4-COOH | H |
| 510 | — | — | N | NC₄H₈O | — | CO | — | N(CONH—nPen)CH₂Ph-4-COOH | H |
| 511 | — | — | N | N₂C₄H₉ | — | CO | — | N(CONH—Me)CH₂Ph-4-COOH | H |
| 512 | — | — | N | NC₄H₈ | — | CO | — | N(CONH—Me)CH₂Ph-4-COOH | H |
| 513 | — | — | N | NEt₂ | — | CO | — | N(CONH—Me)CH₂Ph-4-COOH | H |
| 514 | — | — | N | OH | — | CO | — | N(CONH—Me)CH₂Ph-4-COOH | H |
| 515 | — | — | N | N₂C₄H₉ | — | CO | — | N(CONH—Et)CH₂Ph-4-COOH | H |
| 516 | — | — | N | NC₄H₈ | — | CO | — | N(CONH—Et)CH₂Ph-4-COOH | H |
| 517 | — | — | N | NEt₂ | — | CO | — | N(CONH—Et)CH₂Ph-4-COOH | H |
| 518 | — | — | N | OH | — | CO | — | N(CONH—Et)CH₂Ph-4-COOH | H |
| 519 | — | — | N | N₂C₄H₉ | — | CO | — | N(CONH—nPr)CH₂Ph-4-COOH | H |
| 520 | — | — | N | NC₄H₈ | — | CO | — | N(CONH—nPr)CH₂Ph-4-COOH | H |
| 521 | — | — | N | NEt₂ | — | CO | — | N(CONH—nPr)CH₂Ph-4-COOH | H |
| 522 | — | — | N | OH | — | CO | — | N(CONH—nPr)CH₂Ph-4-COOH | H |
| 523 | — | — | N | N₂C₄H₉ | — | CO | — | N(CONH—nBu)CH₂Ph-4-COOH | H |
| 524 | — | — | N | NC₄H₈ | — | CO | — | N(CONH—nBu)CH₂Ph-4-COOH | H |
| 525 | — | — | N | NEt₂ | — | CO | — | N(CONH—nBu)CH₂Ph-4-COOH | H |

TABLE 16

| No. | R¹ | A | Z | R² | R⁴ | R⁷ | R⁸ | R¹² | R¹³ |
|---|---|---|---|---|---|---|---|---|---|
| 526 | — | — | N | OH | — | CO | — | N(CONH—nBu)CH₂Ph-4-COOH | H |
| 527 | — | — | N | N₂C₄H₉ | — | CO | — | N(CONH—nPen)CH₂Ph-4-COOH | H |
| 528 | — | — | N | NC₄H₈ | — | CO | — | N(CONH—nPen)CH₂Ph-4-COOH | H |
| 529 | — | — | N | NEt₂ | — | CO | — | N(CONH—nPen)CH₂Ph-4-COOH | H |
| 530 | — | — | N | OH | — | CO | — | N(CONH—nPen)CH₂Ph-4-COOH | H |
| 531 | — | — | N | NC₄H₈O | — | CO | — | N(Me)CH₂Ph-4-COOH | H |
| 532 | — | — | N | NC₄H₈O | — | CO | — | N(Et)CH₂Ph-4-COOH | H |
| 533 | — | — | N | NC₄H₈O | — | CO | — | N(nPr)CH₂Ph-4-COOH | H |
| 534 | — | — | N | NC₄H₈O | — | CO | — | N(nBu)CH₂Ph-4-COOH | H |
| 535 | — | — | N | NC₄H₈O | — | CO | — | N(nPen)CH₂Ph-4-COOH | H |
| 536 | — | — | N | NC₄H₈O | — | CO | — | N(nHex)CH₂Ph-4-COOH | H |
| 537 | — | — | N | N₂C₄H₉ | — | CO | — | N(Me)CH₂Ph-4-COOH | H |
| 538 | — | — | N | NC₄H₈ | — | CO | — | N(Me)CH₂Ph-4-COOH | H |
| 539 | — | — | N | NEt₂ | — | CO | — | N(Me)CH₂Ph-4-COOH | H |
| 540 | — | — | N | OH | — | CO | — | N(Me)CH₂Ph-4-COOH | H |
| 541 | — | — | N | N₂C₄H₉ | — | CO | — | N(Et)CH₂Ph-4-COOH | H |
| 542 | — | — | N | NC₄H₈ | — | CO | — | N(Et)CH₂Ph-4-COOH | H |
| 543 | — | — | N | NEt₂ | — | CO | — | N(Et)CH₂Ph-4-COOH | H |
| 544 | — | — | N | OH | — | CO | — | N(Et)CH₂Ph-4-COOH | H |
| 545 | — | — | N | N₂C₄H₉ | — | CO | — | N(nPr)CH₂Ph-4-COOH | H |
| 546 | — | — | N | NC₄H₈ | — | CO | — | N(nPr)CH₂Ph-4-COOH | H |
| 547 | — | — | N | NEt₂ | — | CO | — | N(nPr)CH₂Ph-4-COOH | H |
| 548 | — | — | N | OH | — | CO | — | N(nPr)CH₂Ph-4-COOH | H |
| 549 | — | — | N | N₂C₄H₉ | — | CO | — | N(nBu)CH₂Ph-4-COOH | H |
| 550 | — | — | N | NC₄H₈ | — | CO | — | N(nBu)CH₂Ph-4-COOH | H |
| 551 | — | — | N | NEt₂ | — | CO | — | N(nBu)CH₂Ph-4-COOH | H |
| 552 | — | — | N | OH | — | CO | — | N(nBu)CH₂Ph-4-COOH | H |
| 553 | — | — | N | N₂C₄H₉ | — | CO | — | N(nPen)CH₂Ph-4-COOH | H |
| 554 | — | — | N | NC₄H₈ | — | CO | — | N(nPen)CH₂Ph-4-COOH | H |
| 555 | — | — | N | NEt₂ | — | CO | — | N(nPen)CH₂Ph-4-COOH | H |
| 556 | — | — | N | OH | — | CO | — | N(nPen)CH₂Ph-4-COOH | H |
| 557 | — | — | N | N₂C₄H₉ | — | CO | — | N(nHex)CH₂Ph-4-COOH | H |
| 558 | — | — | N | NC₄H₈ | — | CO | — | N(nHex)CH₂Ph-4-COOH | H |
| 559 | — | — | N | NEt₂ | — | CO | — | N(nHex)CH₂Ph-4-COOH | H |
| 560 | — | — | N | OH | — | CO | — | N(nHex)CH₂Ph-4-COOH | H |

TABLE 17

| No. | R¹ | A | Z | R² | R⁴ | R⁷ | R⁸ | R¹² | R¹³ |
|---|---|---|---|---|---|---|---|---|---|
| 561 | Me | N | C | NC₄H₈O | Me | CO | SB | N(CO—nBu)CH₂Ph-4-COOH | CF₃ |
| 562 | Me | N | C | NC₄H₈O | Me | CO | SB | N(CO—nBu)CH₂Ph-4-COOH | Ph |
| 563 | Me | N | C | NC₄H₈O | Me | CO | SB | N(CO—nBu)CH₂Ph-4-COOH | CH₂Ph |
| 564 | Me | N | C | NC₄H₈O | Me | CO | SB | N(CO—nBu)CH₂Ph-4-COOH | (CH₂)₂Ph |
| 565 | Me | N | C | NC₄H₈O | Me | CO | SB | N(CO—nBu)CH₂Ph-4-COOH | NHCOCH₂Ph |
| 566 | Me | N | C | NC₄H₈O | Me | CO | SB | N(CO—nBu)CH₂Ph-4-COOH | NHCO(CH₂)₂Ph |
| 567 | Me | N | C | NC₄H₈O | Me | CO | SB | N(CO—nBu)CH₂Ph-4-COOH | NHCOCHPh₂ |
| 568 | Me | N | C | NC₄H₈O | Me | CO | SB | N(CO—nBu)CH₂Ph-4-COOH | CH₃ |
| 569 | — | — | CH | NC₄H₈O | — | CO | — | N(CO—nBu)CH₂Ph-4-COOH | CF₃ |
| 570 | — | — | CH | NC₄H₈O | — | CO | — | N(CO—nBu)CH₂Ph-4-COOH | Ph |
| 571 | — | — | CH | NC₄H₈O | — | CO | — | N(CO—nBu)CH₂Ph-4-COOH | CH₂Ph |
| 572 | — | — | CH | NC₄H₈O | — | CO | — | N(CO—nBu)CH₂Ph-4-COOH | (CH₂)₂Ph |
| 573 | — | — | CH | NC₄H₈O | — | CO | — | N(CO—nBu)CH₂Ph-4-COOH | NHCOCH₂Ph |
| 574 | — | — | CH | NC₄H₈O | — | CO | — | N(CO—nBu)CH₂Ph-4-COOH | NHCO(CH₂)₂Ph |
| 575 | — | — | CH | NC₄H₈O | — | CO | — | N(CO—nBu)CH₂Ph-4-COOH | NHCOCHPh₂ |
| 576 | — | — | CH | NC₄H₈O | — | CO | — | N(CO—nBu)CH₂Ph-4-COOH | CH₃ |
| 577 | — | — | N | NC₄H₈O | — | CO | — | N(CO—nBu)CH₂Ph-4-COOH | CF₃ |
| 578 | — | — | N | NC₄H₈O | — | CO | — | N(CO—nBu)CH₂Ph-4-COOH | Ph |
| 579 | — | — | N | NC₄H₈O | — | CO | — | N(CO—nBu)CH₂Ph-4-COOH | CH₂Ph |
| 580 | — | — | N | NC₄H₈O | — | CO | — | N(CO—nBu)CH₂Ph-4-COOH | (CH₂)₂Ph |
| 581 | — | — | N | NC₄H₈O | — | CO | — | N(CO—nBu)CH₂Ph-4-COOH | NHCOCH₂Ph |
| 582 | — | — | N | NC₄H₈O | — | CO | — | N(CO—nBu)CH₂Ph-4-COOH | NHCO(CH₂)₂Ph |
| 583 | — | — | N | NC₄H₈O | — | CO | — | N(CO—nBu)CH₂Ph-4-COOH | NHCOCHPh₂ |
| 584 | — | — | N | NC₄H₈O | — | CO | — | N(CO—nBu)CH₂Ph-4-COOH | CH₃ |
| 585 | nBu | N | C | NC₄H₈O | H | CO | CO | NHCH₂PhPh-2-CN₄H | H |
| 586 | nBu | N | C | NEt₂ | H | CO | CO | NHCH₂PhPh-2-CN₄H | H |
| 587 | nBu | N | C | NC₄H₈O | H | CO | CO | OCH₂PhPh-2-CN₄H | H |
| 588 | nBu | N | C | NEt₂ | H | CO | CO | OCH₂Ph-4-COOH | H |
| 589 | nPen | N | C | NC₄H₈O | Me | CO | SB | OCH₂Ph-4-COOH | H |
| 590 | nPen | N | C | NC₄H₈O | Me | CO | SB | NHCH₂PhPh-2-CN₄H | H |
| 591 | Me | N | C | NC₄H₈O | Me | CO | SB | N(CO—nBu)CH₂PhPh-2-CN₄H | H |
| 592 | Me | N | C | NC₄H₈O | H | CO | CO | N(CO—nBu)CH₂PhPh-2-CN₄H | H |
| 593 | nPen | N | C | NC₄H₈O | Me | CO | SB | NHCH₂PhPh-2-CN₄H | NHCOCHPh₂ |
| 594 | nBu | N | C | NC₄H₈O | H | CO | CO | N(CH₂PhPh-2-CN₄H)₂ | H |
| 595 | nPen | N | C | NC₄H₈O | Me | SO₂ | SB | NHCH₂PhPh-2-CN₄H | H |

TABLE 18

| No. | R¹ | A | Z | R² | R⁴ | R⁷ | R⁸ | R¹² | R¹³ |
|---|---|---|---|---|---|---|---|---|---|
| 596 | nPen | N | C | NC₄H₈O | Me | SO₂ | SB | NHCH₂Ph-4-COOH | H |
| 597 | Me | N | C | NC₄H₈O | Me | SO₂ | SB | N(CO—nBu)CH₂Ph-4-COOH | H |
| 598 | nPen | N | C | NC₄H₈O | Me | SO₂ | SB | NHCH₂Ph-4-COOH | NHCOCHPh₂ |
| 599 | nPen | N | C | NC₄H₈O | Me | SO₂ | SB | NHCH₂PhPh-2-CN₄H | NHCO(CH₂)₂Ph |
| 600 | Me | N | C | NC₄H₈O | Me | CO | SB | N(CO—nBu)CH₂Ph-4-COOMe | H |
| 601 | Me | N | C | NC₄H₈O | Me | CO | SB | N(CO—nBu)CH₂Ph-4-OMe | H |
| 602 | Me | N | C | NC₄H₈O | Me | CO | SB | N(CO—nBu)CH₂Ph-4-OH | H |
| 603 | Me | N | C | NC₄H₈O | Me | CO | SB | N(CO—nBu)CH₂Ph-4-NH₂ | H |
| 604 | Me | N | C | NC₄H₈O | Me | CO | SB | N(CO—nBu)CH₂Ph-4-CN₄H | H |
| 605 | Me | N | C | NC₄H₈O | Me | CO | SB | N(CO—nBu)CH₂Ph-4-SO₃H | H |
| 606 | H | CH | C | NC₄H₈O | H | CO | SB | N(CO—nBu)CH₂Ph-4-COOMe | H |
| 607 | H | CH | C | NC₄H₈O | H | CO | SB | N(CO—nBu)CH₂Ph-4-OMe | H |
| 608 | H | CH | C | NC₄H₈O | H | CO | SB | N(CO—nBu)CH₂Ph-4-OH | H |
| 609 | H | CH | C | NC₄H₈O | H | CO | SB | N(CO—nBu)CH₂Ph-4-NH₂ | H |
| 610 | H | CH | C | NC₄H₈O | H | CO | SB | N(CO—nBu)CH₂Ph-4-CN₄H | H |
| 611 | H | CH | C | NC₄H₈O | H | CO | SB | N(CO—nBu)CH₂Ph-4-SO₃H | H |
| 612 | — | — | CH | NC₄H₈O | — | CO | — | N(CO—nBu)CH₂Ph-4-COOMe | H |
| 613 | — | — | CH | NC₄H₈O | — | CO | — | N(CO—nBu)CH₂Ph-4-OMe | H |
| 614 | — | — | CH | NC₄H₈O | — | CO | — | N(CO—nBu)CH₂Ph-4-OH | H |
| 615 | — | — | CH | NC₄H₈O | — | CO | — | N(CO—nBu)CH₂Ph-4-NH₂ | H |
| 616 | — | — | CH | NC₄H₈O | — | CO | — | N(CO—nBu)CH₂Ph-4-CN₄H | H |
| 617 | — | — | CH | NC₄H₈O | — | CO | — | N(CO—nBu)CH₂Ph-4-SO₃H | H |
| 618 | — | — | N | NC₄H₈O | — | CO | — | N(CO—nBu)CH₂Ph-4-COOMe | H |
| 619 | — | — | N | NC₄H₈O | — | CO | — | N(CO—nBu)CH₂Ph-4-OMe | H |
| 620 | — | — | N | NC₄H₈O | — | CO | — | N(CO—nBu)CH₂Ph-4-OH | H |
| 621 | — | — | N | NC₄H₈O | — | CO | — | N(CO—nBu)CH₂Ph-4-NH₂ | H |
| 622 | — | — | N | NC₄H₈O | — | CO | — | N(CO—nBu)CH₂Ph-4-CN₄H | H |
| 623 | — | — | N | NC₄H₈O | — | CO | — | N(CO—nBu)CH₂Ph-4-SO₃H | H |
| 624 | Et | N | C | NC₄H₈O | Et | CO | SB | N(CO—nBu)CH₂Ph-4-COOH | H |
| 625 | Et | N | C | NC₃H₆ | Et | CO | SB | N(CO—nBu)CH₂Ph-4-COOH | H |
| 626 | Et | N | C | NC₄H₈ | Et | CO | SB | N(CO—nBu)CH₂Ph-4-COOH | H |
| 627 | Et | N | C | NC₅H₁₀ | Et | CO | SB | N(CO—nBu)CH₂Ph-4-COOH | H |
| 628 | Et | N | C | NC₄H₈S | Et | CO | SB | N(CO—nBu)CH₂Ph-4-COOH | H |

TABLE 18-continued

| No. | R¹ | A | Z | R² | R⁴ | R⁷ | R⁸ | R¹² | R¹³ |
|---|---|---|---|---|---|---|---|---|---|
| 629 | Et | N | C | N₂C₄H₉ | Et | CO | SB | N(CO—nBu)CH₂Ph-4-COOH | H |
| 630 | Et | N | C | NH₂ | Et | CO | SB | N(CO—nBu)CH₂Ph-4-COOH | H |

TABLE 19

| No. | R¹ | A | Z | R² | R⁴ | R⁷ | R⁸ | R¹² | R¹³ |
|---|---|---|---|---|---|---|---|---|---|
| 631 | Et | N | C | NHMe | Et | CO | SB | N(CO—nBu)CH₂Ph-4-COOH | H |
| 632 | Et | N | C | NHEt | Et | CO | SB | N(CO—nBu)CH₂Ph-4-COOH | H |
| 633 | Et | N | C | NMe₂ | Et | CO | SB | N(CO—nBu)CH₂Ph-4-COOH | H |
| 634 | Et | N | C | NEt₂ | Et | CO | SB | N(CO—nBu)CH₂Ph-4-COOH | H |
| 635 | Et | N | C | OH | Et | CO | SB | N(CO—nBu)CH₂Ph-4-COOH | H |
| 636 | Et | N | C | OMe | Et | CO | SB | N(CO—nBu)CH₂Ph-4-COOH | H |
| 637 | Et | N | C | OEt | Et | CO | SB | N(CO—nBu)CH₂Ph-4-COOH | H |
| 638 | Et | N | C | NC₄H₈O | Et | CO | SB | N(CO—Me)CH₂Ph-4-COOH | H |
| 639 | Et | N | C | NC₄H₈O | Et | CO | SB | N(CO—Et)CH₂Ph-4-COOH | H |
| 640 | Et | N | C | NC₄H₈O | Et | CO | SB | N(CO—nPr)CH₂Ph-4-COOH | H |
| 641 | Et | N | C | NC₄H₈O | Et | CO | SB | N(CO—nPen)CH₂Ph-4-COOH | H |
| 642 | Et | N | C | NC₄H₈O | Et | CO | SB | N(CO—nHex)CH₂Ph-4-COOH | H |
| 643 | Et | N | C | N₂C₄H₉ | Et | CO | SB | N(CO—Me)CH₂Ph-4-COOH | H |
| 644 | Et | N | C | NC₄H₈ | Et | CO | SB | N(CO—Me)CH₂Ph-4-COOH | H |
| 645 | Et | N | C | NEt₂ | Et | CO | SB | N(CO—Me)CH₂Ph-4-COOH | H |
| 646 | Et | N | C | OH | Et | CO | SB | N(CO—Me)CH₂Ph-4-COOH | H |
| 647 | Et | N | C | N₂C₄H₉ | Et | CO | SB | N(CO—Et)CH₂Ph-4-COOH | H |
| 648 | Et | N | C | NC₄H₈ | Et | CO | SB | N(CO—Et)CH₂Ph-4-COOH | H |
| 649 | Et | N | C | NEt₂ | Et | CO | SB | N(CO—Et)CH₂Ph-4-COOH | H |
| 650 | Et | N | C | OH | Et | CO | SB | N(CO—Et)CH₂Ph-4-COOH | H |
| 651 | Et | N | C | N₂C₄H₉ | Et | CO | SB | N(CO—nPr)CH₂Ph-4-COOH | H |
| 652 | Et | N | C | NC₄H₈ | Et | CO | SB | N(CO—nPr)CH₂Ph-4-COOH | H |
| 653 | Et | N | C | NEt₂ | Et | CO | SB | N(CO—nPr)CH₂Ph-4-COOH | H |
| 654 | Et | N | C | OH | Et | CO | SB | N(CO—nPr)CH₂Ph-4-COOH | H |
| 655 | Et | N | C | N₂C₄H₉ | Et | CO | SB | N(CO—nPen)CH₂Ph-4-COOH | H |
| 656 | Et | N | C | NC₄H₈ | Et | CO | SB | N(CO—nPen)CH₂Ph-4-COOH | H |
| 657 | Et | N | C | NEt₂ | Et | CO | SB | N(CO—nPen)CH₂Ph-4-COOH | H |
| 658 | Et | N | C | OH | Et | CO | SB | N(CO—nPen)CH₂Ph-4-COOH | H |
| 659 | Et | N | C | N₂C₄H₉ | Et | CO | SB | N(CO—nHex)CH₂Ph-4-COOH | H |
| 660 | Et | N | C | NC₄H₈ | Et | CO | SB | N(CO—nHex)CH₂Ph-4-COOH | H |
| 661 | Et | N | C | NEt₂ | Et | CO | SB | N(CO—nHex)CH₂Ph-4-COOH | H |
| 662 | Et | N | C | OH | Et | CO | SB | N(CO—nHex)CH₂Ph-4-COOH | H |
| 663 | Et | N | C | NC₄H₈O | Et | CO | SB | N(CONH—Me)CH₂Ph-4-COOH | H |
| 664 | Et | N | C | NC₄H₈O | Et | CO | SB | N(CONH—Et)CH₂Ph-4-COOH | H |
| 665 | Et | N | C | NC₄H₈O | Et | CO | SB | N(CONH—nPr)CH₂Ph-4-COOH | H |

TABLE 20

| No. | R¹ | A | Z | R² | R⁴ | R⁷ | R⁸ | R¹² | R¹³ |
|---|---|---|---|---|---|---|---|---|---|
| 666 | Et | N | C | NC₄H₈O | Et | CO | SB | N(CONH—nBu)CH₂Ph-4-COOH | H |
| 667 | Et | N | C | NC₄H₈O | Et | CO | SB | N(CONH—nPen)CH₂Ph-4-COOH | H |
| 668 | Et | N | C | N₂C₄H₉ | Et | CO | SB | N(CONH—Me)CH₂Ph-4-COOH | H |
| 669 | Et | N | C | NC₄H₈ | Et | CO | SB | N(CONH—Me)CH₂Ph-4-COOH | H |
| 670 | Et | N | C | NEt₂ | Et | CO | SB | N(CONH—Me)CH₂Ph-4-COOH | H |
| 671 | Et | N | C | OH | Et | CO | SB | N(CONH—Me)CH₂Ph-4-COOH | H |
| 672 | Et | N | C | N₂C₄H₉ | Et | CO | SB | N(CONH—Et)CH₂Ph-4-COOH | H |
| 673 | Et | N | C | NC₄H₈ | Et | CO | SB | N(CONH—Et)CH₂Ph-4-COOH | H |
| 674 | Et | N | C | NEt₂ | Et | CO | SB | N(CONH—Et)CH₂Ph-4-COOH | H |
| 675 | Et | N | C | OH | Et | CO | SB | N(CONH—Et)CH₂Ph-4-COOH | H |
| 676 | Et | N | C | N₂C₄H₉ | Et | CO | SB | N(CONH—nPr)CH₂Ph-4-COOH | H |
| 677 | Et | N | C | NC₄H₈ | Et | CO | SB | N(CONH—nPr)CH₂Ph-4-COOH | H |
| 678 | Et | N | C | NEt₂ | Et | CO | SB | N(CONH—nPr)CH₂Ph-4-COOH | H |
| 679 | Et | N | C | OH | Et | CO | SB | N(CONH—nPr)CH₂Ph-4-COOH | H |
| 680 | Et | N | C | N₂C₄H₉ | Et | CO | SB | N(CONH—nBu)CH₂Ph-4-COOH | H |
| 681 | Et | N | C | NC₄H₈ | Et | CO | SB | N(CONH—nBu)CH₂Ph-4-COOH | H |
| 682 | Et | N | C | NEt₂ | Et | CO | SB | N(CONH—nBu)CH₂Ph-4-COOH | H |
| 683 | Et | N | C | OH | Et | CO | SB | N(CONH—nBu)CH₂Ph-4-COOH | H |
| 684 | Et | N | C | N₂C₄H₉ | Et | CO | SB | N(CONH—nPen)CH₂Ph-4-COOH | H |
| 685 | Et | N | C | NC₄H₈ | Et | CO | SB | N(CONH—nPen)CH₂Ph-4-COOH | H |
| 686 | Et | N | C | NEt₂ | Et | CO | SB | N(CONH—nPen)CH₂Ph-4-COOH | H |
| 687 | Et | N | C | OH | Et | CO | SB | N(CONH—nPen)CH₂Ph-4-COOH | H |
| 688 | Et | N | C | NC₄H₈O | Et | CO | SB | N(Me)CH₂Ph-4-COOH | H |
| 689 | Et | N | C | NC₄H₈O | Et | CO | SB | N(Et)CH₂Ph-4-COOH | H |
| 690 | Et | N | C | NC₄H₈O | Et | CO | SB | N(nPr)CH₂Ph-4-COOH | H |

TABLE 20-continued

| No. | R¹ | A | Z | R² | R⁴ | R⁷ | R⁸ | R¹² | R¹³ |
|-----|----|----|----|------|----|----|----|------|-----|
| 691 | Et | N | C | NC₄H₈O | Et | CO | SB | N(nBu)CH₂Ph-4-COOH | H |
| 692 | Et | N | C | NC₄H₈O | Et | CO | SB | N(nPen)CH₂Ph-4-COOH | H |
| 693 | Et | N | C | NC₄H₈O | Et | CO | SB | N(nHex)CH₂Ph-4-COOH | H |
| 694 | Et | N | C | N₂C₄H₉ | Et | CO | SB | N(Me)CH₂Ph-4-COOH | H |
| 695 | Et | N | C | NC₄H₈ | Et | CO | SB | N(Me)CH₂Ph-4-COOH | H |
| 696 | Et | N | C | NEt₂ | Et | CO | SB | N(Me)CH₂Ph-4-COOH | H |
| 697 | Et | N | C | OH | Et | CO | SB | N(Me)CH₂Ph-4-COOH | H |
| 698 | Et | N | C | N₂C₄H₉ | Et | CO | SB | N(Et)CH₂Ph-4-COOH | H |
| 699 | Et | N | C | NC₄H₈ | Et | CO | SB | N(Et)CH₂Ph-4-COOH | H |
| 700 | Et | N | C | NEt₂ | Et | CO | SB | N(Et)CH₂Ph-4-COOH | H |

TABLE 21

| No. | R¹ | A | Z | R² | R⁴ | R⁷ | R⁸ | R¹² | R¹³ |
|-----|----|----|----|------|----|----|----|------|-----|
| 701 | Et | N | C | OH | Et | CO | SB | N(Et)CH₂Ph-4-COOH | H |
| 702 | Et | N | C | N₂C₄H₉ | Et | CO | SB | N(nPr)CH₂Ph-4-COOH | H |
| 703 | Et | N | C | NC₄H₈ | Et | CO | SB | N(nPr)CH₂Ph-4-COOH | H |
| 704 | Et | N | C | NEt₂ | Et | CO | SB | N(nPr)CH₂Ph-4-COOH | H |
| 705 | Et | N | C | OH | Et | CO | SB | N(nPr)CH₂Ph-4-COOH | H |
| 706 | Et | N | C | N₂C₄H₉ | Et | CO | SB | N(nBu)CH₂Ph-4-COOH | H |
| 707 | Et | N | C | NC₄H₈ | Et | CO | SB | N(nBu)CH₂Ph-4-COOH | H |
| 708 | Et | N | C | NEt₂ | Et | CO | SB | N(nBu)CH₂Ph-4-COOH | H |
| 709 | Et | N | C | OH | Et | CO | SB | N(nBu)CH₂Ph-4-COOH | H |
| 710 | Et | N | C | N₂C₄H₉ | Et | CO | SB | N(nPen)CH₂Ph-4-COOH | H |
| 711 | Et | N | C | NC₄H₈ | Et | CO | SB | N(nPen)CH₂Ph-4-COOH | H |
| 712 | Et | N | C | NEt₂ | Et | CO | SB | N(nPen)CH₂Ph-4-COOH | H |
| 713 | Et | N | C | OH | Et | CO | SB | N(nPen)CH₂Ph-4-COOH | H |
| 714 | Et | N | C | N₂C₄H₉ | Et | CO | SB | N(nHex)CH₂Ph-4-COOH | H |
| 715 | Et | N | C | NC₄H₈ | Et | CO | SB | N(nHex)CH₂Ph-4-COOH | H |
| 716 | Et | N | C | NEt₂ | Et | CO | SB | N(nHex)CH₂Ph-4-COOH | H |
| 717 | Et | N | C | OH | Et | CO | SB | N(nHex)CH₂Ph-4-COOH | H |

The compounds of the present invention may be prepared by a process known per se. The typical schemes which may be used to prepare the compounds of the present invention will be illustrated hereinafter. In the following schemes, (H) means a hydrogen atom which may be optionally substituted for the illustrated group.

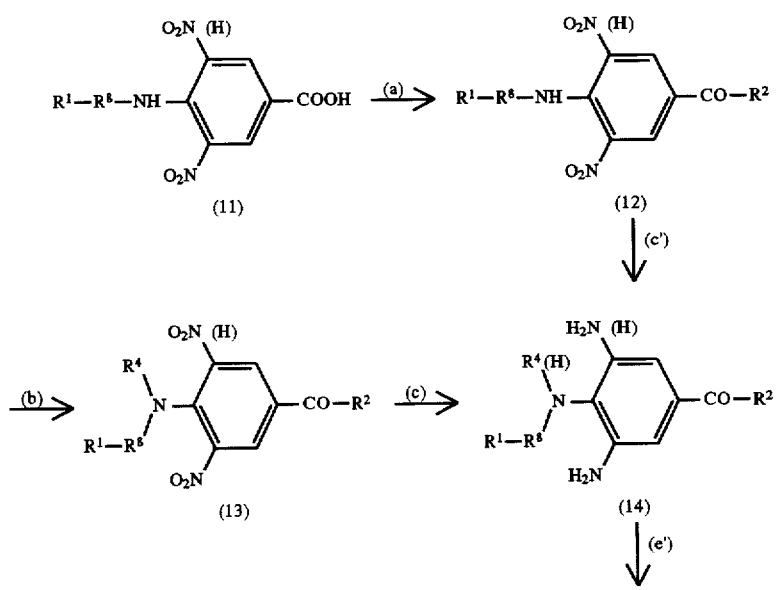

-continued
Scheme (1):

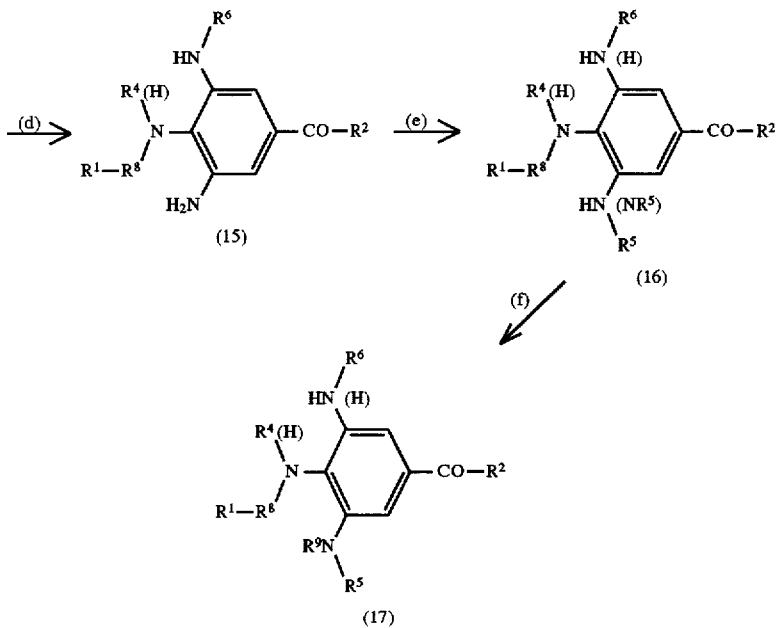

Step [1]-(a)

The compound of the formula (11) [wherein $R^1$ and $R^8$ have the same meanings as above] is dissolved in an organic solvent, such as tetrahydrofuran, acetone, dichloromethane, pyridine, triethylamine, or N,N-dimethylformamide. Further, the compound capable of converting the —COOH group to the —$COR^2$ group [wherein $R^2$ is three- to seven-membered saturated cycloaliphatic amino group which may be interrupted by one or more nitrogen, oxygen or sulfur atoms, —$NHR^{23}$, —$N(R^{24})_2$, or —$NH_2$ group] is also dissolved in an organic solvent, such as those mentioned above. Then, the latter solution is added to the former solution, and the reaction is performed in the presence of an appropriate condensation agent at 0° to 100° C. for 3 to 72 hours to obtain the compound of the formula (12) [wherein $R^1$, $R^2$ and $R^8$ have the same meanings as above]. The compound capable of converting the —COOH group to the —$COR^2$ group is, for example, morpholine when $R^2$ is morpholino group. When $R^2$ is the group other than morpholino group, such a compound can be appropriately selected in view of the desired $R^2$ group by those skilled in the art.

Step [1]-(b)

The compound of the formula (12) is dissolved in a solvent, such as acetone, dichloromethane, tetrahydrofuran, pyridine, alcohol, ethyl acetate, or N,N-dimethylformamide. Alkyl iodide having 1 to 6 carbon atoms and silver (I) oxide are added thereto. The reaction is performed with stirring for 3 to 72 hours to obtain the compound of the formula (13) [wherein $R^4$ is alkyl of 1 to 6 carbon atoms, and $R^1$, $R^2$ and $R^8$ have the same meanings as above].

Step [1]-(c), (c')

The compound of the formula (12) or (13) is dissolved in a solvent, such as alcohol or ethyl acetate. After an appropriate reducing agent, such as tin (II) chloride dihydrate, or 10% palladium/carbon and hydrazine monohydrate, is added, the reaction is performed at 20° to 100° C. to obtain the compound of the formula (14) [wherein $R^1$, $R^2$, $R^4$ and $R^8$ have the same meanings as above].

Step [1]-(d)

The compound of the formula (14) is dissolved in a solvent, such as toluene, acetonitrile, diisopropylethylamine, dichloromethane, ethyl acetate, alcohol, or benzene, and then reacted with the compound of the formula $R^6X$ wherein X is a halogen atom, —OH or —COOH; $R^6$ is —$C(=O)(CH_2)_aC_6H_5$, —$C(=O)R^{41}$, —$C(=O)CH(C_6H_5)_2$, or alkyl of 1 to 6 carbon atoms; a is 0 or an integer of 1 to 6; and $R^{41}$ is alkyl of 1 to 6 carbon atoms, to obtain the compound of the formula (15).

Step [1]-(e), (e')

The compound of the formula (14) or (15) is dissolved in a solvent, such as chloroform, benzene, or pyridine. After the compound of the formula $R^5Y$ wherein $R^5$ has the same meaning as above, and Y is a leaving group, such as a halogen atom, and diisopropylethylamine are added, the whole is heated under reflux for 1 hour to 5 days to obtain the compound of the formula (16). If necessary, one or more protective groups may be removed.

Step [1]-(f)

The compound of the formula (16) is dissolved in a solvent, such as N,N-dimethylformamide, tetrahydrofuran, chloroform, benzene, or pyridine. After alkyl halide of 1 to 6 carbon atoms, alkylcarbonyl halide having 1 to 6 carbon atoms in the alkyl moiety, alkylcarboxylic acid having 1 to 7 carbon atoms, or alkyl isocyanate of 1 to 7 carbon atoms is added, the reaction is performed to obtain the compound of the formula (17) [wherein $R^1$, $R^2$, $R^4$, $R^5$ and $R^6$ have the same meanings as above; $R^9$ is —$COR^{42}$, alkyl of 1 to 6 carbon atoms, —$C(=O)NH_2$, or —$C(=O)NHR^{43}$; $R^{42}$ is alkyl of 1 to 6 carbon atoms; and $R^{43}$ is alkyl of 1 to 6 carbon atoms]. If necessary, one or more protective groups may be removed.

Scheme (2):

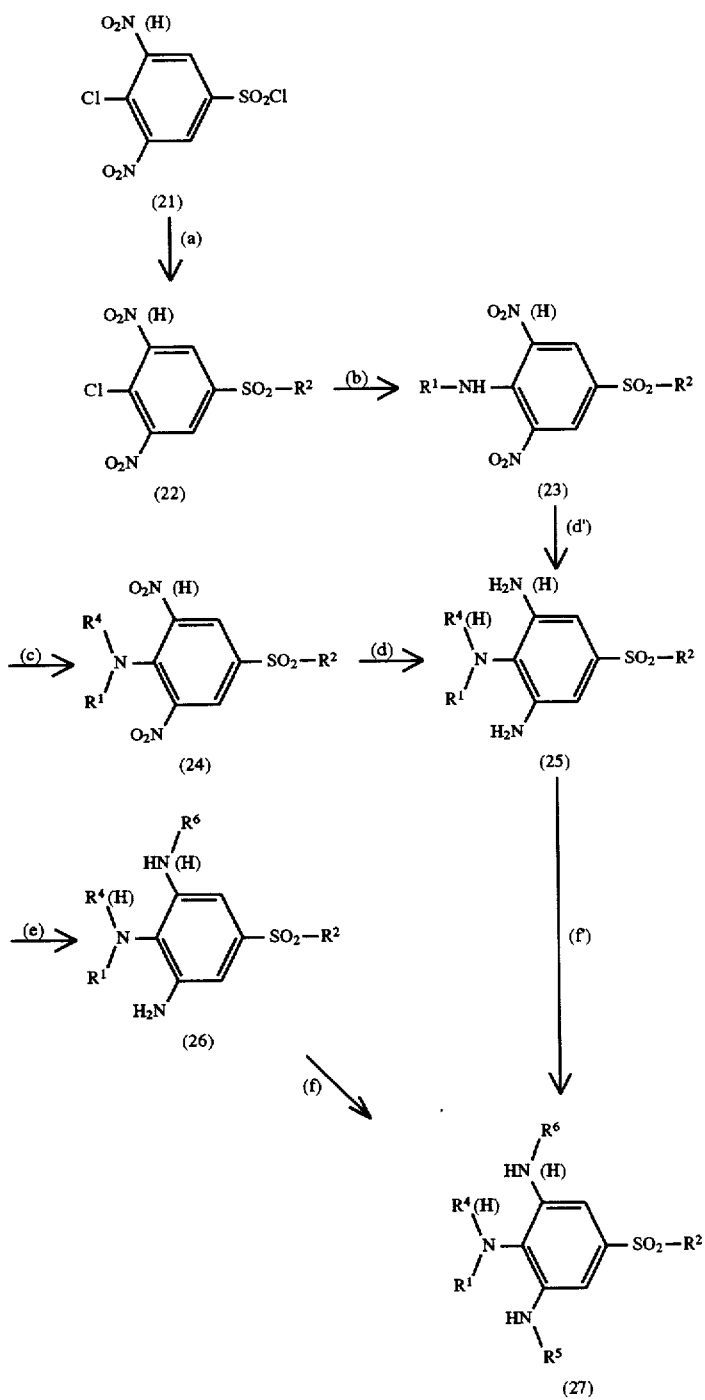

Step [2]-(a)

The sulfonyl chloride compound of the formula (21) is dissolved in an organic solvent, such as dichloromethane, pyridine, or triethylamine. Further, the compound capable of converting the —$SO_2Cl$ group to the —$SO_2R^2$ group [wherein $R^2$ is three- to seven-membered saturated cycloaliphatic amino group which may be interrupted by one or more nitrogen, oxygen or sulfur atoms, —$NHR^{23}$, —$N(R^{24})_2$, or —$NH_2$ group] is also dissolved in an organic solvent, such as those mentioned above. Then, the latter solution is added to the former solution, and the reaction is performed at −78° to 25° C. for 3 to 10 hours to obtain the compound of the formula (22) [wherein $R^2$ has the same meaning as above]. The compound capable of converting the —$SO_2Cl$ group to the —$SO_2R^2$ group is, for example, morpholine when $R^2$ is morpholino group. When $R^2$ is the group other than morpholino group, such a compound can be appropriately selected in view of the desired $R^2$ group by those skilled in the art.

Step [2]-(b)

The compound of the formula (22) is dissolved in a solvent, such as acetone, dichloromethane, tetrahydrofuran, pyridine, alcohol, or water. The compound of the formula $R^1NH_2$ [wherein $R^1$ has the same meaning as above] is added after dissolved in dichloromethane, tetrahydrofuran, pyridine, or alcohol if necessary, and the reaction is performed at $-78°$ to $100°$ C. to obtain the compound of the formula (23).

Step [2]-(c)

The compound of the formula (23) is dissolved in a solvent, such as N,N-dimethylformamide. Alkyl iodide having 1 to 6 carbon atoms and silver (I) oxide are added thereto. The reaction is performed for 3 to 72 hours to obtain the compound of the formula (24) [wherein $R^4$ is alkyl of 1 to 6 carbon atoms, and $R^1$ and $R^2$ have the same meanings as above].

Step [2]-(d), (d')

The compound of the formula (23) or (24) is dissolved in a solvent, such as ethyl acetate or alcohol. After an appropriate reducing agent, such as tin (II) chloride dihydrate, or 10% palladium/carbon and hydrazine monohydrate, is added, the reaction is performed at $20°$ to $100°$ C. to obtain the compound of the formula (25) [wherein $R^1$, $R^2$ and $R^4$ have the same meanings as above].

Step [2]-(e), (f), (f')

The compound of the formula (25) is dissolved in a solvent, such as toluene, dichloromethane, ethyl acetate, tetrahydrofuran, acetonitrile, alcohol, benzene, or N,N-dimethylformamide, and then reacted with the compound having a desired substituent, and if necessary, one or more protective groups are removed to obtain the compound of the formula (26) or (27) [wherein $R^1$, $R^2$, $R^4$, $R^5$ and $R^6$ have the same meanings as above].

Scheme (3):

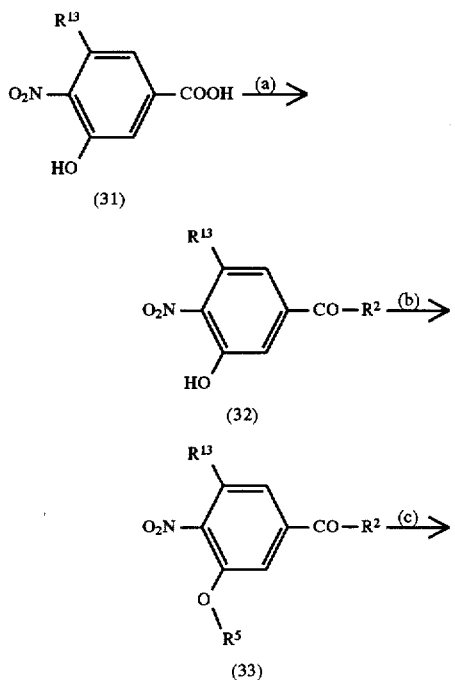

Scheme (3):

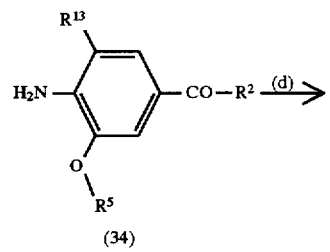

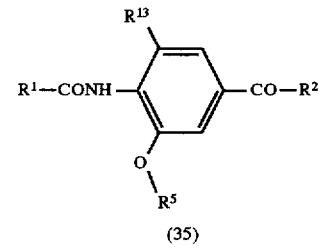

Step [3]-(a)

The compound of the formula (31) [wherein $R^{13}$ has the same meaning as above] is dissolved in a solvent, such as chloroform, tetrahydrofuran, acetone, pyridine, alcohol, or N,N-dimethylformamide, and reacted with the compound capable of converting the —COOH group to the —$COR^2$ group [wherein $R^2$ has the same meaning as above] and an appropriate condensation agent to obtain the compound of the formula (32). The compound capable of converting the —COOH group to the —$COR^2$ group is, for example, morpholine when $R^2$ is morpholino group. When $R^2$ is the group other than morpholino group, such a compound can be appropriately selected in view of the desired $R^2$ group by those skilled in the art.

Step [3]-(b)

The compound of the formula (32) is reacted with the compound of the formula $R^5Y$ [wherein $R^5$ and Y have the same meanings as above] in the presence of a base, such as sodium hydride in a solvent, such as chloroform, tetrahydrofuran, acetone, pyridine, or N,N-dimethylformamide to obtain the compound of the formula (33).

Step [3]-(c)

The compound of the formula (33) is dissolved in a solvent, such as alcohol or ethyl acetate, and treated with an appropriate reducing agent, such as hydrazine monohydrate and 10% palladium/carbon, or tin (II) chloride dihydrate, at $20°$ to $100°$ C. to obtain the compound of the formula (34).

Step [3]-(d)

The compound of the formula (34) is dissolved in a solvent, such as pyridine, and then reacted with the compound having a desired substituent at $-10°$ to $100°$ C. to obtain the compound of the formula (35). If the resulting compound has one or more protective groups, such groups may be removed, using an acid and/or base.

Scheme (4):

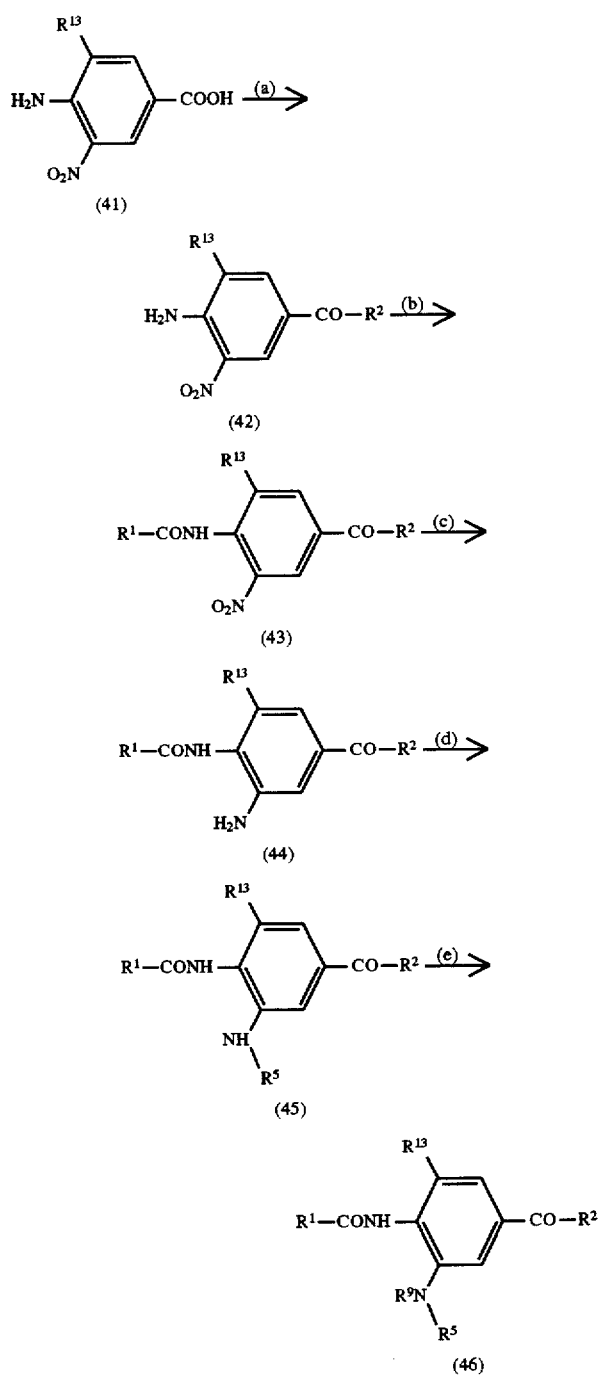

Step [4]-(a)

The compound of the formula (41) [wherein $R^{13}$ has the same meaning as above] is dissolved in a solvent, such as chloroform, tetrahydrofuran, benzene, pyridine, or N,N-dimethylformamide, and reacted with the compound capable of converting the —COOH group to the —$COR^2$ group [wherein $R^2$ has the same meaning as above] and an appropriate condensation agent to obtain the compound of the formula (42). The compound capable of converting the —COOH group to the —$COR^2$ group is, for example, diethylamine when $R^2$ is diethylamino group. When $R^2$ is the group other than morpholino group, such a compound can be appropriately selected in view of the desired $R^2$ group by those skilled in the art.

Step [4]-(b)

The compound of the formula (42) is dissolved in a solvent, such as pyridine, and then reacted with the compound having a desired substituent at −10° to 100° C. to obtain the compound of the formula (43).

Step [4]-(c)

The compound of the formula (43) is dissolved in a solvent, such as alcohol or ethyl acetate, and treated with an appropriate reducing agent, such as hydrazine monohydrate and 10% palladium/carbon, or tin (II) chloride dihydrate, at 20° to 100° C. to obtain the compound of the formula (44).

Step [4]-(d)

The compound of the formula (44) is dissolved in a solvent, such as diisopropylethylamine, pyridine, or chloroform, and reacted with the compound of the formula $R^5Y$ [wherein $R^5$ and Y have the same meanings as above] at 20° to 100° C. to obtain the compound of the formula (45).

Step [4]-(e)

The compound of the formula (45) is dissolved in a solvent, such as diisopropylethylamine or pyridine, and then reacted with the compound having a desired substituent at −10° to 100° C. to obtain the compound of the formula (46). If necessary, one or more protective groups may be removed by treating with an acid and/or base.

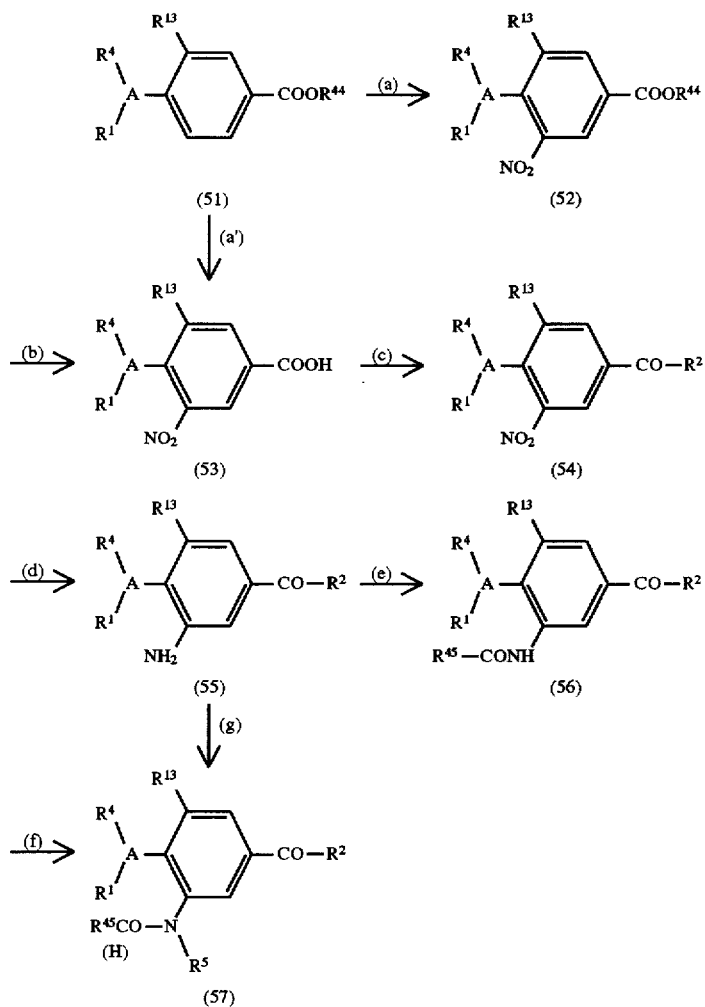

Scheme (5):

Step [5]-(a),(a')

The compound of the formula (51) [wherein $R^1$, $R^4$, $R^{13}$, and A have the same meanings as above, and $R^{44}$ is a hydrogen atom or alkyl of 1 to 6 carbon atoms] is dissolved in a solvent, such as acetic anhydride, fuming nitric acid is added and then the reaction is performed at −10° to 30° C. for 1 to 10 hours, or mixed acid of sulfuric and nitric acids is added to the compound of the formula (51) and the reaction is performed in the absence of a solvent at −10° to 30° C. for 1 to 10 hours, to obtain the compound of the formula (52) [wherein $R^1$, $R^4$, $R^{13}$, $R^{44}$, and A have the same meanings as above].

Step [5]-(b)

The compound of the formula (52) is dissolved in a solvent, such as methanol, ethanol, tetrahydrofuran or dioxane. The solution is treated with an alkaline aqueous solution at 10° C. to temperature below the boiling point of the solvent, cooled, and then, deposited with acid to obtain the compound of the formula (53) [wherein $R^1$, $R^4$, $R^{13}$, and A have the same meanings as above].

Step [5]-(c)

The compound of the formula (53) is dissolved in a solvent, such as chloroform, tetrahydrofuran, benzene, pyridine, or N,N-dimethylformamide, and reacted with the compound capable of converting the —COOH group to the —COR$^2$ group [wherein $R^2$ has the same meaning as above] and an appropriate condensation agent to obtain the compound of the formula (54) [wherein $R^1$, $R^2$, $R^4$, $R^{13}$, and A have the same meanings as above]. The compound capable of converting the —COOH group to the —COR$^2$ group is, for example, morpholine when $R^2$ is morpholino group. When $R^2$ is the group other than morpholino group, such a compound can be appropriately selected in view of the desired $R^2$ group by those skilled in the art.

Step [5]-(d)

The compound of the formula (54) is dissolved in a solvent, such as alcohol or ethyl acetate, and treated with an appropriate reducing agent, such as hydrazine monohydrate and 10% palladium/carbon, tin (II) chloride dihydrate, or sodium hydrosulfite, at 20° to 100° C. to obtain the compound of the formula (55).

Step [5]-(e)

The compound of the formula (55) is dissolved in a solvent, such as pyridine or N,N-dimethylformamide, and then reacted with the compound having a desired substituent at −10° to 100° C. to obtain the compound of the formula (56) [wherein $R^1$, $R^2$, $R^4$, $R^{13}$, and A have the same meanings as above, $R^{45}$ is a hydrogen atom, alkyl of 1 to 6 carbon atoms, haloalkyl of 1 to 6 carbon atoms, or $NHR^{21}$, and $R^{21}$ has the same meaning as above].

Step [5]-(f)

The compound of the formula (56) is dissolved in a solvent, such as dimethylsulfoxide or N,N-dimethylformamide, and reacted with the compound of the formula $R^5Y$ [wherein $R^5$ and Y have the same meanings as above] in the presence of a base, such as sodium hydride or potassium hydroxide at -20° to 100° C. to obtain the compound of the formula (57) [wherein $R^1$, $R^2$, $R^4$, $R^5$, $R^{13}$, $R^{45}$, and A have the same meanings as above]. If necessary, one or more protective groups may be removed by treating with an acid and/or base.

Step [5]-(g)

The compound of the formula (55) is dissolved in a solvent, such as acetic acid, and then reacted with the compound having a desired substituent at 0° to 100° C. The resulting compound is reacted with an appropriate reducing agent, such as borane-diethylamine complex, at 0° to 100° C. to obtain the compound of the formula (57) [wherein $R^1$, $R^2$, $R^4$, $R^5$, $R^{13}$, $R^{45}$, and A have the same meanings as above]. If necessary, one or more protective groups may be removed by treating with an acid and/or base.

Scheme (6):

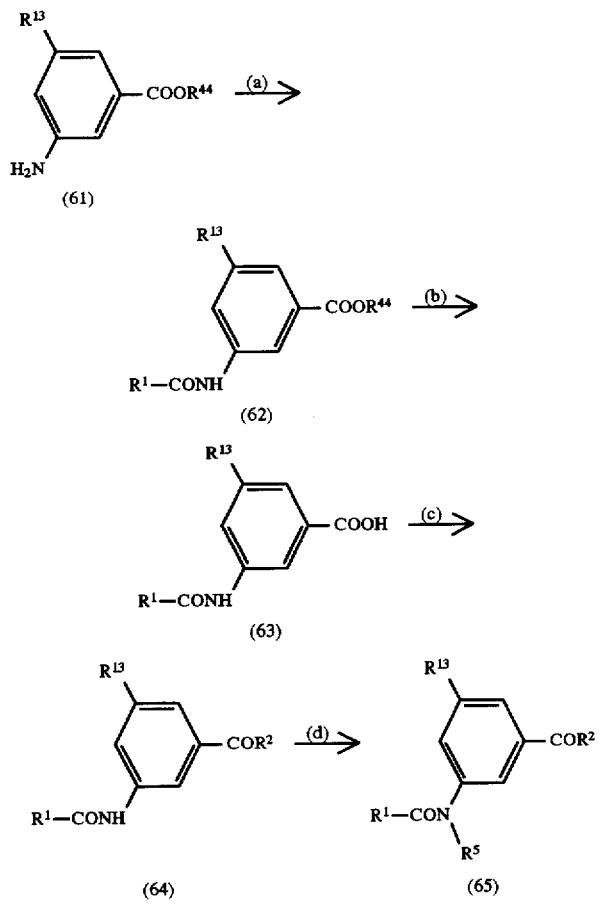

Step [6]-(a)

The compound of the formula (61) [wherein $R^{13}$ and $R^{44}$ have the same meanings as above] is dissolved in a solvent, such as pyridine or N,N-dimethylformamide, and then reacted with the compound having a desired substituent at -10° to 100° C. to obtain the compound of the formula (62) [wherein $R^1$, $R^{13}$, and $R^{44}$ have the same meanings as above].

Step [6]-(b)

The compound of the formula (62) is dissolved in a solvent, such as methanol, ethanol, tetrahydrofuran or dioxane. The solution is treated with an alkaline aqueous solution at 10° C. to temperature below the boiling point of the solvent, cooled, and then, deposited with acid to obtain the compound of the formula (63) [wherein $R^1$ and $R^{13}$ have the same meanings as above].

Step [6]-(c)

The compound of the formula (63) is dissolved in a solvent, such as chloroform, tetrahydrofuran, benzene, pyridine, or N,N-dimethylformamide, and reacted with the compound capable of converting the —COOH group to the —$COR^2$ group [wherein $R^2$ has the same meaning as above] and an appropriate condensation agent to obtain the compound of the formula (64) [wherein $R^1$, $R^2$, and $R^{13}$ have the same meanings as above]. The compound capable of converting the —COOH group to the —$COR^2$ group is, for example, morpholine when $R^2$ is morpholino group. When $R^2$ is the group other than morpholino group, such a compound can be appropriately selected in view of the desired $R^2$ group by those skilled in the art.

Step [6]-(d)

The compound of the formula (64) is dissolved in a solvent, such as dimethylsulfoxide or N,N-dimethylformamide, and is reacted with the compound of the formula $R^5Y$ [wherein $R^5$ and Y have the same meanings as above] in the presence of a base, such as sodium hydride or potassium hydroxide at -20° to 100° C. to obtain the compound of the formula (65) [wherein $R^1$, $R^2$, $R^5$, and $R^{13}$ have the same meanings as above]. If necessary, one or more protective groups may be removed by treating with an acid and/or base.

Scheme (7):

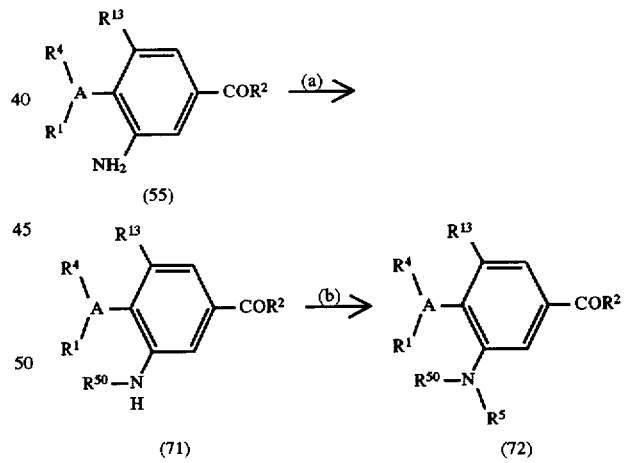

Step [7]-(a)

The compound of the formula (55) [wherein $R^1$, $R^2$, $R^{13}$, and A have the same meanings as above] obtained in the above step [5]-(d), and if necessary an acid catalyst, such as tosyl anhydrous p-toluenesulfonic acid, are dissolved in a solvent, such as ethanol or benzene. After 5 to 10% palladium/carbon is suspended, the compound of the formula $R^{51}CHO$ [wherein $R^{51}$ is alkyl of 1 to 5 carbon atoms] is reacted therewith under hydrogen gas atmosphere at -20° to 100° C. to obtain the compound of the formula (71) [wherein $R^1$, $R^2$, $R^4$, $R^{13}$, and A have the same meanings as above, and $R^{50}$ is alkyl of 1 to 6 carbon atoms].

Step [7]-(b)

The compound of the formula (71) [wherein $R^1$, $R^2$, $R^4$, $R^{13}$, $R^{50}$, and A have the same meanings as above] is dissolved in a solvent, such as benzene, toluene or chloroform. After the compound of the formula $R^5Y$ [wherein $R^5$ and Y have the same meanings as above] and a base, such as diisopropylethylamine, are added, the whole is heated under reflux for 1 hour to 7 days to obtain the compound of the formula (72) [wherein $R^1$, $R^2$, $R^4$, $R^{13}$, $R^{50}$, and A have the same meanings as above]. If necessary, one or more protective groups may be removed by treating with an acid and/or base.

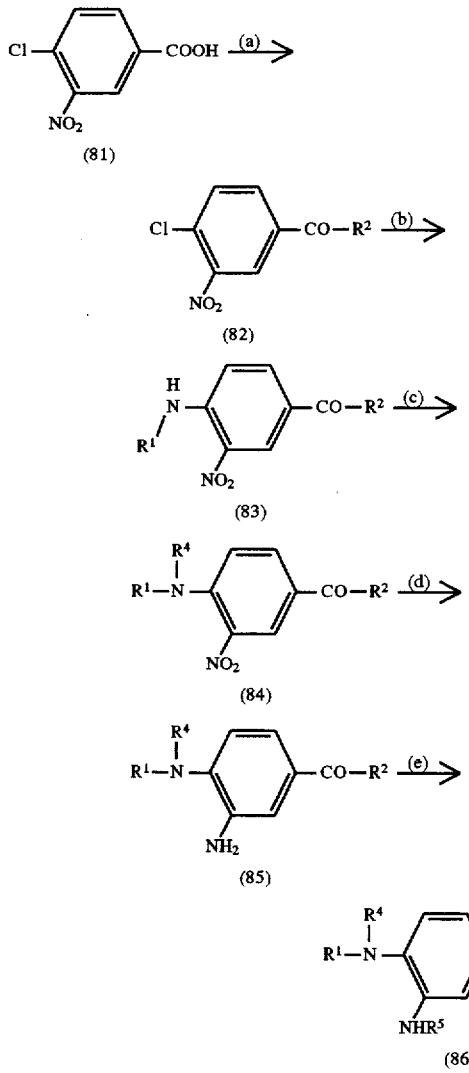

Scheme (8):

Step [8]-(a)

As in the above step [1]-(a), the compound of the formula (81) is reacted with the compound capable of converting the —COOH group to the —$COR^2$ group [wherein $R^2$ has the same meaning as above] and an appropriate condensation agent to obtain the compound of the formula (82) [wherein $R^2$ has the same meaning as above]. The compound capable of converting the —COOH group to the —$COR^2$ group is, for example, morpholine, when $R^2$ is morpholino group. When $R^2$ is the group other than morpholino group, such a compound can be appropriately selected in view of the desired $R^2$ group by those skilled in the art.

Step [8]-(b)

As in the above step [2]-(b), the compound of the formula (82) [wherein $R^2$ has the same meaning as above] is reacted with the compound of the formula $R^1NH_2$ [wherein $R^1$ has the same meaning as above] to obtain the compound of the formula (83) [wherein $R^1$ and $R^2$ have the same meanings as above].

Step [8]-(c)

As in the above step [2]-(c), the compound of the formula (83) [wherein $R^1$ and $R^2$ have the same meanings as above] is reacted with alkyl iodide of 1 to 6 carbon atoms or the like and silver (I) oxide to obtain the compound of the formula (84) [wherein $R^4$ is alkyl of 1 to 6 carbon atoms, and $R^1$ and $R^2$ have the same meanings as above].

Step [8]-(d)

As in the above step [2]-(d), the compound of the formula (84) [wherein $R^1$, $R^2$ and $R^4$ have the same meanings as above] is treated with an appropriate reducing agent to obtain the compound of the formula (85) [wherein $R^1$, $R^2$ and $R^4$ have the same meanings as above].

Step [8]-(e)

The compound of the formula (85) [wherein $R^1$, $R^2$ and $R^4$ have the same meanings as above] is dissolved in a non-polar solvent, such as benzene, or toluene. After a base, such as diisopropylethylamine, is added, the compound of the formula $R^5Y$ [wherein $R^5$ and Y have the same meanings as above] is reacted at 20° to 100° C. to obtain the compound of the formula (86) [wherein $R^1$, $R^2$, $R^4$, and $R^5$ have the same meanings as above]. If necessary, one or more protective groups may be removed by treating with an acid and/or base.

Scheme (9):

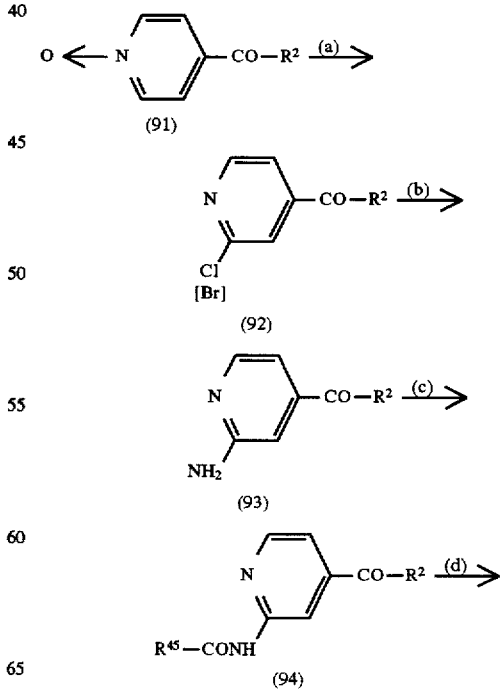

-continued
Scheme (9):

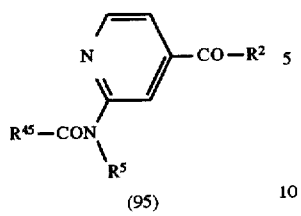

(95)

Step [9]-(a)

Phosphorus oxychloride or phosphorus oxybromide is added to the compound of the formula (91) [wherein $R^2$ has the same meaning as above], and the reaction is performed 0° to 150° C. for 1 to 24 hours to obtain the compound of the formula (92) [wherein $R^2$ has the same meaning as above].

Step [9]-(b)

Ammonia water is added to the compound of the formula (92) [wherein $R^2$ has the same meaning as above], and the reaction is performed 20° to 200° C. for 3 to 72 hours to obtain the compound of the formula (93) [wherein $R^2$ has the same meaning as above].

Step [9]-(c)

The compound of the formula (93) [wherein $R^2$ has the same meaning as above] is dissolved in a solvent, such as pyridine or N,N-dimethylformamide, after protected if necessary, and reacted with the compound having a desired substituent at $-10°$ to 100° C. to obtain the compound of the formula (94) [wherein $R^2$ and $R^{45}$ have the same meanings as above].

Step [9]-(d)

After one or more protect groups are removed by alkaline treatment if necessary, and reaction with the compound having a desired substituent and an appropriate condensation agent is performed if necessary, the compound of the formula (94) [wherein $R^2$ and $R^{45}$ have the same meanings as above] is dissolved in a solvent, such as dimethylsulfoxide or N,N-dimethylformamide, and reacted with the compound of the formula $R^5Y$ [wherein $R^5$ and Y have the same meanings as above] in the presence of a base, such as sodium hydride or potassium hydroxide, at $-20°$ to 100° C. to obtain the compound of the formula (95) [wherein $R^2$, $R^5$, and $R^{45}$ have the same meanings as above]. If necessary, one or more protective groups may be removed by treating with an acid and/or base.

Scheme (10):

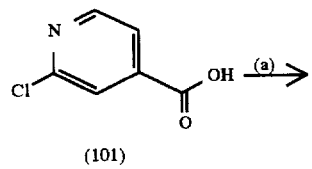

(101)

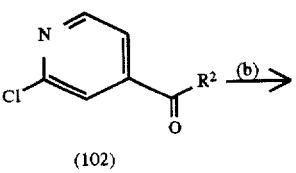

(102)

-continued
Scheme (10):

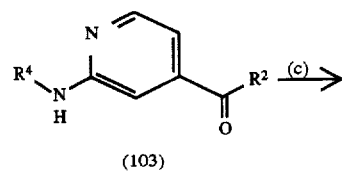

(103)

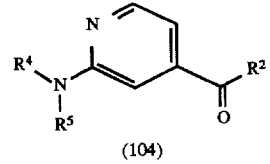

(104)

Step[10]-(a)

The compound of the formula (102) [wherein $R^2$ has the same meaning as above] is obtained from the starting compound of the formula (101) as in the above step [1]-(a).

Step [10]-(b)

The compound of the formula (102) [wherein $R^2$ has the same meaning as above] is dissolved in the compound of the formula $R^4NH_2$ [wherein $R^4$ is alkyl of 1 to 6 carbon atoms], and the solution is heated at 50° to 150° C. to obtain the compound of the formula (103) [wherein $R^2$ and $R^4$ have the same meanings as above].

Step [10]-(c)

The compound of the formula (103) [wherein $R^2$ and $R^4$ have the same meanings as above] is dissolved in a nonpolar solvent, such as benzene or toluene. After a base, such as diisopropylethylamine, is added, the compound of the formula $R^5Y$ [wherein $R^5$ and Y have the same meanings as above] is reacted at 20° to 150° C. to obtain the compound of the formula (104) [wherein $R^2$, $R^4$ and $R^5$ have the same meanings as above]. If necessary, one or more protective groups may be removed by treating with an acid and/or base.

Scheme (11):

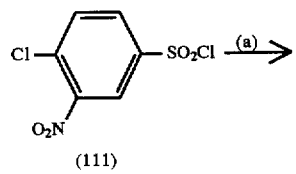

(111)

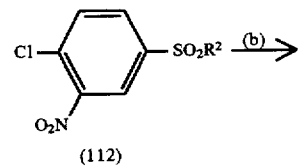

(112)

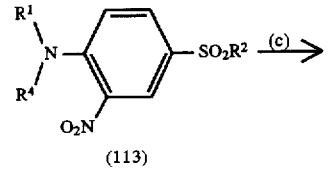

(113)

Scheme (11):

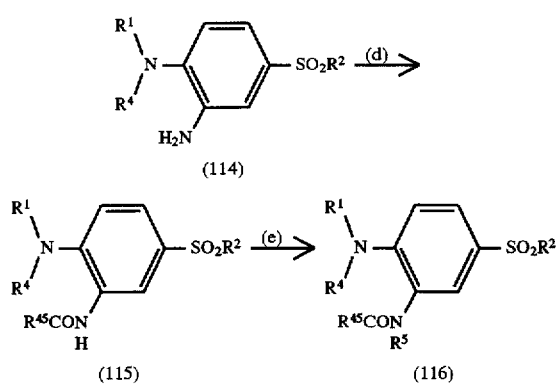

Step [11]-(a)

The compound of the formula (112) [wherein $R^2$ has the same meaning as above] is obtained from the starting compound, sulfonylchloride of the formula (111) as in the above step [2]-(a).

Step [11]-(b)

The compound of the formula (112) [wherein $R^2$ has the same meaning as above] is dissolved in a solvent, such as cyclic ether (such as tetrahydrofuran or dioxane) or water. After a secondary amine of the formula. $NHR^1R^4$ [wherein $R^1$ and $R^4$ have the same meanings as above] is added, the reaction is performed at 0° to 120° C. to obtain the compound of the formula (113) [wherein $R^1$, $R^2$ and $R^4$ have the same meanings as above].

Step [11]-(c)

The compound of the formula (113) [wherein $R^1$, $R^2$ and $R^4$ have the same meanings as above] is dissolved in lower alcohol. After an appropriate reducing agent, such as sodium hydrosulfite, or 10% palladium/carbon and hydrazine monohydrate, is added, the reaction is performed at −10° to 100° C. to obtain the compound of the formula (114) [wherein $R^1$, $R^2$ and $R^4$ have the same meanings as above].

Step [11]-(d)

As in the above step [5]-(e), the compound of the formula (114) [wherein $R^1$, $R^2$ and $R^4$ have the same meanings as above] is reacted with the compound having a desired substituent to obtain the compound of the formula (115) [wherein $R^1$, $R^2$, $R^4$ and $R^{45}$ have the same meanings as above].

Step [11]-(e)

As in the above step [5]-(f), the compound of the formula (115) [wherein $R^1$, $R^2$, $R^4$ and $R^{45}$ have the same meanings as above] is reacted with the compound of the formula $R^5Y$ [wherein $R^5$ and Y have the same meanings as above] in the presence of a base, such as sodium hydride or potassium hydroxide, to obtain the compound of the formula (116) [wherein $R^1$, $R^2$, $R^4$, $R^5$ and $R^{45}$ have the same meanings as above]. If necessary, one or more protective groups may be removed by treating with an acid and/or base.

Scheme (12):

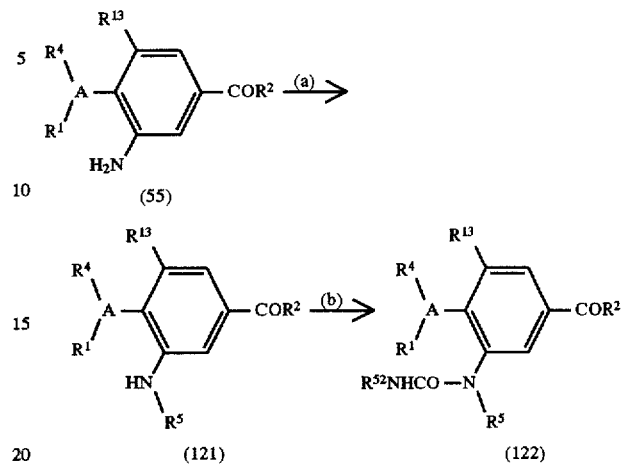

Step [12]-(a)

The compound of the formula (55) [wherein $R^1$, $R^2$, $R^4$, $R^{13}$, and A have the same meanings as above] obtained in the above step [5]-(d) is dissolved in a solvent, such as glacial acetic acid or benzene, and reacted with the compound of the formula $R^{53}CHO$ [wherein $R^{53}$ is —$C_6H_4COOR^{54}$, —$C_6H_4OR^{54}$, —$C_6H_4N(R^{54})_2$, or —$C_6H_4$-azole, and $R^{54}$ is hydrogen atom or alkyl of 1 to 6 carbon atoms] and if necessary an acid catalyst, such as anhydrous p-toluenesulfonic acid, at −20° to 100° C. After adding a reducing agent, such as borane-diethylamine complex, the reaction is further performed at −20° to 100° C. to obtain the compound of the formula (121) [wherein $R^1$, $R^2$, $R^4$, $R^5$, $R^{13}$, and A have the same meanings as above].

Step [12]-(b)

The compound of the formula (121) [wherein $R^1$, $R^2$, $R^4$, $R^5$, $R^{13}$, and A have the same meanings as above] is dissolved in a solvent, such as benzene, toluene, chloroform or pyridine, and reacted with the isocyanate compound of the formula $R^{52}N=C=O$ [wherein $R^{52}$ is alkyl of 1 to 5 carbon atoms] at −20° to 150° C. to obtain the compound of the formula (122) [wherein $R^1$, $R^2$, $R^4$, $R^5$, $R^{13}$, $R^{52}$, and A have the same meanings as above]. If necessary, one or more protective groups may be removed by treating with an acid and/or base.

Scheme (13):

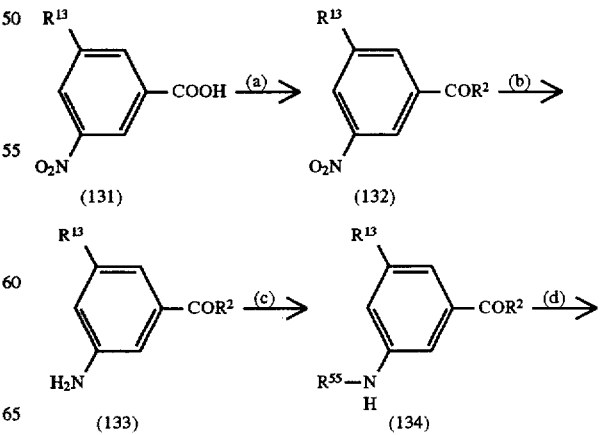

-continued

Scheme (13):

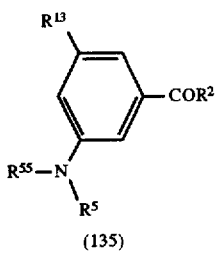

(135)

Step [13]-(a)

The compound of the formula (131) [wherein $R^{13}$ has the same meaning as above] is dissolved in a solvent, such as tetrahydrofuran or N,N-dimethylformamide, and reacted with the compound capable of converting the —COOH group to the —COR$^2$ group [wherein $R^2$ has the same meaning as above] and an appropriate condensation agent to obtain the compound of the formula (132) [wherein $R^2$ and $R^{13}$ have the same meanings as above]. The compound capable of converting the —COOH group to the —COR$^2$ group is, for example, morpholine, when $R^2$ is morpholino group. When $R^2$ is the group other than morpholino group, such a compound can be appropriately selected in view of the desired $R^2$ group by those skilled in the art.

Step [13]-(b)

The compound of the formula (132) [wherein $R^2$ and $R^{13}$ have the same meanings as above] is dissolved in a solvent, such as alcohol or ethyl acetate. After an appropriate reducing agent, such as hydrazine monohydrate and 10% palladium/carbon, tin (II) chloride dihydrate, or sodium hydrosulfite, the reaction is performed at 20° to 100° C. to obtain the compound of the formula (133) [wherein $R^2$ and $R^{13}$ have the same meanings as above].

Step [13]-(c)

The compound of the formula (133) [wherein $R^2$ and $R^{13}$ have the same meanings as above], and if necessary an acid catalyst, such as anhydrous p-toluenesulfonic acid, are dissolved in a solvent, such as ethanol or benzene. After 5 to 10% palladium/carbon is suspended, the compound of the formula $R^{56}$CHO [wherein $R^{56}$ is alkyl of 1 to 5 carbon atoms] is reacted therewith under hydrogen gas atmosphere at −20° to 100° C. to obtain the compound of the formula (134) [wherein $R^2$ and $R^{13}$ have the same meanings as above, and $R^{55}$ is alkyl of 1 to 6 carbon atoms].

Step [13]-(d)

The compound of the formula (134) [wherein $R^2$, $R^{13}$ and $R^{55}$ have the same meanings as above] is dissolved in a solvent, such as benzene, toluene or chloroform. After the compound of the formula $R^5$Y [wherein $R^5$ and Y have the same meanings as above] and a base, such as diisopropylethylamine, are added, the whole is heated under reflux for 1 hour to 7 days to obtain the compound of the formula (135) [wherein $R^2$, $R^5$, $R^{13}$ and $R^{55}$ have the same meanings as above]. If necessary, one or more protective groups may be removed by treating with an acid and/or base.

The ester compound of the formula (I) can be hydrolyzed in an organic solvent, such as methanol, ethanol, butanol or tetrahydrofuran in the presence of alkaline aqueous solution at 0° to 100° C. for 1 to 72 hours and deposited with acid, and then converted to the free compound of the formula (I).

Further, the salt, particularly the pharmaceutically acceptable salt, of the compound of the formula (I) can be prepared by utilizing the compound of the formula (I) and an equivalent amount of an alkali or an acid, evaporating the solvent or concentrating the solution, and drying and purifying the residue.

The benzene derivative of the formula (I) according to the present invention or the pharmaceutically acceptable salt thereof is sufficiently effective in improvement of the renal dysfunction without any function to blood pressure. Therefore, the present invention relates to a pharmaceutical composition, particularly an anti-kidney disease agent, containing the benzene derivative of the formula (I) or the pharmaceutically acceptable salt thereof as an active ingredient.

The compound of the formula (I) is effective as an agent for treating a kidney disease, such as nephritis, nephropathy, renal failure, nephrotic syndrome, asymptomatic proteinuria, hematuria, diabetic nephropathy, kidney disease induced by medicine, urinary tract infectious disease, or prostatitis. The compound of the formula (I) according to the present invention may be administered orally or parenterally (such as percutaneously, intravenously or intraperitoneally).

The compound of the formula (I) according to the present invention was orally administered to mice at the dose of 500 mg/kg, but no death was observed during one week.

The compound of the formula (I) may be formulated by adding one or more pharmaceutically acceptable additives, to powder, tablet, granule, capsule, suppository, injection, or oral solution. As the additives, there may be mentioned, for example, magnesium stearate, talc, lactose, dextrin, starches, methylcellulose, fatty acid glycerides, water, propyleneglycol, macrogols, alcohols, crystalline celluloses, hydroxypropylcellulose, low substituted hydroxypropylcellulose, carmelloses, povidone, polyvinylalcohol, or calcium stearate. Further, coloring agent, stabilizer, antioxidant, preservative, pH adjusting agent, isotonicity, solubilizing agent and/or soothing agent may be contained, if necessary. The granule, tablet, or capsule may be coated with a coating base, such as hydroxypropylmethyl cellulose or hydroxypropylmethyl cellulose phthalate.

The compound of the formula (I) may be contained at an amount of 0.1 to 500 mg, preferably 1 to 100 mg in a dose unit. The dose of the compound of the formula (I) is 0.1 to 150 mg/kg body weight, preferably 1 to 100 mg/kg body weight. The dose may be administered once a day, or divided twice or 3 times a day. The dose may be appropriately selected with respect to symptom of the patient.

The inventors of the present invention analyzed the three-dimensional structure of angiotensin II in solution by means of a method as originally developed, and studied the properties of various compounds, taking into account the affinities to angiotensin II in solution. More particularly, antagonism to angiotensin II receptor subtype 1 which is known to participates in antihypertensive function, a function to improve renal dysfunction in a renal dysfunction model animal, a function against blood pressure or the like were investigated in detail. As a result, the inventors found the compound of the formula (I) or a salt thereof has desired properties which are completely different from those of conventionally known antihypertensive compounds.

As mentioned above, the compound of the formula (I) or a salt thereof exhibits antagonism to the angiotensin II receptor subtype 1 which is one-hundredth (1/100) to one-thousandth (1/1000) or less as large as that of the conventionally known antagonist having a standard activity as an antihypertensive agent. The compound of the formula (I) or a salt thereof exhibits a function to improve renal dysfunction without substantial antagonism. In view of the conventional knowledge, it is greatly surprising that there exist compounds having such properties. It is still unclear how the compound of the formula (I) exhibits such properties. It is assumed that the properties are brought about from, for example, the specific antagonism to a angiotensin II receptor (i.e., a new receptor other than the known subtypes 1 and 2) which participates in renal interstitial cell growth causing exacerbation of renal failure, or accumulation of the compound to kidney, although the present invention is not limited to said assumption. Further, there is a possibility of a mechanism completely different from that of antagonism to angiotensin II receptor.

Even if the compound of the formula (I) according to the present invention or a salt thereof is classified in an angiotensin II receptor antagonist, it has the properties essentially different from those of the known angiotensin II receptor antagonists which have been developed as an antihypertensive agent, i.e., the antagonists having a strong antagonism to the receptor and a function to lower blood pressure. If the compound of the formula (I) or a salt thereof is not classified in an angiotensin II receptor antagonist, it is apparently different therefrom. Accordingly, the compound of the formula (I) according to the present invention or a salt thereof is novel with respect to the chemical structure, functional effects, and medical utility.

As above, the compound of the formula (I) according to the present invention or a salt thereof is sufficiently effective to renal dysfunction without affecting blood pressure. Therefore, it is possible to appropriately treat kidney diseases without any such problem as acute renal failure with the drugs having such properties while controlling blood pressure at a desired level by means of a suitable antihypertensive drug if necessary.

EXAMPLES

The present invention now will be further illustrated by, but is by no means limited to, the following Examples.

Example 1

Preparation of 3-nitro-4-valeramidobenzoic acid morpholide ([1]-(12)-1)

In tetrahydrofuran (800 ml), 3-nitro-4-valeramidobenzoic acid ([1]-(11)-1) (20.0 g) was dissolved. Dicyclohexylcarbodiimide (17.1 g) and 1-hydroxybenzotriazole (11.2 g) were added to the solution, and the mixture was stirred at room temperature for 15 minutes. Morpholine (7.27 g) was further added to the solution. The mixture was stirred for 16 hours. After the insolubles were removed from the reaction solution, the solution was concentrated and dried. The crude product was dissolved in chloroform, and the insolubles were removed, and the solution was purified by silica gel column chromatography (Kieselgel 60=400 g, chloroform/methanol=30/1) to obtain the compound ([1]-(12)-1) (22.95 g) as yellow needle crystals.

Melting point: 126.0°–126.5° C.

$^1$H-NMR (500 MHz, CDCl$_3$) δ: 0.97 (t, 3H), 1.44 (sext, 2H), 1.75 (quint, 2H), 2.52 (t, 2H), 3.4–3.9 (br, 8H), 7.69 (d, 1H), 8.34 (s, 1H), 8.95 (d, 1H), 10.42 (s, 1H)

Example 2

Preparation of 3-amino-4-valeramidobenzoic acid morpholide ([1]-(14)-1)

The compound ([1]-(12)-1) (8.00 g) prepared in Example 1 was dissolved in ethanol (800 ml) and heated to 50° C. Hydrazine monohydrate (8.0 ml) and 10% Pd/C (0.8 g) were added to the reaction solution, and the whole was stirred for 10 minutes. After the reaction solution was filtered through celite, the filtrate was concentrated and recrystallized from chloroform/hexane to obtain the compound ([1]-(14)-1) (6.97 g) as colorless needle crystals.

Melting point: 203.0°–205.0° C.

$^1$H-NMR (500 MHz, CDCl$_3$) δ: 0.97 (t, 3H), 1.43 (sext, 2H), 1.73 (quint, 2H) 2.43 (t, 2H), 3.4–3.9 (br, 8H), 3.88 (s, 2H), 6.65 (d, 1H), 6.71 (s, 1H), 7.06 (d, 1H), 7.92 (s, 1H)

Example 3

Preparation of 3-[(4-methoxycarbonylphenyl)methylamino]-4-valeramidobenzoic acid morpholide ([1]-(16)-1')

The compound ([1]-(14)-1) (6.10 g) prepared in Example 2 was suspended in benzene (600 ml), and methyl 4-bromomethylbenzoate (4.81 g) and diisopropylethylamine (25.8 g) were added to the suspension. Then, the reaction mixture was refluxed for 2 days. The reaction mixture was concentrated and the solvent was evaporated. The residue was purified by silica gel column chromatography (Kieselgel 60=260 g, ethyl acetate/hexane=5/1) to obtain the compound ([1]-(16)-1') (7.71 g) as white foam.

$^1$H-NMR (500 MHz, CDCl$_3$) δ: 0.94 (t, 3H), 1.39 (sext, 2H), 1.71 (quint, 2H), 2.44 (t, 2H), 3.0–3.9 (br, 8H), 3.91 (s, 3H), 4.37 (s, 2H), 4.76 (s, 1H), 6.45 (s, 1H), 6.62 (d, 1H), 7.01 (d, 1H), 7.41 (d, 2H), 7.95 (s, 1H), 7.99 (d, 1H)

Example 4

Preparation of 3-[[2'-(1-triphenylmethyltetrazol-5-yl)biphenyl-4-yl]methylamino-4-valeramidobenzoic acid morpholide ([1]-(16)-585') and 3-[di-[[2'-(1-triphenylmethyltetrazol-5-yl]biphenyl-4-yl]methylamino-4-valeramidobenzoic acid morpholide ([1]-(16)-594')

The compound ([1]-(14)-1) (13.0 g) prepared in Example 2 was dissolved in chloroform (1000 ml), and N-(triphenylmethyl)-5-[4'-(bromomethyl)biphenyl-2-yl] tetrazole (26.1 g) and diisopropylethylamine (55.0 g) were added. Then, the reaction mixture was refluxed for 4 days. The reaction mixture was concentrated. The residue was purified by silica gel column chromatography (Kieselgel 60=150 g, ethyl acetate/hexane=3/1) to obtain the compound ([1]-(16)-585') (19.6 g) and the compound ([1]-(16)-594') (10.4 g) as white foam, respectively. Compound ([1]-(16)-585')

$^1$H-NMR (500 MHz, CDCl$_3$) δ: 0.90 t, 3H), 1.38 (sext, 2H), 1.69 (quint, 2H), 2.33 (t, 2H), 3.2–3.9 (br, 8H), 4.20 (s, 2H), 4.35 (s, 1H) 6.69 (s, 1H), 6.73 (d, 1H), 6.94 (d, 6H), 7.1–7.2 (m, 4H), 7.2–7.6 (m, 13H), 7.90 (d, 1H) Compound ([1]-(16)-594')

$^1$H-NMR (500 MHz, CDCl$_3$) δ: 0.88 (t, 3H), 1.34 (sext, 2H), 1.61 (quint, 2H), 2.23 (t, 2H), 3.3–3.9 (br, 8H), 3.92 (s, 4H), 6.88 (d, 12H), 6.92 (d, 4H), 7.05 (d, 4H), 7.14–7.35 (m, 22H), 7.43–7.51 (m, 4H), 7.91 (d, 4H), 8.38 (d, 2H), 8.53 (s, 1H)

Example 5

Preparation of 3-[(4-carboxyphenyl)methylamino]4-valeramidobenzoic acid morpholide ([1]-(16)-1) (Compound No. 1)

The compound ([1]-(16)-1') (7.71 g) prepared in Example 3 was dissolved in tetrahydrofuran (200 ml), and 1N NaOH aqueous solution (38 ml) and distilled water (380 ml) were added. Then, the reaction mixture was stirred at room temperature for 6.5 hours. After methanol was evaporated from the reaction solution, the solution was adjusted to pH 5 with 1N HCl aqueous solution to obtain a precipitate. The precipitate was purified by silica gel column chromatography (Kieselgel 60=100 g, chloroform/methanol=10/1) to obtain the compound ([1]-(16)-1) (Compound No. 1) (5.79 g) as white foam.

Melting point: 109.0°–111.0° C.

$^1$H-NMR (500 MHz, $d_6$-DMSO) δ: 0.86 (t, 3H), 1.36 (sext, 2H), 1.63 (quint, 2H), 2.37 (t, 2H), 2.9–3.8 (br, 8H), 4.46 (d, 2H), 5.88 (t, 1H), 6.35 (s, 1H), 6.59 (d, 1H), 7.26 (d, 1H), 7.46 (d, 2H), 7.89 (d, 2H), 9.25 (s, 1H)

Example 6

Preparation of 3-[[2'-(1H-tetrazol-5-yl)biphenyl-4-yl]methylamino]-4-valeramidobenzoic acid morpholide ([1]-(16)-585) (Compound No. 585)

The compound ([1]-(16)-585') (5.00 g) prepared in Example 4 was dissolved in methanol (100 ml) and tetrahydrofuran (10 ml). After the mixture was cooled to −20° C., concentrated hydrochloric acid (30 ml) was slowly added dropwise. The reaction mixture was poured in a beaker containing sodium hydroxide (30.0 g), water (40 ml), and ice (100 g), and the insolubles were removed. After the organic solvent of the reaction solution was evaporated, the insolubles were further removed. The solution was adjusted to pH 4-5 with 1N HCl aqueous solution for precipitation to collect the precipitated crystals. The above procedure was repeated twice. The resulting white crystals were purified by silica gel column chromatography (Kieselgel 60=100 g, chloroform/methanol=10/1) to obtain the compound ([1]-(16)-585) (Compound No. 585) (4.09 g) as white foam.

Melting point: 131.0°–133.0° C.

$^1$H-NMR (500 MHz, $d_6$-DMSO) δ: 0.91 (t, 3H), 1.36 (sext, 2H), 1.63 (quint, 2H), 2.37 (t, 2H), 3.0–3.8 (br, 8H), 4.37 (d, 2H), 5.77 (t, 1H), 6.45 (s, 1H), 6.59 (d, 1H), 7.02 (d, 4H), 7.21–7.69 (m, 5H), 9.21 (s, 1H)

Example 7

Preparation of 3-[di-[2'-(1H-tetrazol-5-yl)biphenyl-4-yl]methylamino]-4-valeramidobenzoic acid morpholide ([1]-(16)-594) (Compound No. 594)

The compound ([1]-(16)-594') (10.0 g) prepared in Example 4 was dissolved in tetrahydrofuran (200 ml). After 12% HCl aqueous solution (50 ml) was added, the reaction mixture was stirred at room temperature for 6 hours. After the solvent was evaporated, 1N NaOH aqueous solution was added and the insolubles were removed. The solution was adjusted to pH 4-5 with 1N HCl aqueous solution to obtain a precipitate. The resulting crystals were purified by silica gel column chromatography (Kieselgel 60=75 g, chloroform/methanol=10/1) to obtain the compound ([1]-(16)-594) (Compound No. 594) (4.27 g) as white foam.

Melting point: 207.0°–210.0° C.

$^1$H-NMR (500 MHz, $d_6$-DMSO) δ: 0.83 (t, 3H), 1.26 (sext, 2H), 1.50 (quint, 2H), 2.31 (t, 2H), 2.8–3.9 (br, 8H), 4.10 (s, 4H), 6.9–7.1 (m, 6H), 7.29 (d, 4H), 7.48 (d, 2H), 7.5–7.7 (m, 6H), 7.82 (d, 1H), 9.03 (s, 1H)

Example 8

Preparation of 4-n-amylamino-3,5-dinitrobenzoic acid morpholide ([1]-(12)-593)

To a solution of 4-n-amylamino-3,5-dinitrobenzoic acid (23.80 g) in anhydrous tetrahydrofuran (360 ml), dicyclohexylcarbodiimide (21.47 g), 1-hydroxybenzotriazole (14.06 g), and morpholine (9.1 ml) were added to the solution. The mixture was stirred at room temperature for 14 hours. After the insolubles were filtered out and washed with tetrahydrofuran, the filtrate and the washing were combined and concentrated to obtain a reddish brown solid (51.04 g). The solid was recrystallized from a mixture of n-hexane (50 ml) and ethyl acetate (150 ml) to obtain the compound ([1]-(12)-593) (32.61 g) as yellowish orange needle crystals.

Melting point: 126.0°–129.0° C.

$^1$H-NMR (500 MHz, $d_6$-DMSO) δ: 0.85 (t, 3H), 1.24–1.32 (m, 4H), 1.60–1.63 (m, 2H), 2.94 (dt, 2H), 3.53 (bs, 4H), 3.61 (bs, 4H), 8.24 (t, 1H), 8.29 (s, 2H)

Example 9

Preparation of 4-(N-n-amyl-N-methyl)amino-3,5-dinitrobenzoic acid morpholide ([1]-(13)-593)

The compound ([1]-(12)-593) (5.00 g) prepared in Example 8 was dissolved in N,N-dimethylformamide (75 ml). To the solution, methyl iodide (9.69 g) and silver (I) oxide (6.33 g) were added, and the mixture was stirred at room temperature overnight. After the insolubles were filtered out, the reaction solution was poured into water (200 ml), and extracted with chloroform. The organic layer was washed with saturated brine, dried over anhydrous sodium sulfate, and concentrated under reduced pressure to obtain a crude product (8.21 g). The crude product was purified by silica gel column chromatography (Kieselgel 60, chloroform/ethyl acetate=6/1) to obtain the compound ([1]-(13)-593) (2.22 g) as orange oil. Further, the part including impurities was repurified to obtain the compound ([1]-(13)-593) (2.09 g)

$^1$H-NMR (500 MHz, CDCl$_3$) δ: 0.88 (t, 3H), 1.20–1.35 (m, 4H), 1.99 (bquint, 2H), 2.84 (s, 3H), 2.93 (t, 2H), 3.64–3.73 (br, 8H), 7.91 (s, 2H)

Example 10

Preparation of 4-(N-n-amyl-N-methyl)amino-3,5-diaminobenzoic acid morpholide ([1]-(14)-593)

The compound ([1]-(13)-593) (2.22 g) prepared in Example 9 was dissolved in methanol/ethyl acetate (1/9) (22 ml). To the solution, tin (II) chloride dihydrate (13.17 g) were added and the mixture was heated to 80° C. and stirred for 30 minutes under an argon gas stream. The reaction solution was poured into water (10 ml), adjusted to approximately pH 7 with 5% sodium hydrogencarbonate aqueous solution and sodium carbonate, and the precipitated insolubles were filtered out through celite. The organic layer was concentrated, and the aqueous layer was extracted with chloroform. The organic layer was washed with saturated brine, and dried over anhydrous sodium sulfate to obtain a crude product (1.02 g).

The crude product was purified by silica gel column chromatography (Kieselgel 60, chloroform/methanol=15/1) to obtain the compound ([1]-(14)-593) (0.84 g) as colorless oil.

$^1$H-NMR (500 MHz, CDCl$_3$) δ: 0.88 (t, 3H), 1.22–1.40 (m, 4H), 1.48 (bquint, 2H), 2.76 (s, 3H), 2.97 (t, 2H), 3.48–4.03 (br, 12H), 6.10 (s, 2H)

Example 11

Preparation of 3-amino-4-(N-n-amyl-N-methyl)amino-5-(diphenylacetamido)benzoic acid morpholide ([1]-(15)-593)

To a solution of N,N-dicyclohexylcarbodiimide (0.54 g), 1-hydroxybenzotriazole (0.35 g), and diphenylacetic acid (0.56 g) in acetonitrile (5 ml), a solution of the compound ([1]-(14)-593) (0.80 g) prepared in Example 10 in acetonitrile (4 ml). The mixture was stirred overnight. The insolubles were filtered through celite, and the filtrate was concentrated. The residue was dissolved in chloroform, and washed with saturated sodium hydrogencarbonate aqueous solution. The chloroform layer was dried over anhydrous sodium sulfate, and concentrated under reduced pressure to obtain a crude product (1.27 g).

The crude product was purified by silica gel column chromatography (Kieselgel 60, n-hexane/ethyl acetate=1/4) to obtain the compound ([1]-(15)-593) (0.68 g) as light yellow crystals.

Melting point: 72.0°–75.0° C.

$^1$H-NMR (500 MHz, CDCl$_3$) δ: 0.85 (t, 3H), 0.95–1.15 (m, 4H), 1.20 (quint, 2H), 2.39 (s, 3H), 2.50–2.60 (m, 1H), 2.70–2.76 (m, 1H), 3.54–3.72 (br, 10H), 5.14 (s, 1H), 6.47 (s, 1H), 7.28–7.39 (m, 10H), 7.95 (s, 1H), 8.94 (s, 1H)

Example 12

Preparation of 4-(N-n-amyl-N-methyl)amino-5-(diphenylacetamido)-3-[[2'-(1-triphenylmethyltetrazol-5-yl)biphenyl-4-yl]methylamino]benzoic acid morpholide ([1]-(16)-593')

The compound ([1]-(15)-593) (0.25 g) prepared in Example 11 was dissolved in benzene (10 ml), and N-(triphenylmethyl)-5-[4'-(bromomethyl)biphenyl-2-yl] tetrazole (0.42 g) and diisopropylethylamine (0.63 g) were added to the solution. The mixture was heated to 80° C. and stirred for 2 days under an argon gas stream. Diisopropylethylamine (0.13 g) were added to the reaction mixture, and the mixture was further heated and stirred for 3 days. The solvent was concentrated under reduced pressure, and the residue was extracted with chloroform. The organic layer was dried over anhydrous sodium sulfate, and concentrated under reduced pressure to obtain a crude product (0.76 g). The crude product was purified by silica gel column chromatography (Kieselgel 60, chloroform/ethyl acetate=6/1) to obtain the compound ([1]-(16)-593') (0.22 g) as light yellow crystals.

Melting point: 112.0°–115.0° C.

$^1$H-NMR (500 MHz, CDCl$_3$) δ: 0.83 (t, 3H), 1.04–1.15 (m, 4H), 1.18 (bquint, 2H), 2.35 (s, 3H), 2.45–2.55 (m, 1H), 2.60–2.70 (m, 1H), 3.53–3.71 (br, 9H), 4.21 (s, 2H), 5.15 (s, 1H), 6.44 (s, 1H), 6.92–7.18 (m, 10H), 7.21–7.44 (m, 20H), 7.45–7.51 (m, 2H), 7.89–7.92 (m, 2H), 8.60 (s, 1H)

Example 13

Preparation of 4-(N-n-amyl-N-methyl)amino-5-(diphenylacetamido)-3-[[2'-(1H-tetrazol-5-yl)biphenyl-4-yl]methylamino]benzoic acid morpholide ([1]-(16)-593) (Compound No. 593)

The compound ([1]-(16)-593') (0.15 g) prepared in Example 12 was dissolved in tetrahydrofuran (3 ml), and 12% HCl aqueous solution (0.75 ml) was added to the solution. The mixture was stirred at room temperature overnight. The reaction solution was adjusted to pH 7 with 5% sodium carbonate aqueous solution, and extracted with ethyl acetate. The organic layer was washed with saturated brine, and concentrated under reduced pressure to obtain a crude product (0.17 g). The crude product was purified by silica gel column chromatography (Kieselgel 60, ethyl acetate) to obtain the compound ([1]-(16)-593) (Compound No. 593) (0.050 g).

Melting point: 122.0°–125.0° C.

$^1$H-NMR (500 MHz, CDCl$_3$) δ: 0.86 (t, 3H), 1.12 (bs, 4H), 1.25 (bquint, 2H), 2.46 (s, 3H), 2.55–2.65 (m, 1H), 2.65–2.75 (m, 1H), 3.52–3.71 (br, 9H), 4.45 (s, 2H), 5.16 (s, 1H), 6.07 (s, 1H), 7.06 (d, 2H), 7.17 (d, 2H), 7.30–7.41 (m, 11H), 7.45–7.60 (m, 3H), 7.80 (s, 1H), 7.97 (d, 1H), 8.52 (s, 1H)

Example 14

Preparation of 4-[(4-chloro-3,5-dinitrobenzene)sulfonyl]morpholine ([2]-(22)-598)

Morpholine (0.89 g) was dissolved in dichloromethane (20 ml), and triethylamine (1.41 ml) was added. The mixture was cooled on ice. To the solution, a solution of 3,5-dinitro-4-chloro-benzenesulfonyl chloride ([2]-(21)-598) (2.56 g) in dichloromethane (15 ml) was added dropwise. The mixture was stirred for 4.5 hours, and extracted with chloroform. The organic layer was dried over anhydrous sodium sulfate, and the solvent was evaporated. The crude product was purified by silica gel column chromatography (Kieselgel 60=50 g, chloroform) to obtain the compound ([2]-(22)-598) (0.32 g).

$^1$H-NMR (500 MHz, CDCl$_3$) δ: 3.15 (t, 4H), 3.80 (t, 4H), 8.30 (s, 2H)

Example 15

Preparation of 4-[(4-n-amylamino-3,5-dinitrobenzene)sulfonyl]morpholine ([2]-(23)-598)

A mixture of the compound ([2]-(22)-598) (0.26 g) prepared in Example 14, acetone (5 ml), amylamine (0.1 ml), and water (5 ml) was heated under reflux overnight. The solvent was evaporated from the reaction mixture, and the residue was extracted with chloroform. The organic layer was dried over anhydrous sodium sulfate, and the solvent was evaporated. The crude product was purified by silica gel column chromatography (Kieselgel 60=50 g, chloroform) to obtain the compound ([2]-(23)-598) (0.27 g).

$^1$H-NMR (500 MHz, CDCl$_3$) δ: 0.93 (t, 3H), 1.34–1.40 (m, 4H), 1.73 (quint, 2H), 3.05 (t, 2H), 3.08 (t, 4H), 3.78 (t, 4H), 8.47 (s, 2H), 8.79 (bs, 1H)

Example 16

Preparation of 4-[[4-(N-n-amyl-N-methyl)amino-3,5-dinitrobenzene]sulfonyl]morpholine ([2]-(24)-598)

The compound ([2]-(23)-598) (1.59 g) prepared in Example 15 was dissolved in N,N-dimethylformamide (15 ml), and methyl iodide (2.81 g) and silver (I) oxide (1.84 g) were added. The mixture was stirred overnight. The reaction solution was filtered through celite, and was washed with ethyl acetate, 1N HCl aqueous solution and then saturated brine. The organic layer was dried over anhydrous sodium sulfate, and the solvent was evaporated. The crude product was purified by silica gel column chromatography (Kieselgel 60=85 g, chloroform) to obtain the compound ([2]-(24)-598) (1.32 g) as a yellow solid.

$^1$H-NMR (500 MHz, CDCl$_3$) δ: 0.89 (t, 3H), 1.2–1.33 (m, 4H), 1.65 (quint, 2H), 2.88 (s, 3H), 2.98 (bt, 2H), 3.09 (t, 4H), 3.78 (t, 4H), 8.12 (s, 2H)

Example 17

Preparation of 4-[[3,5-diamino-4-(N-n-amyl-N-methyl)aminobenzene]sulfonyl]morpholine ([2]-(25)-598)

To a solution of the compound ([2]-(24)-598) (2.16 g) prepared in Example 16 in ethyl acetate (70 ml), tin (II)

chloride dihydrate (11.7 g) was added. The mixture was reacted at 90° C. for 30 minutes under a nitrogen gas stream. To the reaction solution, water (10 ml) was added, and sodium hydrogencarbonate was added to neutralize the solution. The solution was filtered through celite, and washed with ethyl acetate. The filtrate was washed with brine. The organic layer was dried over anhydrous sodium sulfate, and the solvent was evaporated. The crude product (2.12 g) was purified by silica gel column chromatography (Kieselgel 60=125 g, chloroform) to obtain the compound ([2]-(25)-598) (0.57 g)

$^1$H-NMR (500 MHz, CDCl$_3$) δ: 0.89 (t, 3H), 1.20–1.35 (m, 4H), 1.49 (quint, 2H), 2.77 (s, 3H), 2.99 (bt, 2H), 3.03 (t, 4H), 3.74 (t, 4H), 4.04 (s, 4H), 6.44 (s, 2H)

Example 18

Preparation of 4-[[3-amino-4-(N-n-amyl-N-methyl) amino-5-(diphenylacetamido)benzene]sulfonyl] morpholine ([2]-(26)-598)

To a solution of diphenylacetic acid (0.41 g) in tetrahydrofuran (3 ml), dicyclohexylcarbodiimide (0.37 g) and 1-hydroxybenzotriazole (0.26 g) were added. After 10 minutes, a solution of the compound ([2]-(25)-598) prepared in Example 17 in chloroform (6 ml) was added dropwise, and the mixture was stirred at room temperature overnight. The insolubles were filtered, and the filtrate was concentrated. To the concentrate, ethyl acetate (30 ml) was added. The organic layer was washed with 1N NaOH aqueous solution, and dried over anhydrous sodium sulfate. Then the solvent was evaporated. The crude product was purified by silica gel column chromatography (Wako-gel C300=75 g, chloroform) to obtain a white solid ([2]-(26)-598) (0.75 g)

$^1$H-NMR (500 MHz, CDCl$_3$) δ: 0.86 (t, 3H), 1.00–1.15 (br, 4H), 1.22 (bquint, 2H), 2.40 (s, 3H), 2.57–2.59 (m, 1H), 2.60–2.70 (m, 1H), 3.09 (bt, 4H), 3.74 (t, 4H), 3.81 (s, 2H), 5.15 (s, 1H), 6.79 (d, 1H), 7.29–7.39 (m, 10H), 8.28 (s, 1H), 8.88 (s, 1H)

Example 19

Preparation of 4-[[3-amino-4-(N-n-amyl-N-methyl) amino-5-(3-phenylpropionamido)benzene]sulfonyl] morpholine ([2]-(26)-599)

To a solution of 3-phenylpropionic acid (3.32 g) in N,N-dimethylformamide (30 ml), dicyclohexylcarbodiimide (3.96 g) and 1-hydroxybenzotriazole (2.99 g) were added. After 2 hours, a solution of the compound ([2]-(25)-598) (6.84 g) prepared in Example 17 in N,N-dimethylformamide (15 ml) was added dropwise. After the mixture was stirred at room temperature overnight, the insolubles were filtered, and the filtrate was concentrated. To the concentrate, ethyl acetate (30 ml) was added, and the organic layer was washed with 1N NaOH aqueous solution, and dried over anhydrous sodium sulfate. Then the solvent was evaporated. The crude product was purified by silica gel column chromatography (Kieselgel 60=250 g, chloroform) to obtain a white solid ([2]-(26)-599) (7.02 g)

$^1$H-NMR (500 MHz, CDCl$_3$) δ: 0.88 (t, 3H), 1.26–1.43 (m, 6H), 2.67 (s, 3H) 2.73 (t, 2H), 2.90–3.00 (m, 2H), 3.06 (t, 2H), 3.09 (t, 4H), 3.74 (t, 4H), 3.90 (s, 2H), 6.79 (d, 1H), 7.19–7.31 (m, 5H), 8.20 (s, 1H), 8.71 (s, 1H)

Example 20

Preparation of 4-[[4-(N-n-amyl-N-methyl)amino-3-[(4-methoxycarbonylphenyl)methyl]amino-5-(diphenylacetamido)benzene]sulfonyl]morpholine ([2]-(27)-598')

A mixture of the compound ([2]-(26)-598) (0.08 g) prepared in Example 18, methyl 4-bromomethylbenzoate (0.07 g), triethylamine (0.04 ml), and toluene (5 ml) was stirred at 80° C. for 48 hours under a nitrogen gas atmosphere. The solvent was evaporated, and the residue was purified by silica gel column chromatography (Wako-gel C300=25 g, chloroform) to obtain a white solid ([2]-(27)-598') (0.07 g).

$^1$H-NMR (500 MHz, CDCl$_3$) δ: 0.86 (t, 3H), 1.00–1.15 (m, 4H), 1.22 (bquint, 2H), 2.42 (s, 3H), 2.50–2.60 (m, 1H), 2.61–2.64 (m, 1H), 2.81 (bs, 4H), 3.62 (t, 4H), 3.90 (s, 3H), 4.44 (d, 2H), 4.63 (bt, 1H), 5.15 (s, 1H), 6.57 (s, 1H), 7.28–7.39 (m, 12H), 7.98 (d, 2H), 8.18 (s, 1H), 8.46 (s, 1H)

Example 21

Preparation of 4-[[4-(N-n-amyl-N-methyl)amino-3-[(4-carboxylphenyl)methyl]amino-5-(diphenylacetamido)benzene]sulfonyl]morpholine ([2]-(27)-598) (Compound No. 598)

The compound ([2]-(27)-598') (0.06 g) prepared in Example 20 was dissolved in methanol (5 ml), and 1N NaOH aqueous solution (0.3 ml) was added. The mixture was stirred overnight. Further, 1N NaOH aqueous solution (0.2 ml) was added, and the mixture was stirred for 4 days. The reaction solution was concentrated, and adjusted to pH 1 with 1N HCl aqueous solution. The precipitated solid was filtered out. The solid was treated by a preparative thin layer chromatography (Merck 13895, chloroform/methanol=10/1) to obtain a white solid ([2]-(27)-598) (Compound No. 598) (0.03 g).

$^1$H-NMR (500 MHz, CDCl$_3$) δ: 0.87 (t, 3H), 1.10 (bs, 4H), 1.23 (bquint, 2H), 2.43 (s, 3H), 2.50–2.60 (m, 1H), 2.60–2.70 (m, 1H), 2.81 (bs, 4H), 3.62 (t, 4H), 4.47 (bd, 2H), 4.65 (bs, 1H), 5.16 (s, 1H), 6.56 (d, 1H), 7.30–7.41 (m, 12H), 8.03 (d, 2H), 8.19 (s, 1H), 8.45 (s, 1H)

Example 22

Preparation of 4-[[4-(N-n-amyl-N-methyl)amino-3-[[2'-(1-triphenylmethyltetrazol-5-yl)biphenyl-4-yl]methyl]amino-5-(3-phenylpropionamido)benzene]sulfonyl]morpholine ([2]-(27)-599')

A mixture of the compound ([2]-(26)-599) (7.01 g) prepared in Example 19, diisopropylethylamine (7.60 g), N-(triphenylmethyl)-5-[4'-(bromomethyl)biphenyl-2-yl] tetrazole (12.6 g), and toluene (150 ml) was stirred at 80° C. for 4 days under a nitrogen gas atmosphere. After the reaction mixture was concentrated, the mixture was extracted with chloroform. The organic layer was dried, and concentrated. The crude product (20.1 g) was purified by silica gel column chromatography (Kieselgel 60=300 g, chloroform) to obtain a white solid ([2]-(27)-599') (3.13 g).

$^1$H-NMR (500 MHz, CDCl$_3$) δ: 0.85 (t, 3H), 1.23–1.31 (m, 4H), 1.35–1.50 (m, 2H), 2.66 (s, 3H), 2.69 (t, 2H), 2.93 (bt, 4H), 2.98 (t, 2H), 3.07 (dd, 2H), 3.65 (t, 4H), 4.27 (d, 2H), 4.41 (bs, 1H), 6.23 (d, 1H), 6.94 (d, 4H), 7.05–7.46 (m, 21H), 7.47–7.52 (m, 2H), 7.90 (d, 1H), 8.10 (s, 1H), 8.35 (s, 1H)

Example 23

Preparation of 4-[[4-(N-n-amyl-N-methyl)amino-3-[[2'-(1H-tetrazol-5-yl) biphenyl-4-yl]methyl]amino-5-(3-phenylpropionamido)benzene]sulfonyl] morpholine ([2]-(27)-599) (Compound No. 599)

The compound ([2]-(27)-599') (3.13 g) prepared in Example 22 was dissolved in tetrahydrofuran (35 ml), and concentrated hydrochloric acid (17 ml) was added dropwise to the solution. After the mixture was stirred at room temperature for 4 hours, the mixture was adjusted to pH 7 with 10N NaOH aqueous solution, and extracted with chloroform. After the organic layer was dried over anhydrous sodium sulfate, the concentrated crude product was purified by silica gel column chromatography (Wako-gel C300=100 g, chloroform/methanol=10/1) to obtain a white solid ([2]-(27)-599) (Compound No. 599) (1.43 g).

$^1$H-NMR (500 MHz, CDCl$_3$) δ: 0.89 (t, 3H), 1.30–1.50 (m, 4H), 1.40–1.50 (m, 2H), 2.69 (t, 2H), 2.68 (t, 2H), 2.74 (s, 3H), 2.88 (bs, 4H), 2.96–3.04 (m, 2H), 3.07 (t, 2H), 3.67 (t, 4H), 4.49 (d, 2H), 4.82 (bs, 1H), 6.47 (d, 1H), 7.15 (d, 2H), 7.21–7.31 (m, 6H), 7.47–7.62 (m, 2H), 7.93 (d, 2H), 8.09 (s, 1H), 8.30 (s, 1H)

Example 24

Preparation of 4-[(4-chloro-3-nitrobenzene)sulfonyl] morpholine ([2]-(22)-596)

To a solution of 4-chloro-3-nitrobenzenesulfonyl chloride (0.26 g) in dichloromethane (1.0 ml), morpholine (1.80 g) and dichloromethane (1.0 ml) were added at 0° C., and dissolved. The reaction solution was stirred at room temperature for 5 hours. Distilled water was added to the reaction solution, and the reaction mixture was extracted with dichloromethane. The organic layer was dried over anhydrous sodium sulfate, and concentrated to obtain yellow crystals. The crystals were purified by silica gel column chromatography (Kieselgel 60, hexane/ethyl acetate=1/1) to obtain the compound ([2]-(22)-596) (0.29 g) as light yellow crystals.

Melting point: 146.0°–148.0° C.

$^1$H-NMR (500 MHz, CDCl$_3$) δ: 3.08 (t, 4H), 3.78 (t, 4H), 7.77 (d, 1H), 7.88 (dd, 1H), 8.23 (d, 1H)

Example 25

Preparation of 4-[(4-n-amylamino-3-nitrobenzene) sulfonyl]morpholine ([2]-(23)-596)

To a mixture of the compound ([2]-(22)-596) (9.62 g) prepared in Example 24, tetrahydrofuran (10 ml), and ethanol (20 ml), a solution of n-amylamine (5.47 g) in ethanol (20 ml) was added at room temperature, and the mixture was heated under reflux at 70° C. for 4 hours. The reaction mixture was concentrated under reduced pressure, and extracted with chloroform. The organic layer was washed with distilled water, dried over anhydrous sodium sulfate, and concentrated under reduced pressure to obtain a crude product (12.36 g). The crude product was purified by silica gel column chromatography (Kieselgel 60, hexane/ethyl acetate=2/1) to obtain the compound ([2]-(23)-596) (11.38 g) as yellow crystals.

Melting point: 74.5°–76.0° C.

$^1$H-NMR (500 MHz, CDCl$_3$) δ: 0.95 (t, 3H), 1.40–1.52 (m, 4H), 1.78 (quint, 2H), 3.03 (t, 4H), 3.36 (dd, 2H), 3.76 (t, 4H), 6.96 (d, 1H), 7.73 (dd, 1H), 8.40 (bs, 1H), 8.58 (d, 1H)

Example 26

Preparation of 4-[[4-(N-n-amyl-N-methyl)amino-3-nitrobenzene]sulfonyl]morpholine ([2]-(24)-596)

The compound ([2]-(23)-596) (0.40 g) prepared in Example 25 was dissolved in N,N-dimethylformamide (2 ml), and methyl iodide (0.79 g) and silver (I) oxide (0.52 g) were added. The mixture was stirred at room temperature overnight. After the insolubles were filtered out, the filtrate was concentrated under reduced pressure, and the residue was extracted with chloroform. The organic layer was washed with distilled water, dried over anhydrous sodium sulfate, and concentrated under reduced pressure. The crude product was purified by silica gel column chromatography (Kieselgel 60, hexane/ethyl acetate=1/1) to obtain the compound ([2]-(24)-596) (0.47 g) as yellow crystals.

Melting point: 99.5°–101.0° C.

$^1$H-NMR (500 MHz, CDCl$_3$) δ: 0.92 (t, 3H), 1.25–1.38 (m, 4H), 1.68 (quint, 2H), 2.89 (s, 3H), 3.02 (t, 4H), 3.28 (t, 2H), 3.76 (t, 4H), 7.08 (d, 1H), 7.65 (dd, 1H), 8.12 (d, 1H)

Example 27

Preparation of 4-[[3-amino-4-(N-n-amyl-N-methyl) aminobenzene]sulfonyl]morpholine ([2]-(25)-596)

A mixture of the compound ([2]-(24)-596) (3.57 g) prepared in Example 26, ethyl acetate (52.9 ml), methanol (8.9 ml), and tin (II) chloride dihydrate (10.9 g) was heated under reflux at 80° C. for 1 hour under a nitrogen gas stream. The reaction solution was cooled, and neutralized (pH= approximately 6) with 5% sodium carbonate aqueous solution. The solution was filtered through celite, and concentrated. The residue was extracted with ethyl acetate. The organic layer was washed with distilled water, and dried over anhydrous sodium sulfate. The solvent was evaporated. The crude product (3.17 g) was purified by silica gel column chromatography (Kieselgel 60, hexane/ethyl acetate=1/1) to obtain the compound ([2]-(25)-596) (0.31 g) as colorless crystals.

Melting point: 83.0°–84.5° C.

$^1$H-NMR (500 MHz, CDCl$_3$) δ: 0.89 (t, 3H), 1.28–1.35 (m, 4H), 1.52 (quint, 2H), 2.67 (s, 3H), 2.88 (t, 2H), 3.00 (t, 4H), 3.74 (t, 4H), 4.14 (s, 2H), 7.04–7.10 (m, 3H)

Example 28

Preparation of 4-[[4-(N-n-amyl-N-methyl)amino-3-[(4-methoxycarbonylphenyl)methyl]aminobenzene] sulfonyl]morpholine ([2]-(27)-596')

To a solution of the compound ([2]-(25)-596) (0.10 g) prepared in Example 27 and methyl 4-bromomethylbenzoate (0.10 g) in dichloromethane (3 ml), diisopropylethylamine (0.57 g) was added, and the reaction mixture was heated under reflux at 40° C. for 2 days. The reaction solution was concentrated under reduced pressure, and the residue was extracted with chloroform. The organic layer was washed with distilled water, dried over anhydrous sodium sulfate, and concentrated under reduced pressure to obtain yellow oil. The oil was purified by silica gel column chromatography (Kieselgel 60, hexane/ethyl acetate=4/1) to obtain the compound ([2]-(27)-596') (0.13 g) as yellow oil.

$^1$H-NMR (500 MHz, CDCl$_3$) δ: 0.88 (t, 3H), 1.24–1.31 (m, 4H), 1.51 (bt, 2H), 2.68 (s, 3H), 2.72 (t, 4H), 2.89 (t, 2H), 3.61 (t, 4H), 3.90 (s, 3H), 4.48 (d, 2H), 5.36 (s, 1H), 6.70 (d, 1H), 7.04 (dd, 1H), 7.08 (d, 1H), 7.41 (d, 2H), 8.00 (d, 2H)

Example 29

Preparation of 4-[[4-(N-n-amyl-N-methyl)amino-3-[(4-carboxyphenyl)methyl]aminobenzene]sulfonyl] morpholine ([2]-(27)-596) (Compound No. 596)

To a solution of the compound ([2]-(27)-596') (0.13 g) prepared in Example 28 in dimethoxyethane (12 ml), 0.1N NaOH aqueous solution (5.2 ml) was added, and the reaction mixture was stirred at room temperature overnight. The reaction mixture was adjusted to pH 7 with 0.1N HCl aqueous solution, and concentrated under reduced pressure to obtain yellow oil (0.15 g). The oil was purified by silica gel column chromatography (Kieselgel 60, chloroform/methanol=10/1) to obtain the compound ([2]-(27)-596) (Compound No. 596) (0.09 g) as colorless crystals.

Melting point: 182.5°–186.0° C.

$^1$H-NMR (500 MHz, CD$_3$OD) δ: 0.89 (t, 3H), 1.33 (bquint, 4H), 1.55 (bt, 2H), 2.49 (t, 4H), 2.73 (s, 3H), 3.00 (t, 2H), 3.51 (t, 4H), 4.55 (s, 2H), 6.59 (d, 1H), 6.96 (dd, 1H), 7.16 (d, 1H), 7.45 (d, 2H), 7.95 (d, 2H)

Example 30

Preparation of 4-[[4-(N-n-amyl-N-methyl)amino-3-[[2'-(1-triphenylmethyltetrazol-5-yl)biphenyl-4-yl]methyl]aminobenzene]sulfonyl]morpholine ([2]-(27)-595')

To a solution of the compound ([2]-(25)-596) (0.15 g) prepared in Example 27 and N-(triphenylmethyl)-5-[4'-(bromomethyl)biphenyl-2-yl]tetrazole (0.50 g) in benzene (5 ml), diisopropylethylamine (0.59 g) was added, and the reaction mixture was refluxed at 80° C. for 6 days. The reaction mixture was concentrated under reduced pressure, and the residue was extracted with chloroform. The organic layer was washed with distilled water, dried over anhydrous sodium sulfate, and concentrated under reduced pressure to obtain yellow oil (0.69 g). The oil was purified by silica gel column chromatography (Kieselgel 60, chloroform/ethyl acetate=30/1) to obtain the compound ([2]-(27)-595') (0.21 g) as yellow oil.

Example 31

Preparation of 4-[[4-(N-n-amyl-N-methyl)amino-3-[[2'-(1H-tetrazol-5-yl)biphenyl-4-yl]methyl]aminobenzene]sulfonyl]morpholine ([2]-(27)-595) (Compound No. 595)

To a solution of the compound ([2]-(27)-595') (0.39 g) prepared in Example 30 in tetrahydrofuran (7.7 ml), 12% HCl aqueous solution (1.9 ml) was further added, and the reaction mixture was stirred at room temperature for 5 hours. The reaction mixture was adjusted to pH 5 with 5% sodium carbonate aqueous solution, and concentrated under reduced pressure. The residue was extracted with ethyl acetate. The organic layer was washed with distilled water, dried over anhydrous sodium sulfate, and concentrated under reduced pressure to obtain yellow oil (0.38 g). The oil was purified by silica gel column chromatography (Kieselgel 60, chloroform/methanol=20/1) to obtain the compound ([2]-(27)-595) (Compound No. 595) (0.19 g) as white foam.

$^1$H-NMR (500 MHz, CDCl$_3$) δ: 0.89 (t, 3H), 1.32 (bquint, 4H), 1.55 (bs, 2H), 2.71 (s, 3H), 2.76 (s, 4H), 2.92 (t, 2H), 3.70 (t, 4H), 4.51 (d, 2H), 5.53 (t, 1H), 6.63 (s, 1H), 7.05–7.09 (m, 2H), 7.14 (d, 2H), 7.29 (d, 1H), 7.47–7.54 (m, 2H), 7.60–7.63 (m, 1H), 7.90 (d, 1H)

Example 32

Preparation of (3-nitro-4-valeramido)benzoic acid diethylamide ([1]-(12)-586)

In dry N,N-dimethylformamide (300 ml), 3-nitro-4-valeramidobenzoic acid (19.35 g) was dissolved, and 1-ethyl-3-(3-dimethylaminopropyl)carbodiimide hydrochloride (16.74 g), 1-hydroxybenzotriazole (11.80 g), diethylamine (11.88 g), and triethylamine (8.83 g) were added successively. The reaction mixture was stirred at room temperature for 36 hours, and the solvent was evaporated in a bath at 80° C. under reduced pressure to a solution volume of approximately 100 ml. After ethyl acetate (400 ml) was added to the residue, the mixture was washed with 1N HCl aqueous solution (100 ml), water (200 ml), saturated sodium carbonate aqueous solution (50 ml), and water (150 ml) successively. The organic layer was dried over anhydrous magnesium sulfate to obtain the compound ([1]-(12)-586) (23.64 g) as light yellow oil.

$^1$H-NMR (500 MHz, CDCl$_3$) δ: 0.90 (t, 3H), 1.14 (bs, 6H), 1.36 (sext, 2H), 1.68 (quint, 2H), 2.44 (t, 2H), 3.23 (bs, 2H), 3.45 (bs, 2H), 7.59 (d, 1H), 8.21 (s, 1H), 8.77 (d, 1H), 10.33 (s, 1H)

Example 33

Preparation of (3-amino-4-valeramido)benzoic acid diethylamide ([1]-(14)-586)

The compound ([1]-(12)-586) (23.64 g) prepared in Example 32 was dissolved in ethanol (800 ml). After the solution was stirred at 60° C. for 30 minutes, a suspension of 10% Pd/C (0.88 g) in ethanol (2 ml) was added to the solution, and hydrazine monohydrate (7.15 ml) was added dropwise over 5 minutes. After the solution was stirred at the same temperature for 30 minutes, it was cooled, and the insolubles were filtered out through celite. The filtrate was concentrated to obtain a colorless solid (20.69 g). The solid was dissolved in chloroform (300 ml), washed with water (100 ml), dried over anhydrous magnesium sulfate, and concentrated to obtain the compound ([1]-(14)-586) (19.96 g) as a colorless solid.

Melting point: 121.0°–123.0° C.

$^1$H-NMR (500 MHz, CDCl$_3$) δ: 0.96 (t, 3H), 1.06 (bs, 3H), 1.23 (bs, 3H), 1.42 (sext, 2H), 1.72 (quint, 2H), 2.44 (t, 2H), 3.24 (bs, 2H), 3.51 (bs, 2H), 6.47 (d, 1H), 6.53 (s, 1H), 6.87 (d, 1H), 8.83 (s, 1H)

Example 34

Preparation of [3-[[2'-(1-triphenylmethyltetrazol-5-yl)biphenyl-4-yl]methylamino]-4-valeramido] benzoic acid diethylamide ([1]-(16)-586')

The compound ([1]-(14-586) (9.64 g) prepared in Example 33 was dissolved in chloroform (150 ml). N-(triphenylmethyl)-5-[4'-(bromomethyl)biphenyl-2-yl] tetrazole (20.23 g) and diisopropylethylamine (42.67 g) were added to the solution, and the reaction mixture was heated to the reflux temperature over 10 minutes. After the mixture was heated under reflux with stirring for 2.5 hours and then cooled, chloroform (300 ml) was added to the mixture and the mixture was washed with water (250 ml), dried over anhydrous magnesium sulfate, and concentrated to obtain colorless foam (36.22 g). The product was purified by silica gel column chromatography (Kieselgel 60=1200 g, chloroform/ethyl acetate=3/1) to obtain the compound ([1]-(16)-586') (17.75 g) as colorless foam.

Melting point: 100.0°–105.0° C.

$^1$H-NMR (500 MHz, CDCl$_3$) δ: 0.90 (bs, 3H), 0.91 (t, 3H), 1.20 (bs, 3H), 1.38 (sext, 2H), 1.70 (quint, 2H), 2.38 (t, 2H), 3.14 (bs, 2H), 3.47 (bs, 2H), 4.14 (bs, 2H), 4.46 (bs, 1H), 6.51 (bs, 1H), 6.54 (d, 1H), 6.92–6.95 (m, 7H), 7.02 (d, 1H), 7.07–7.34 (m, 13H), 7.43–7.50 (m, 2H), 7.89 (d, 1H), 8.22 (s, 1H)

Example 35

Preparation of [3-[[2'-(1H-tetrazol-5-yl)biphenyl-4-yl]methylamino]-4-valeramido]benzoic acid diethylamide ([1]-(16)-586) (Compound No. 586)

While maintaining at −20° C. to −10° C., concentrated hydrochloric acid (80 ml) was added dropwise over 20 minutes to a solution of the compound ([1]-(16)-586') (5.26 g) prepared in Example 34, methanol (10 ml), and THF (200 ml). The mixture was further stirred at the same temperature for 30 minutes, and poured into a solution of ice (250 g), sodium hydroxide (56 g), and water (200 ml). The mixture was adjusted to pH 9 with concentrated hydrochloric acid, and the precipitated viscous product was filtered out. The filtrate was filtered through celite, and adjusted to pH 3 with concentrated hydrochloric acid. The precipitated solid was filtered to obtain the compound (1.93 g) as a colorless solid. To the above viscous product which had been filtered out, 1N NaOH aqueous solution was added to pH 10. After water (1500 ml) was added, the solution was filtered through celite. The filtrate was adjusted to pH 4, and the precipitated solid was filtered out to obtain the compound ([1]-(16)-586) (Compound No. 586) (1.31 g) (3.24 g in total) as a colorless solid.

Melting point: 137.0°–140.0° C.

$^1$H-NMR (500 MHz, $d_6$-DMSO) δ: 0.81 (bs, 3H), 0.91 (t, 3H), 1.06 (bs, 3H),1.35 (sext, 2H), 1.60 (quint, 2H), 2.37 (t, 2H), 3.03 (bs, 2H), 3.32 (bs, 2H), 4.35 (s, 2H), 5.78 (bs, 1H), 6.38 (s, 1H), 6.50 (d, 1H), 7.05 (d, 1H), 7.21 (d, 1H), 7.30 (d, 1H), 7.50–7.69 (m, 4H), 9.25 (s, 1H)

Example 36

Preparation of 3-hydroxy-4-nitrobenzoic acid morpholide ([3]-(32)-587)

To a solution of 3-hydroxy-4-nitrobenzoic acid (10.00 g) in dry N,N-dimethylformamide (150 ml), 1-ethyl-3-(3-dimethylaminopropyl)carbodiimide hydrochloride (12.56 g), 1-hydroxybenzotriazole (8.86 g), triethylamine (7.18 g), and morpholine (5.71 g) were added successively. A mixture was stirred at room temperature for 23 hours, and the solvent was evaporated in a bath at 80° C. under reduced pressure to a solution volume of approximately 100 ml. Ethyl acetate (400 ml) was added to the residue, and the mixture was washed with 1N HCl aqueous solution (100 ml), water (200 ml), saturated sodium carbonate aqueous solution (50 ml), and water (150 ml). The organic layer was dried over anhydrous magnesium sulfate, and concentrated to obtain the compound ([3]-(32)-587) (7.89 g) as a yellow solid.

Melting point: 110.0°–115.0° C.

$^1$H-NMR (500 MHz, CDCl$_3$) δ: 3.39 (bs, 2H), 3.64 (bs, 2H), 3.79 (bs, 4H), 7.01 (d, 1H), 7.18 (s, 1H), 8.17 (d, 1H), 10.61 (s, 1H)

Example 37

Preparation of 3-[[2'-(1-triphenylmethyltetrazol-5-yl)biphenyl-4-yl]methyloxy]-4-nitrobenzoic acid morpholide ([3]-(33)-587)

The compound ([3]-(32)-587) (0.99 g) prepared in Example 36 was dissolved in dry N,N-dimethylformamide (19 ml), and 50% sodium hydride (0.20 g) was added to the solution. The mixture was stirred at room temperature for 15 minutes. A solution of N-(triphenylmethyl)-5-[4'-(bromomethyl)biphenyl-2-yl]tetrazole (2.19 g) in N,N-dimethylformamide (6.5 ml) was added to the solution. The mixture was stirred at room temperature for 39 hours. The reaction mixture was added to water (50 ml), and extracted with chloroform (100 ml). The organic layer was washed, dried over anhydrous sodium sulfate, and concentrated to obtain the compound (2.72 g) as a light yellow solid. The product was purified by silica gel column chromatography (Kieselgel 60=190 g, chloroform/ethyl acetate=7/3) to obtain the compound ([3]-(33)-587) (1.41 g).

Melting point: 188.0°–190.0° C.

$^1$H-NMR (500 MHz, CDCl$_3$) δ: 3.29 (bs, 2H), 3.53 (bs, 2H), 3.76 (bs, 4H), 5.16 (s, 2H), 6.91–6.93 (m, 6H), 7.03 (d, 1H), 7.14–7.16 (m, 3H), 7.20 (d, 1H), 7.24–7.34 (m, 10H), 7.38 (d, 1H), 7.45–7.52 (m, 2H), 7.87 (d, 1H), 7.93 (d, 1H)

Example 38

Preparation of 3-[[2'-(1-triphenylmethyltetrazol-5-yl)biphenyl-4-yl]methyloxy]-4-aminobenzoic acid morpholide ([3]-(34)-587)

A solution of the compound ([3]-(33)-587) (0.60 g) prepared in Example 37, ethanol (150 ml), and ethyl acetate (40 ml) was stirred at 70° C. for 15 minutes. After 10% Pd/C (0.10 g) and hydrazine monohydrate (1 ml) were added to the solution, the mixture was stirred at 70° C. for 1 hour. The insolubles were filtered through celite, and the filtrate was concentrated to obtain colorless foam (0.67 g). The product was purified by silica gel column chromatography (Kieselgel 60=80 g, chloroform/ethyl acetate=13/7) to obtain the compound ([3]-(34)-587) (0.09 g).

Melting point: 95.0°–105.0° C.

$^1$H-NMR (500 MHz, CDCl$_3$) δ: 1.57 (bs, 1H), 3.63 (bs, 4H),3.67 (bs, 4H), 3.93 (bs, 1H), 4.98 (s, 2H), 6.66 (d, 1H), 6.89–6.92 (m, 7H), 7.03 (s, 1H), 7.14–7.33 (m, 13H), 7.39 (d, 1H), 7.46–7.53 (m, 2H), 7.96 (d, 1H)

Example 39

Preparation of 3-[[2'-(1-triphenylmethyltetrazol-5-yl)biphenyl-4-yl]methyloxy]-4-valeramidobenzoic acid morpholide ([3]-(35)-587')

The compound ([3]-(34)-587) (0.07 g) prepared in Example 38 and 4-dimethylaminopyridine (0.01 g) were dissolved in dry pyridine (1 ml). Valeryl chloride (0.043 g) was added dropwise by a syringe while cooling on ice. The mixture was stirred at room temperature for 2 hours, then, poured into water (20 ml), extracted with chloroform (10 ml) twice, and dried over anhydrous magnesium sulfate. The solvent was evaporated under reduced pressure to obtain the compound ([3]-(35)-587') (0.08 g) as a light yellow solid.

$^1$H-NMR (500 MHz, CDCl$_3$) δ: 0.89 (t, 3H), 1.34 (sext, 2H), 1.64 (quint, 2H), 2.27 (t, 2H), 3.67 (bs, 8H), 5.05 (s, 2H), 6.93–6.95 (m, 7H), 7.02 (d, 1H), 7.11 (s, 1H), 7.15–7.35 (m, 12H), 7.40 (d, 1H), 7.47–7.54 (m, 2H), 7.79 (s, 1H), 7.93 (d, 1H), 8.63 (bs, 1H)

Example 40

Preparation of 3-[[2'-(1H-tetrazol-5-yl)biphenyl-4-yl]methyloxy]-4-valeramidobenzoic acid morpholide ([3]-(35)-587) (Compound No. 587)

To a solution of the compound ([3]-(35)-587') (0.069 g) prepared in Example 39, methanol (2 ml), and THF (5 ml), concentrated hydrochloric acid (1 ml) was added dropwise. The mixture was stirred at room temperature for 1 hour.

poured into 1N NaOH aqueous solution (20 ml), and allowed to stand overnight. The solvent was evaporated at 50° C. under reduced pressure to a solution volume of approximately 20 ml, and the precipitated solid was filtered out. To the filtrate, 1N HCl aqueous solution was added until pH 2 and the precipitated solid was filtered out to obtain a colorless solid (0.035 g). The product was purified by silica gel column chromatography (Kieselgel 60=5 g, chloroform/methanol=5/1) to obtain the Compound No. 587 (0.030 g) as a colorless solid.

$^1$H-NMR (500 MHz, CDCl$_3$) δ: 0.96 (t, 3H), 1.43 (sext, 2H), 1.73 (quint, 2H), 2.44 (t, 2H), 3.40–3.80 (br, 8H), 5.28 (s, 2H), 6.77 (s, 1H), 6.95 (d, 1H), 7.11 (d, 2H), 7.21 (d, 2H), 7.46–7.59 (m, 4H), 7.91 (s, 1H), 7.97 (bs, 1H), 8.38 (d, 1H)

Example 41

Preparation of 4-amino-3-nitrobenzoic acid morpholide ([4]-(42)-592)

A mixture of 4-amino-3-nitrobenzoic acid (7.40 g), 1-hydroxybenzotriazole (6.59 g), dicyclohexylcarbodiimide (10.90 g), dry N,N-dimethylformamide (74 ml), and morpholine (4.3 ml) was stirred at room temperature for 2 hours. The insolubles were filtered out, and washed with N,N-dimethylformamide. The filtrate and the washing were combined, and concentrated to obtain a yellowish brown solid (16.01 g).

Melting point: 184.0°–189.0° C.

$^1$H-NMR (500 MHz, d$_6$-DMSO) δ: 3.50–3.58 (m, 4H), 3.59–3.60 (m, 4H), 7.04 (d, 1H), 7.47 (dd, 1H), 8.03 (d, 1H)

Example 42

Preparation of 4-acetamido-3-nitrobenzoic acid morpholide ([4]-(43)-592)

The compound ([4]-(42)-592) (18.37 g) prepared in Example 41 and dimethylaminopyridine (5.67 g) were dissolved in dry pyridine (370 ml). The solution was stirred while cooling on ice under a nitrogen gas atmosphere, and acetyl chloride (9.9 ml) was added dropwise over 5 minutes. Then, the mixture was stirred on an oil bath at 65° C. for 30 minutes, the resulting solution was cooled to room temperature, and concentrated. The residue was dissolved in chloroform, washed with water, and then saturated brine, and dried over anhydrous sodium sulfate. After filtration and concentration, reddish brown oil (19.52 g) was obtained. The product was purified by silica gel column chromatography (Kieselgel 60=1.0 kg, chloroform/methanol=120/1) to obtain the compound ([4]-(43)-592) (10.74 g) as a yellow solid.

Melting point: 128.0°–132.0° C.

$^1$H-NMR (500 MHz, CDCl$_3$) δ: 2.32 (s, 3H), 3.40–3.85 (br, 8H), 7.70 (dd, 1H), 8.33 (d, 1H), 8.86 (d, 1H), 10.39 (bs, 1H)

Example 43

Preparation of 4-acetamido-3-aminobenzoic acid morpholide ([4]-(44)-592)

The compound ([4]-(43)-592) (10.73 g) prepared in Example 42 was dissolved in ethanol (400 ml). After the solution was heated on a bath at 60° C. for 30 minutes, hydrazine monohydrate (4 ml) and a suspension of 10% Pd/C (0.55 g) in ethanol (2 ml) were added to the solution. The mixture was stirred at the same temperature for 30 minutes. The insolubles were filtered through celite, and the filtrate was concentrated to obtain a crude product (12.67 g). The product was purified by silica gel column chromatography (Kieselgel 60=600 g, chloroform/methanol=10/1) to obtain the compound ([4]-(44)-592) (4.63 g) as a light yellow solid.

Melting point: 198.0°–200.0° C.

$^1$H-NMR (500 MHz, CDCl$_3$) δ: 2.22 (s, 3H), 3.35–3.85 (br, 8H), 3.88 (bs, 2H), 6.64 (dd, 1H), 6.71 (d, 1H), 7.04 (d, 1H), 8.04 (bs, 1H)

Example 44

Preparation of 4-acetamide-3-[[2'-(1-triphenylmethyltetrazol-5-yl)biphenyl-4-yl]methylamino]benzoic acid morpholide ([4]-(45)-592)

A solution of the compound ([4]-(44)-592) (4.57 g) prepared in Example 43, N-(triphenylmethyl)-5-[4'-(bromomethyl)biphenyl-2-yl]tetrazole (10.65 g), diisopropylethylamine (30.3 ml), and chloroform (270 ml) was stirred in an oil bath at 70° C. for 4 hours under a nitrogen gas atmosphere. The reaction solution was cooled, and concentrated to obtain a yellow solid (19.45 g). The product was purified by silica gel column chromatography (Kieselgel 60=700 g, chloroform/methanol=30/1) to obtain the compound ([4]-(45)-592) (6.55 g) as light yellow foam.

$^1$H-NMR (500 MHz, CDCl$_3$) δ: 2.11 (s, 3H), 3.15–3.90 (br, 8H), 4.17 (d, 2H), 4.42 (t, 1H), 6.58 (s, 1H), 6.63 (d, 1H), 6.95 (d, 6H), 7.07–7.13 (m, 6H), 7.25–7, 37 (m, 8H), 7.43–7.51 (m, 3H), 7.88 (d, 1H), 7.93 (s, 1H)

Example 45

Preparation of 4-acetamido-3-N-[[[2'-(1-triphenylmethyltetrazol-5-yl)biphenyl-4-yl]methyl]valeramido]benzoic acid morpholide ([4]-(46)-592')

The compound ([4]-(45)-592) (5.80 g) prepared in Example 44 and 4-dimethylaminopyridine (0.96 g) were dissolved in dry pyridine (58 ml), and valeryl chloride (2.8 ml) was added dropwise to the solution. The mixture was stirred at room temperature for 1 hour, poured into ice water, extracted with chloroform, and washed with water. The solution was washed with saturated brine, dried over sodium sulfate, filtered, and concentrated to obtain yellowish brown oil (7.76 g). The product was purified by silica gel column chromatography (Kieselgel 60=600 g, chloroform/methanol=60/1) to obtain the compound ([4]-(46)-592') (5.57 g) as yellow foam.

$^1$H-NMR (500 MHz, CDCl$_3$) δ: 0.81 (t, 3H), 1.14–1.25 (m, 2H), 1.51–1.61 (m, 2H), 1.76 (s, 3H), 1.86 (dt, 1H), 1.98 (dt, 1H), 3.25–4.00 (br, 8H), 4.08 (d, 1H), 5.43 (d, 1H), 6.60 (s, 1H), 6.94 (d, 6H), 7.06–7.10 (m, 4H), 7.21 (d, 1H), 7.25–7.35 (m, 10H), 7.45–7.53 (m, 2H), 7.92 (dd, 1H), 8.12 (d, 1H)

Example 46

Preparation of 4-acetamido-3-N-[[[2'-(1H-tetrazol-5-yl)biphenyl-4-yl]methyl]valeramido]benzoic acid morpholide (Compound No. 592)

The compound ([4]-(46)-592') (5.57 g) prepared in Example 45 was dissolved in tetrahydrofuran (60 ml), and concentrated hydrochloric acid (60 ml) was added to the solution while cooling on ice. The solution was allowed to stand at room temperature for 6 hours. The reaction solution was adjusted. to approximately pH 7 with 10N NaOH aqueous solution and concentrated. The residue was dissolved in chloroform. washed with water and then saturated brine. dried over sodium sulfate. filtered, and concentrated to obtain light yellow oil (3.95 g). The product was purified by silica gel column chromatography (Kieselgel 60=270 g. chloroform/methanol=15/1) to obtain a light yellow solid (3.48 g). The product was further added to acetone (30 ml). sonicated. and filtered. The filtrate was concentrated to obtain a solid (1.47 g). To the solid, 1N NaOH aqueous solution (3.55 ml) was added; and the solution was adjusted to pH 10. After water (60 ml) was added. the whole was sonicated, and filtered through celite. The filtrate was adjusted to pH 4 with 1N HCl aqueous solution, and the precipitated solid was filtered out to obtain the above-captioned Compound No. 592 (0.86 g) as a colorless solid.

Melting point: 127.0°–131.0° C.

$^1$H-NMR (500 MHz, CDCl$_3$) δ: 0.84 (t, 3H), 1.17–1.30, 1.54–1.64 (each m, each 2H), 1.95, 2.09 (each dt, each 1H), 2.24 (s, 3H), 3.45–3.95 (br, 8H), 4.07, 5.56 (each d, each 1H), 6.58 (bs, 1H), 6.85 (bd, 1H), 6.99, 7.03 (each d, each 2H), 7.36 (dd, 1H), 7.40–7.60 (m, 2H), 7.46 (d, 1H), 7.87 (bd, 1H), 8.40 (bd, 1H), 13.6–14.0 (br, 1H)

Example 47

Preparation of ethyl 4-dimethylamino-3-nitrobenzoate ([5]-(52)-591)

Ethyl 4-dimethylaminobenzoate (9.10 g) was dissolved in sulfuric acid (14 ml), and mixed acid (concentrated sulfuric acid/concentrated nitric acid=1/1) (9.0 ml) was added dropwise at room temperature. The reaction solution was stirred for 4 hours while maintaining at 5° C.–10° C. The reaction solution was poured into ice water (100 g). The precipitated crystals were filtered, and washed with water. The resulting crystals were recrystallized from water/methanol to obtain the above-captioned compound ([5]-(52)-591) (10.56 g) as yellow needle crystals.

Melting point: 78.5°–79.0° C.

$^1$H-NMR (500 MHz, CDCl$_3$) δ: 1.38 (t, 3H), 2.99 (s, 6H), 4.35 (q, 2H), 6.97 (d, 1H), 8.01 (dd, 1H), 8.44 (d, 1H)

Example 48

Preparation of 4-dimethylamino-3-nitrobenzoic acid ([5]-(53)-591)

A solution of the compound ([5]-(52)-591) (10.0 g) prepared in Example 47, tetrahydrofuran (250 ml), methanol (100 ml), and 1N NaOH aqueous solution (100 ml) was stirred at room temperature for 18 hours. Tetrahydrofuran was evaporated under reduced pressure, and the residue was adjusted to pH 4-5 with 1N HCl aqueous solution. The precipitated crystals were collected by filtration and dried to obtain the above-captioned compound ([5]-(53)-591) (8.76 g) as a yellow solid.

Melting point: 212.0°–215.5° C.

$^1$H-NMR (500 MHz, d$_6$-DMSO) δ: 2.93 (s, 6H), 7.20 (d, 1H), 7.93 (dd, 1H), 8.24 (d, 1H), 12.84 (s, 1H)

Example 49

Preparation of 4-dimethylamino-3-nitrobenzoic acid morpholide ([5]-(54)-591)

The compound ([5]-(53)-591) (8.00 g) prepared in Example 48 was dissolved in dry tetrahydrofuran (200 ml), and 1-hydroxybenzotriazole (5.40 g) and dicyclohexylcarbodiimide (8.30 g) were added to the solution. The mixture was stirred at room temperature for 30 minutes. Then morpholine (3.65 g) was added to the solution. The mixture was stirred for 16 hours. The precipitated insolubles were filtered out, and the filtrate was concentrated under reduced pressure. The residue was purified by silica gel column chromatography (Kieselgel 60=180 g, chloroform) to obtain the above-captioned compound ([5]-(54)-591) (10.43 g) as a yellow solid.

Melting point: 89.5°–91.0° C.

$^1$H-NMR (500 MHz, d$_6$-DMSO) δ: 2.95 (s, 6H), 3.5–3.8 (br, 8H), 7.01 (d, 1H), 7.50 (dd, 1H), 7.89 (d, 1H)

Example 50

Preparation of 3-amino-4-dimethylaminobenzoic acid morpholide ([5]-(55)-591)

With vigorously stirring, a solution of the compound ([5]-(54)-591) (0.50 g) prepared in Example 49 in ethanol (50 ml) was heated on an oil bath at 50° C. To the solution, 10% Pd/C (0.050 g) wetted with ethanol and then hydrazine monohydrate (0.5 ml) were added successively. After stirring for 20 minutes, the catalyst was removed by filtration through celite, and the solution was concentrated. The residue was purified by silica gel column chromatography (Kieselgel 60=15 g, hexane/ethyl acetate=1/1) to obtain the above-captioned compound ([5]-(55)-591) (0.40 g) as a light red solid.

$^1$H-NMR (500 MHz, CDCl$_3$) δ: 2.68 (s, 6H), 3.4–3.8 (br, 8H), 6.73–6.76 (m, 2H), 6.97 (d, 1H)

Example 51

Preparation of 4-dimethylamino-3-valeramidobenzoic acid morpholide ([5]-(56)-591)

The compound ([5]-(55)-591) (0.58 g) prepared in Example 50 was dissolved in anhydrous pyridine, and valeryl chloride (0.27 ml) was added to the solution. The mixture was stirred at room temperature for 30 minutes. After water was added, the whole was extracted with ethyl acetate. The extract was dried over anhydrous sodium sulfate, and the solvent was evaporated under reduced pressure. The residue was purified by silica gel column chromatography (Kieselgel 60=20 g, chloroform/methanol=20/1) to obtain the above-captioned compound ([5]-(56)-591) (0.69 g) as a light yellow solid.

Melting point: 92.5°–96.0° C.

$^1$H-NMR (500 MHz, CDCl$_3$) δ: 0.97 (t, 3H), 1.38 (sext, 2H), 1.73 (quint, 2H), 2.42 (t, 2H), 2.64 (s, 6H), 3.4–3.9 (br, 8H), 7.2–7.3 (m, 2H), 8.31 (s, 1H), 8.42 (s, 1H)

Example 52

Preparation of 4-dimethylamino-3-N-[2'-[(1-triphenylmethyltetrazol-5-yl)biphenyl-4-yl]methyl] valeramidobenzoic acid morpholide ([5]-(57)-591')

The compound ([5]-(56)-591) (0.05 g) prepared in Example 51 was dissolved in dimethyl sulfoxide (10 ml), and powdered potassium hydroxide (0.13 g) was added to the solution. The mixture was stirred at room temperature for several minutes. After the powder of potassium hydroxide was dissolved, N-(triphenylmethyl)-5-[4'-(bromomethyl)biphenyl-2-yl]tetrazole (1.00 g) was added to the solution. The mixture was stirred at room temperature for 1.5 hours. A small amount of water was added to the solution, and the whole was extracted with ethyl acetate. The solution was washed with water, and dried over anhydrous sodium sulfate. The solvent was evaporated, and the residue was purified by silica gel column chromatography (Kieselgel 60=10 g, hexane/ethyl acetate=2/1) to obtain the above-captioned compound ([5]-(57)-591') (1.03 g) as colorless foam.

Melting point: 93.0°–94.0° C.

$^1$H-NMR (500 MHz, CDCl$_3$) δ: 0.85 (t, 3H), 1.21 (sext, 2H), 1.63 (quint, 2H) 2.10 (dt, 1H), 2.26 (dt, 1H), 2.93 (s, 6H), 3.1–3.9 (br, 8H), 4.01 (d, 1H), 5.60 (d, 1H), 6.59 (d, 1H), 6.8–7.0 (m, 13H), 7.2–7.4 (m, 9H), 7.4–7.5 (m, 2H), 7.86 (d, 1H)

Example 53

Preparation of 4-dimethylamino-3-N-[2'-[(1H-tetrazol-5-yl)biphenyl-4-yl]methyl] valeramidobenzoic acid morpholide ([5]-(57)-591) (Compound No. 591)

The compound ([5]-(57)-591') (0.15 g) prepared in Example 52 was dissolved in tetrahydrofuran (3 ml), and 12% HCl aqueous solution (0.45 ml) was added to the solution. The mixture was stirred for 24 hours. After the mixture was adjusted to pH 11 by adding 1N NaOH aqueous solution, tetrahydrofuran in the solvent was evaporated, and solids were removed by filtration. To the mother liquid, 1N HCl aqueous solution was added dropwise, and the solvent was adjusted to pH 4-5, and the precipitated solid was collected by filtration. The residue was purified by silica gel column chromatography (Kieselgel 60=5 g, chloroform/ethyl acetate=10/1) to obtain the above-captioned compound ([5]-(57)-591) (0.080 g) as white foam.

Melting point: 102.0°–105.0° C.

$^1$H-NMR (500 MHz, d$_6$-DMSO) δ: 0.82 (t, 3H), 1.2–1.3 (m, 2H), 1.5–1.6 (m, 2H), 2.10 (dt, 1H), 2.35 (dt, 1H), 2.87 (s, 6H), 3.2–3.7 (br, 8H), 4.22 (d, 1H), 5.48 (d, 1H), 6.89 (d, 1H), 7.02 (d, 2H), 7.1–7.2 (m, 5H), 7.31 (dd, 1H), 7.53 (d, 1H), 7.7–7.8 (m, 2H)

Example 54

Preparation of 4-dimethylamino-3-N-[[(4-methoxycarbonylphenyl)methyl]valeramido]benzoic acid morpholide ([5]-(57)-184')

After 60% NaH (0.72 g) was washed with n-hexane, dry DMSO (46 ml) was poured thereto, and the mixture was stirred at room temperature for 15 minutes. To the resulting suspension, a solution of the compound ([5]-(56)-591) (4.63 g) prepared in Example 51 in dry DMSO (46 ml) was added dropwise at room temperature over 10 minutes with stirring. The reaction system which had been cloudy became yellowish orange suspension and foamed. Then methyl 4-bromomethylbenzoate (3.83 g) was added over 2 minutes, and the reaction system was stirred at room temperature for 3 hours, whereby the reaction system became clear yellowish orange solution. The reaction solution was poured into 1N HCl aqueous solution, extracted with ethyl acetate, washed with water and saturated brine, dried over anhydrous sodium sulfate, and concentrated to obtain a light yellow solid (6.76 g). The solid was purified by silica gel column chromatography (Kieselgel 60=670 g, chloroform/acetone= 15/1) to obtain the above-captioned compound ([5]-(57)-184') (6.71 g) as a light yellow solid.

$^1$H-NMR (500 MHz, CDCl$_3$) δ: 0.85 (t, 3H), 1.2–1.3 (m, 2H), 1.5–1.6 (m, 2H), 2.10 (dt, 1H), 2.35 (dt, 1H), 2.87 (s, 6H), 3.2–3.7 (br, 8H), 4.22 (d, 1H), 5.48 (d, 1H), 6.89 (d, 1H), 7.02 (d, 2H), 7.1–7.2 (m, 5H), 7.31 (dd, 1H), 7.53 (d, 1H), 7.7–7.8 (m, 2H)

Example 55

Preparation of 3-N-[[(4-carboxyphenyl)methyl] valeramido]-4-dimethylaminobenzoic acid morpholide ([5]-(57)-184) (Compound No. 184)

The compound ([5]-(57)-184') (6.71 g) prepared in Example 53 was dissolved in a solution of methanol (67 ml) and tetrahydrofuran (67 ml). Then 1N NaOH aqueous solution (67 ml) was added thereto, and the mixture was allowed to stand for 14 hours. The reaction solution was neutralized, concentrated, adjusted to approximately pH 1, extracted with chloroform, washed with water, dried over anhydrous sodium sulfate, and concentrated to obtain white foam (5.63 g). The white foam was purified by silica gel column chromatography (Kieselgel 60=280 g, chloroform/methanol=15/1) to obtain white foam (5.63 g). Further, n-hexane was added to the resulting foam, and the product was crystallized, and dried under vacuum to obtain the above-captioned compound ([5]-(57)-184) (4.45 g) as white crystals.

$^1$H-NMR (500 MHz, CDCl$_3$) δ: 0.85 (t, 3H), 1.2–1.3 (m, 2H), 1.5–1.6 (m, 2H), 2.10 (dt, 1H), 2.35 (dt, 1H), 2.87 (s, 6H), 3.2–3.7 (br, 8H), 4.22 (d, 1H), 5.48 (d, 1H), 6.89 (d, 1H), 7.02 (d, 2H), 7.1–7.2 (m, 5H), 7.31 (dd, 1H), 7.53 (d, 1H), 7.7–7.8 (m, 2H)

Example 56

Preparation of methyl 3-valeramidobenzoate ([6]-(62)-90)

To anhydrous pyridine (120 ml), methyl 3-aminobenzoate (5.00 g) was dissolved, and valeryl chloride (4.13 ml) was added while cooling on ice. The mixture was stirred at room temperature for 4 hours. Distilled water was added to the solution. The whole was extracted with ethyl acetate, washed with 5% sodium hydrogencarbonate aqueous solution and water, and dried over anhydrous sodium sulfate. The solvent was evaporated, and the residue was purified by silica gel column chromatography (Kieselgel 60=170 g, hexane/ethyl acetate=3/1) to obtain the above-captioned compound ([6]-(62)-90) (7.70 g) as a white solid.

Melting point: 97.0°–98.0° C.

$^1$H-NMR (500 MHz, CDCl$_3$) δ: 0.95 (t, 3H), 1.40 (sext, 2H), 1.72 (quint, 2H), 2.38 (t, 2H), 3.91 (s, 3H), 7.30–7.40 (br, 1H), 7.39 (t, 1H), 7.77 (d, 1H), 7.91 (d, 1H), 8.03 (s, 1H)

Example 57

Preparation of 3-valeramidobenzoic acid ([6]-(63)-90)

The compound ([6]-(62)-90) (7.56 g) prepared in Example 56 was dissolved in tetrahydrofuran (180 ml) and methanol (80 ml). To the solution, 1N NaOH aqueous solution (80 ml) was added. The mixture was stirred at room temperature for 5 hours. The solution was concentrated, and the organic solvents were evaporated. The residue was adjusted to pH 2 by adding 1N HCl aqueous solution. The precipitated crystals were collected by filtration, washed with distilled water, and dried to obtain the above-captioned compound ([6]-(63)-90) (6.43 g) as white crystals.

Melting point: 210.5°–212.0° C.

¹H-NMR (500 MHz, d₆-DMSO) δ: 0.88 (t, 3H), 1.33 (sext, 2H), 1.58 (quint, 2H), 2.32 (t, 2H), 7.41 (t, 1H), 7.60 (d, 1H), 7.82 (d, 1H), 8.23 (s, 1H), 10.04 (s, 1H), 12.91 (s, 1H)

Example 58

Preparation of 3-valeramidobenzoic acid morpholide ([6]-(64)-90)

The compound ([6]-(63)-90) (6.30 g) prepared in Example 57 was dissolved in tetrahydrofuran (126 ml). To the solution, dicyclohexylcarbodiimide (71.7 g) and 1-hydroxybenzotriazole (4.04 g) were added. The mixture was stirred at room temperature for 5 minutes. After morpholine (3.28 g) was added, the mixture was stirred at room temperature for 21 hours. The insolubles were filtered out, and the filtrate was concentrated. The residue was purified by silica gel column chromatography (Kieselgel 60=230 g, chloroform/methanol=20/1) to obtain the above-captioned compound ([6]-(64)-90) (8.09 g) as colorless oil.

¹H-NMR (500 MHz, CDCl₃) δ: 0.95 (t, 3H), 1.38 (sext, 2H), 1.68 (quint, 2H), 2.33 (t, 2H), 3.3–3.9 (br, 8H), 7.07 (d, 1H), 7.31 (t, 1H), 7.57 (s, 1H), 7.58 (d, 1H), 8.01 (s, 1H)

Example 59

Preparation of 3-[N-(4-methoxycarbonylphenyl)methyl]valeramidobenzoic acid morpholide ([6]-(65)-90') Compound No. 612)

To dry dimethyl sulfoxide (80 ml), 60% NaH (2.05 g) was added to the solution. The mixture was stirred at room temperature for 15 minutes. A solution of the compound ([6]-(64)-90) (7.96 g) prepared in Example 58 in dry dimethyl sulfoxide (80 ml) was added dropwise, and then methyl 4-bromomethylbenzoate (7.56 g) was added. The mixture was stirred at room temperature for 1 hour. The solution was poured into 1N HCl aqueous solution (200 g) cooled with ice, extracted with ethyl acetate, washed with water and saturated brine, dried over anhydrous sodium sulfate, and concentrated. The residue was purified by silica gel column chromatography (Kieselgel 60=300 g, hexane/ethyl acetate=1/3) to obtain the above-captioned compound ([6]-(65)-90') (Compound No. 612) (7.27 g) as white foam.

¹H-NMR (500 MHz, CDCl₃) δ: 0.82 (t, 3H), 1.22 (sext, 2H), 1.59 (quint, 2H), 2.06 (t, 2H), 3.0–3.8 (br, 8H), 3.94 (s, 3H), 4.95 (s, 2H), 6.94 (s, 1H), 7.10 (d, 1H), 7.25 (d, 2H), 7.37 (d, 1H), 7.42 (t, 1H), 8.00 (d, 1H)

EXAMPLE 60

Preparation of 3-[N-(4-carboxyphenyl)methyl]valeramidobenzoic acid morpholide ([6]-(65)-90) (Compound No. 90)

The compound ([6]-(65)-90') (5.95 g) prepared in Example 59 was dissolved in methanol (60 ml) and tetrahydrofuran (60 ml). 1N NaOH aqueous solution (60 ml) was added thereto, and the mixture was stirred at room temperature overnight. The organic solvents were evaporated under reduced pressure. The residue was adjusted to pH 2 by adding 1N HCl aqueous solution, and extracted with ethyl acetate, and dried over anhydrous sodium sulfate. The solvent was evaporated, and the residue was purified by silica gel column chromatography (Kieselgel 60=160 g, chloroform/methanol=10/1) to obtain the above-captioned compound ([6]-(65)-90) (Compound No. 90) (3.77 g) as a white solid.

Melting point: 169.5°–173.0° C.

¹H-NMR (500 MHz, CDCl₃) δ: 0.82 (t, 3H), 1.22 (sext, 2H), 1.59 (quint, 2H), 2.09 (t, 2H), 3.0–3.8 (br, 8H), 4.97 (s, 2H), 6.98 (s, 1H), 7.11 (d, 1H), 7.27 (d, 2H), 7.40 (d, 1H), 7.45 (t, 1H), 8.06 (d, 1H)

Example 61

Preparation of 4-hexyl-3-nitrobenzoic acid ([5]-(53)-75)

In concentrated sulfuric acid (20 ml), 4-hexylbenzoic acid (7.50 g) was dissolved while cooling on ice. Mixed acid of concentrated sulfuric acid/concentrated nitric acid (1/1) (7.0 ml) was added thereto dropwise over 5 minutes. The mixture was stirred for 20 minutes while cooling on ice and further for 30 minutes at room temperature. After the reaction was completed, the solution was poured into ice water. The precipitated crystals were collected by filtration, and dissolved in ethyl acetate. The solution was washed with water, and the organic layer was dried over anhydrous sodium sulfate. The solvent was evaporated under reduced pressure, and the residue was recrystallized from cyclohexane to obtain the above-captioned compound ([5]-(53)-75) (7.60 g) as colorless needle crystals.

Melting point: 106.5°–107.5° C.

¹H-NMR (500 MHz, CDCl₃) δ: 0.96 (t, 3H), 1.2–1.5 (m, 4H), 1.39 (bquint, 2H), 1.65 (bquint, 2H), 2.82 (t, 2H), 7.48 (d, 1H), 8.21 (dd, 1H), 8.58 (d, 1H)

Example 62

Preparation of 4-hexyl-3-nitrobenzoic acid morpholide ([5]-(54)-75)

The compound ([5]-(53)-75) (7.60 g) prepared in Example 61 was dissolved in anhydrous chloroform (152 ml). Then, 1-ethyl-3-(3-dimethylaminopropyl)carbodiimide hydrochloride (6.37 g), 1-hydroxybenzotriazole (4.48 g), and morpholine (6.31 g) were added to the solution. The reaction mixture was stirred at room temperature for 7 hours. After the reaction was completed, chloroform was added. The solution was washed with 0.5N HCl aqueous solution, 0.5N NaOH aqueous solution, and distilled water. After the organic layer was dried over anhydrous sodium sulfate, the solvent was evaporated under reduced pressure, and the residue was purified by silica gel column chromatography (Kieselgel 60=150 g, hexane/ethyl acetate=1/1) to obtain the above-captioned compound ([5]-(54)-75) (8.50 g) as a white solid.

Melting point: 68.5°–71.5° C.

¹H-NMR (500 MHz, CDCl₃) δ: 0.93 (t, 3H, 1.2–1.4 (m, 4H), 1.39 (bquint, 2H), 1.62 (bquint, 2H), 2.90 (t, 2H), 3.3–4.1 (br, 8H), 7.41 (d, 1H) 7.57 (dd, 1H), 7.92 (d, 1H)

Example 63

Preparation of 3-amino-4-hexylbenzoic acid morpholide ([5]-(55)-75)

The compound ([5]-(54)-75) (700 mg) prepared in Example 62 was dissolved in ethanol (35 ml). After the solution was heated to 50° C., a suspension of 10% Pd/C (70 mg) in ethanol was added, and hydrazine monohydrate (0.35 ml) was added to the solution. The solution was stirred at 50° C. for 30 minutes. After the reaction was completed, the solution was filtered through celite 545 to remove the catalyst. The solvent was evaporated under reduced pressure. The residue was purified by silica gel column chromatography (Kieselgel 60=20 g, ethyl acetate) to obtain the above-captioned compound ([5]-(55)-75) (631 mg) as colorless oil.

$^1$H-NMR (500 MHz, CDCl$_3$) δ: 0.82 (t, 3H), 1.1–1.3 (m, 4H), 1.29 (bquint, 2H) 1.53 (bquint, 2H), 2.41 (t, 2H), 3.3–3.9 (br, 10H), 6.64 (d, 1H), 6.96 (d, 1H), 7.20 (s, 1H)

Example 64

Preparation of 4-hexyl-3-[(4-methoxycarbonylphenyl)methyl]aminobenzoic acid morpholide ([5]-(57)-75')

The compound ([5]-(55)-75) (600 mg) prepared in Example 63 was dissolved in acetic acid (6.0 ml). Then, 4-methoxycarbonylbenzaldehyde (373 mg) was added. The mixture was stirred at room temperature for 4 hours. Then, boranediethylamine complex (146 mg) was added to the solution. The mixture was stirred at room temperature for 30 minutes. After the reaction was completed, water was added to the solution. The solution was extracted with ethyl acetate, washed with distilled water, and dried over anhydrous sodium sulfate. The solvent was evaporated under reduced pressure, and the residue was purified by silica gel column chromatography (Kieselgel 60=30 g, hexane/ethyl acetate=1/1) to obtain the above-captioned compound ([5]-(57)-75') (841 mg) as a white solid.

Melting point: 89.0°–90.5° C.

$^1$H-NMR (500 MHz, CDCl$_3$) δ: 0.82 (t, 3H), 1.2–1.3 (m, 4H), 1.31 (bquint, 2H), 1.57 (bquint, 2H), 2.45 (t, 2H), 3.0–3.8 (br, 8H), 3.84 (s, 3H), 4.14 (bs, 1H), 4.40 (s, 2H), 6.41 (d, 1H), 6.65 (dd, 1H), 7.01 (d, 1H), 7.34 (d, 1H), 7.93 (d, 1H)

Example 65

Preparation of 3-[(4-carboxyphenyl)methyl]amino-4-hexylbenzoic acid morpholide ([5]-(57)-75) (Compound No. 75)

The compound ([5]-(57)-75') (46 mg) prepared in Example 64 was dissolved in tetrahydrofuran (1.0 ml) and methanol (0.5 ml). Then, 1N NaOH aqueous solution (0.25 ml) was added to the solution. The mixture was stirred at room temperature for 24 hours. After the reaction was completed, the solution was adjusted to approximately pH 5 with 1N HCl aqueous solution, and extracted with ethyl acetate. The solution was dried over anhydrous sodium sulfate, and the solvent was evaporated under reduced pressure. The residue was purified by preparative thin layer chromatography (Merck 13792, chloroform/methanol=10/1) to obtain the above-captioned compound ([5]-(57)-75) (Compound No. 75) (39.8 mg) as a light yellow solid.

Melting point: 205.0°–209.5° C.

$^1$H-NMR (500 MHz, CDCl$_3$) δ: 0.82 (t, 3H), 1.2–1.3 (m, 4H), 1.32 (bquint, 2H), 1.58 (quint, 2H), 2.45 (t, 2H), 3.0–4.9 (br, 8H), 4.26 (s, 2H), 6.43 (d, 1H), 6.65 (dd, 2H), 7.01 (d, 1H), 7.36 (d, 2H), 7.98 (d, 2H)

Example 66

Preparation of 4-isopropyl-3-nitrobenzoic acid ([5]-(53)-372)

Cuminic acid (5.0201 g) was suspended in concentrated sulfuric acid (7.5 ml), and a solution of concentrated sulfuric acid/70% nitric acid (1/1, v/v) (5.0 ml) was added thereto dropwise under stirring while cooling on ice. After nearly white suspension was stirred at room temperature for 1 hour, the suspension was poured into ice water. The resulting light yellow crystals were collected by filtration, washed with water, and dried by vacuum heating (60° C.) to obtain the above-captioned compound [5]-(53)-372) (6.0717 g).

Melting point: 152.0°–155.5° C.

$^1$H-NMR (500 MHz, d$_6$-DMSO) δ: 1.28 (d, 6H), 3.28 (sept, 1H), 7.79 (d, 1H), 8.16 (dd, 1H), 8.24 (d, 1H), 13.47 (b, 1H)

Example 67

Preparation of 4-isopropyl-3-nitrobenzoic acid morpholide ([5]-(54)-372)

The compound ([5]-(53)-372) (5.9731 g) prepared in Example 66 was dissolved in anhydrous dimethylformamide (DMF) (90 ml). Then, 1-hydroxybenzotriazole (5.0157 g), 1-ethyl-3-(3-dimethylaminopropyl)carbodiimide hydrochloride (7.1155 g), triethylamine (5.2 ml), and morpholine (3.2 ml) were added to the solution. The mixture was stirred at room temperature for 16 hours. A small amount of water was added to the resulting yellowish orange solution including the white salt to obtain a homogeneous solution. The solution was concentrated, and the residue was dissolved in chloroform. To precipitate the solid, 1N HCl aqueous solution was added. After the precipitated solid was collected by filtration and washed with chloroform, the filtrate and the washing were washed with 1N HCl aqueous solution and saturated brine. The washed product was dried over anhydrous sodium sulfate, and concentrated to obtain yellowish brown oil (8.7070 g). The oil was purified by silica gel column chromatography (Kieselgel 60=260 g, hexane/ethyl acetate=2/1) to obtain the above-captioned compound ([5]-(54)-372) (7.7001 g) as light yellow oil.

$^1$H-NMR (500 MHz, CDCl$_3$) δ: 1.97 (d, 6H), 3.43 (sept, 1H), 3.72 (b, 8H), 7.55 (d, 1H), 7.60 (dd, 1H), 7.76 (d, 1H)

Example 68

Preparation of 3-amino-4-isopropylbenzoic acid morpholide ([5]-(55)-372)

The compound ([5]-(54)-372) (0.4050 g) prepared in Example 67 was dissolved in ethanol (20 ml). Then, a suspension of 10% Pd/C (0.0405 g) in ethanol (4 ml), and hydrazine monohydrate (0.4 ml) were added to the solution. The mixture was stirred in an oil bath at 60° C. for 20 minutes. After the reaction was completed, the solution was filtered through a glass filter carrying celite 545 thereon to remove the catalyst. The filtrate was concentrated to obtain colorless oil (0.3912 g). The crude oil was purified by silica gel column chromatography (Kieselgel 60=20 g, ethyl acetate) to obtain the above-captioned compound ([5]-(55)-372) (0.3580 g) as white crystals.

Melting point: 112.0°–115.0° C. $^1$H-NMR (500 MHz, CDCl$_3$) d: 1.25 (d, 6H), 2.89 (sept, 1H), 3.4–3.9 (b, 10H), 6.72 (d, 1H), 6.76 (dd, 1H), 7.14 (d, 1H)

Example 69

Preparation of 4-isopropyl-3-valeramidobenzoic acid morpholide ([5]-(56)-372)

The compound ([5]-(55)-372) (0.4148 g) prepared in Example 68 was dissolved in anhydrous pyridine (5.0 ml). Then, valeryl chloride (0.2 ml) was added thereto dropwise while cooling on ice with stirring. After the reaction solution was stirred on ice for 3 hours, the reaction solution was poured into ice water. The solution was extracted with ethyl acetate, washed with water and saturated brine, dried over anhydrous sodium sulfate, and concentrated. The resulting light yellow oil (0.6027 g) was purified by silica gel column chromatography (LiChroprep Si 60=30 g, chloroform/ acetone=7/1) to obtain the above-captioned compound ([5] -(56)-372) (0.4903 g) as light yellow oil.

$^1$H-NMR (500 MHz, CDCl$_3$) d: 0.97 (t, 3H), 1.23 (d, 6H), 1.43 (sext, 2H), 1.73 (quint, 2H), 2.40 (t, 2H), 3.01 (sept, 1H), 3.45–3.9 (b, 8H), 7.23 (d, 1H), 7.30 (d, 1H), 7.33 (bs, 1H), 7.65 (s, 1H)

Example 70

Preparation of 4-isopropyl-3-N-[[(4-methoxycarbonylphenyl)methyl]valeramido]benzoic acid morpholide ([5]-(57)-372')

After oil of 60% NaH (0.0729 g) was removed by washing with hexane, anhydrous dimethyl sulfoxide (DMSO) (4.6 ml) was added to the washed NaH. The mixture was stirred at room temperature for 30 minutes. A solution of the compound ([5]-(56)-372) (0.4659 g) prepared in Example 69 in anhydrous DMSO (4.6 ml) was added dropwise at room temperature to obtain a reddish brown suspension. To the suspension, a solution of methyl 4-(bromomethyl)benzoate (0.3853 g) in anhydrous DMSO (2.3 ml) was added dropwise. After the resulting reddish brown solution was stirred at room temperature for 3.5 hours, the reaction solution was poured into cold 1N HCl aqueous solution. The solution was extracted with chloroform. The chloroform layer was washed with water and saturated brine, dried over anhydrous sodium sulfate, and concentrated to obtain reddish brown oil (0.8369 g). The crude oil was purified by silica gel column chromatography (LiChroprep Si 60=42 g, Chloroform/acetone=20/1) to obtain the above-captioned compound ([5]-(57)-372') (0.4073 g) as light yellow crystals.

Melting point: 105.0°–108.0° C.

$^1$H-NMR (500 MHz, CDCl$_3$) δ: 0.83 (t, 2H), 1.18 (d, 3H), 1.17–1.25(m, 2H), 1.21 (d, 3H), 1.53–1.65 (m, 2H), 1.89 (dt, 1H), 2.01 (dt, 1H), 3.03 (sept, 1H), 3.25–3.9 (b, 8H), 3.91 (s, 3H), 4.00 (d, 1H), 5.71 (d, 1H), 6.59 (d, 1H), 7.27 (d, 2H), 7.43 (dd, 1H), 7.46 (d, 1H), 7.93 (d, 2H)

Example 71

Preparation of 3-N-[[(4-carboxyphenyl)methyl] valeramido]-4-isopropylbenzoic acid morpholide ([5]-(57)-372) (Compound No. 372)

The compound ([5]-(57)-372') (0.3812 g) prepared in Example 70 was dissolved in a solvent of methanol (3.8 ml) and tetrahydrofuran (3.8 ml). Then, 1N NaOH aqueous solution (3.8 ml) was added to the solution, and the reaction solution was allowed to stand at room temperature for 13 hours. After the reaction solution was neutralized with 1N HCl aqueous solution, the solution was concentrated. The residue was acidified with 1N HCl aqueous solution, and extracted with chloroform. The chloroform layer was washed with water and saturated brine, dried over anhydrous sodium sulfate, and concentrated to obtain yellow oil (0.3645 g). The crude oil was purified by silica gel column chromatography (Kieselgel 60=20 g, chloroform/methanol= 15/1) to obtain the above-captioned compound ([5]-(57)- 372) (Compound No. 372) (0.2548 g) as white crystals.

Melting point: 224.0°–227.0° C.

$^1$H-NMR (500 MHz, CDCl$_3$) δ: 0.83 (t, 3H), 1.19 (d, 3H), 1.18–1.30 (m, 2H), 1.21 (d, 3H), 1.59 (tt, 2H), 1.92 (dt, 1H), 1.97 (dt, 1H), 3.05 (sept, 1H), 2.85–3.9 (b, 8H), 4.02 (d, 1H), 5.73 (d, 1H), 6.62 (s, 1H), 7.30 (d, 2H), 7.44 (d, 1H), 7.45 (s, 1H), 7.47 (d, 1H), 7.98 (d, 2H)

Example 72

Preparation of 4-methyl-3-nitrobenzoic acid ([5]-(53)-278)

In concentrated sulfuric acid (15.1 ml), p-toluic acid (10.094 g) was suspended. While the temperature of the solution was maintained at less than 30° C., a solution of a mixture of concentrated sulfuric acid/70% nitric acid (1/1, v/v) (10.1 ml) was added dropwise under stirring while cooling on ice. After the light yellow suspension was stirred at room temperature for 1.5 hours, the suspension was poured into ice water. The resulting light yellow crystals were collected by filtration, washed with water, and dried by vacuum heating (60° C.) to obtain the above-captioned compound ([5]-(53)-278) (12.755 g).

Melting point: 188.0°–190.5° C.

$^1$H-NMR (500 MHz, d$_6$-DMSO) δ: 2.59 (s, 3H), 7.65 (d, 1H), 8.13 (dd, 1H), 8.42 (d, 1H), 13.49 (b, 1H)

Example 73

Preparation of 4-methyl-3-nitrobenzoic acid morpholide ([5]-(54)-278)

The compound ([5]-(53)-278) (6.5272 g) prepared in Example 72 was dissolved in anhydrous DMF (98 ml). Then, 1-hydroxybenzotriazole (6.3297 g), 1-ethyl-3-(3-dimethylaminopropyl)carbodiimide hydrochloride (8.9795 g), triethylamine (6.5 ml), and morpholine (4.1 ml) were added to the solution. The mixture was stirred at room temperature for 4 hours. A small amount of water was added to the resulting yellowish orange solution including the white salt to obtain a homogeneous solution. The solution was concentrated. The residue was dissolved in chloroform, and the solution was washed with 1N HCl aqueous solution and saturated brine. The organic layer was dried over anhydrous sodium sulfate, and concentrated to obtain yellowish brown crystals (8.9903 g). The product was recrystallized from n-hexane/ethyl acetate to obtain the above-captioned compound ([5]-(54)-278) (7.8455 g) as light yellow crystals.

Melting point: 108.0°–110.0° C.

$^1$H-NMR (500 MHz, d$_6$-DMSO) δ: 2.64 (s, 3H), 3.35–4.0 (b, 8H), 7.42 (d, 1H), 7.57 (dd, 1H), 8.03 (d, 1H)

Example 74

Preparation of 3-amino-4-methylbenzoic acid morpholide ([5]-(55)-278)

The nitro compound ([5]-(54)-278) (1.208 g) prepared in Example 73 was dissolved in ethanol (50 ml), and the solution was heated in an oil bath at 60° C. A suspension of 10% Pd/C (150 mg) in ethanol (3 ml) was added to the solution, and hydrazine monohydrate (1 ml) was further added. After the mixture was heated for 15 minutes, the catalyst was filtered out through celite 545. The filtrate was concentrated. The residue was washed with chloroform (100 ml)/water (20 ml), and concentrated to obtain the above-captioned compound ([5]-(55)-278) (1.069 g) as light yellow oil.

¹H-NMR (500 MHz, CDCl₃) d: 2.17 (s, 3H), 3.4–4.9 (b, 10H), 6.69 (dd, 1H), 6.71 (d, 1H), 7.05 (d, 1H)

Example 75

Preparation of 4-methyl-3-valeramidobenzoic acid morpholide ([5]-(56)-278)

The aniline compound ([5]-(55)-278) (1.07 g) prepared in Example 74 was dissolved in anhydrous pyridine (20 ml), and the solution was cooled on ice. Valeryl chloride (0.60 ml) was added dropwise to the solution, and the solution was stirred on ice for 1 hour and further stirred at room temperature for 1.5 hours. The reaction solution was acidified with HCl, extracted with ethyl acetate, and concentrated. The crude product was purified by silica gel column chromatography (Kieselgel 60=80 g, ethyl acetate) to obtain the above-captioned compound ([5]-(56)-278) (1.32 g) as colorless clear oil.

¹H-NMR (500 MHz, CDCl₃) δ: 0.97 (t, 3H), 1.39–1.46 (m, 2H), 1.72 (quint 2H), 2.26 (s, 3H), 2.39(t, 2H), 3.4–4.9 (b, 8H), 7.10 (d, 1H), 7.17 (d, 1H), 7.44 (bs, 1H), 7.71 (s, 1H)

Example 76

Preparation of 4-methyl-3-N-[[4-(methoxycarbonylphenyl)methyl]valeramido]benzoic acid morpholide ([5]-(57)-278')

In anhydrous DMSO (5 ml), 50% NaH (140 mg) was suspended. A solution of the amide compound ([5]-(56)-278) (553 mg)prepared in Example 75 in DMSO (6 ml) was added dropwise to the suspension. After the resulting dark red suspension was stirred for 25 minutes, methyl 4-bromomethylbenzoate (458 mg) was added, and further the whole was stirred for 3 hours. The reaction solution was poured into water, extracted with chloroform, and concentrated. The crude product was purified by silica gel column chromatography (LiChroprep Si 60=80 g, ethyl acetate/ hexane=2/1) to obtain the above-captioned compound ([5]-(57)-278') (533 mg) as a white solid.

¹H-NMR (500 MHz, CDCl₃) δ: 0.82 (t, 3H), 1.17–1.23 (m, 2H) 1.54–1.60 (m, 2H), 1.88 (dt, 1H), 1.94 (dt, 1H), 2.16 (s, 3H), 2.80–3.85 (b, 8H), 3.91 (s, 3H), 4.19 (d, 1H), 5.51 (d, 1H), 6.70 (s, 1H), 7.27 (d, 2H), 7.35 (s, 2H), 7.93 (d, 2H)

Example 77

Preparation of 4-methyl-3-N-[[4-(carboxyphenyl) methyl]valeramido]benzoic acid morpholide ([5]-(57)-278) (Compound No. 278)

The ester compound ([5]-(57)-278') (300 mg) prepared in Example 76 was dissolved in a solvent of a mixture of methanol/THF (1/1) (10 ml). Then, 1N NaOH aqueous solution (1.5 ml) was added to the solution. The mixture was allowed to stand for 17 hours. The reaction solution was adjusted to pH 4 with 1N HCl, and concentrated. The crude product was purified by silica gel column chromatography (Kieselgel 60=25 g, chloroform/methanol=15/1) to obtain the above-captioned compound ([5]-(57)-278) (compound No. 278) (215 mg) as a white solid.

¹H-NMR 500 MHz, CDCl₃) δ: 0.82 (t, 3H), 1.20–1.25 (m, 2H) 1.58 (quint), 1.89 (dt, 1H), 2.00 (dt, 1H), 2.18 (s, 3H), 2.80–3.25 (b, 2H), 3.35–3.85 (b, 6H), 4.18 (d, 1H), 5.55 (d, 1H), 6.71 (s, 1H), 7.34 (d, 2H), 7.36 (s, 2H), 7.97 (d, 2H)

Example 78

Preparation of 4-dimethylamino-3-N-[[4-(1-triphenylmethyl-1H-tetrazol-5-yl)phenylmethyl] valeramido]benzoic acid morpholide ([5]-(57)-604')

After oil of 60% NaH (0.3764 g) was removed by washing with hexane, anhydrous dimethyl sulfoxide (DMSO) (15.7 ml) was added to the solution. The mixture was stirred at room temperature for 30 minutes. A solution of the compound ([5]-(56)-591) (1.9608 g) prepared in Example 51 in anhydrous DMSO (15.7 ml) was added dropwise at room temperature to obtain a light yellow solution. To the solution, a solution of 5-(4-bromomethylphenyl)-1H-(N-triphenylmethyl)tetrazole (4.2463 g) in anhydrous DMSO (21.2 ml) was added dropwise. After the resulting white suspension was stirred at room temperature for 2 hours to obtain a yellowish brown solution, the reaction solution was poured into water. Saturated brine was added to the mixture, and the whole was extracted with ethyl acetate. The ethyl acetate layer was washed with saturated brine, dried over anhydrous sodium sulfate, and concentrated to obtain yellowish brown oil (5.9581 g). The crude oil was purified by silica gel column chromatography (Kieselgel 60=280 g, chloroform/acetone= 20/1) to obtain the above-captioned compound ([5]-(57)-604') (4.2329 g) as light yellow foam.

¹H-NMR (500 MHz, CDCl₃) δ: 0.85 (t, 3H), 1.24 (sext, 2H), 1.63 (quint, 2H), 2.10 (dt, 1H), 2.27 (dt, 1H), 2.88 (s, 6H), 2.95–3.85 (b, 8H), 4.14 (d, 1H), 5.77 (d, 1H), 6.51 (s, 1H), 7.00 (d, 1H), 7.13–7.37 (m, 18H), 7.95 (d, 2H)

Example 79

Preparation of 4-dimethylamino-3-N-[[4-(1H-tetrazol-5-yl)phenylmethyl]valeramido]benzoic acid morpholide ([5]-(57)-604) (Compound No. 604)

The compound ([5]-(57)-604') (4.1872 g) prepared in Example 78 was dissolved in tetrahydrofuran (63 ml), and 12% HCl (31 ml) was added thereto. The solution was allowed to stand at room temperature for 2 hours. To the reaction solution, 20% NaOH aqueous solution was added, and the product was extracted as sodium salt, and washed with diethyl ether. The aqueous layer was adjusted to pH 4 with concentrated hydrochloric acid, and extracted with chloroform. The chloroform layer was washed with saturated brine, dried over anhydrous sodium sulfate, and concentrated to obtain yellow foam (2.6963 g). The crude foam was purified by silica gel column chromatography (kieselgel 60=150 g, chloroform/methanol=5/1) to obtain the above-captioned compound ([5]-(57)-604) (Compound No. 604) (2.6132 g) as light yellow foam.

¹H-NMR (500 MHz, CDCl₃) δ: 0.79 (t, 3H), 1.22 (tq, 2H), 1.63 (quint, 2H), 2.23 (dt, 1H), 2.31 (dt, 1H), 2.92 (s, 6H), 3.0–3.85 (b, 8H), 4.21 (d, 1H), 5.72 (d, 1H), 6.69 (s, 1H), 7.05 (d, 1H), 7.29 (d, 2H), 7.37 (d, 1H), 8.00 (d, 2H)

Example 80

Preparation of 3-n-amylamino-4-dimethylaminobenzoic acid morpholide ([7]-(71)-252)

The compound ([5]-(55)-591) (50 mg) prepared in Example 50 was dissolved in ethanol (1 ml), and 5% Pd/C (5 mg) was added thereto. Under a hydrogen gas atmosphere, valeraldehyde (0.03 ml) was added to the mixture, and the mixture was stirred at room temperature for 1 hour. After the reaction was completed, the catalyst was removed by filtration through celite, and solution was concentrated. The residue was purified by preparative thin layer chromatography (Merck 13872, hexane/ethyl acetate=1/2) to obtain the above-captioned compound ([7]-(71)-252) (39 mg) as colorless oil.

¹H-NMR (500 MHz, CDCl₃) δ: 0.92 (t, 3H), 1.3–1.4 (m, 4H), 1.67 (quint, 2H), 2.67 (s, 6H), 3.10 (t, 2H), 3.4–3.9 (br, 8H), 4.59 (br, 1H), 6.61 (s, 1H), 6.70 (d, 1H), 6.96 (d, 1H)

Example 81

Preparation of 4-dimethylamino-3-[N-(4-methoxycarbonylphenyl)methyl]-n-amylaminobenzoic acid morpholide ([7]-(72)-252')

The compound ([7]-(71)-252) (107 mg) prepared in Example 80 was dissolved in chloroform (2.5 ml). Then, methyl 4-(bromomethyl)benzoate (154 mg) and diisopropylethylamine (432 mg) were added to the solution. The mixture was heated under reflux for 3 days. After the reaction was completed, the solution was concentrated, and the residue was purified by silica gel column chromatography (Kieselgel 60=7 g, ethyl acetate/hexane=1/2) to obtain the above-captioned compound ([7]-(72)-252') (134 mg) as colorless oil.

$^1$H-NMR (500 MHz, CDCl$_3$) δ: 0.84 (t, 3H), 1.1–1.3 (m, 4H), 1.48 (quint, 2H), 2.93 (s, 6H), 3.07 (t, 2H), 3.2–3.8 (br, 8H), 4.41 (d, 2H), 6.74 (d, 1H), 6.93 (d, 1H), 7.02 (dd, 1H), 7.13 (d, 2H), 7.88 (d, 2H)

Example 82

Preparation of 4-dimethylamino-3-[N-(4-carboxyphenyl)methyl]-n-amylaminobenzoic acid morpholide ([7]-(72)-252) (Compound No. 252)

The compound ([7]-(72)-252') (125 mg) prepared in Example 81 was dissolved in methanol (3 ml), and then 1N-NaOH aqueous solution (1 ml) was added to the solution. The mixture was stirred at room temperature for 5.5 hours. After the reaction was completed, the solution was adjusted to approximately pH 5 with 1N-HCl aqueous solution, and extracted with ethyl acetate. After the solution was dried over anhydrous sodium sulfate, the solvent was evaporated under reduced pressure. The residue was purified by silica gel column chromatography (Kieselgel 60=5 g, chloroform/methanol=10/1) to obtain the above-captioned compound ([7]-(72)-252) (Compound No. 252) (110 mg) as light yellow foam.

$^1$H-NMR (500 MHz, CDCl$_3$) δ: 0.84 (t, 3H), 1.2–1.3 (m, 4H), 1.49 (quint, 2H), 2.89 (s, 6H), 3.03 (t, 2H), 3.2–3.8 (br, 8H), 4.42 (d, 2H) 6.77 (s, 1H), 6.92 (d, 1H), 7.03 (d, 1H), 7.14 (d, 2H), 7.93 (d, 2H)

Example 83

Preparation of 3-nitrobenzoic acid morpholide ([13]-(132)-158)

In tetrahydrofuran (100 ml) and dichloromethane (100 ml), 3-nitrobenzoic acid (7.58 g) was dissolved. Then 1-hydroxybenzotriazole (6.74 g), 1-ethyl-3-(3-dimethylaminopropyl)carbodiimide hydrochloride (9.57 g), and morpholine (9.47 g) were added to the solution. The mixture was stirred at room temperature overnight. After the reaction was completed, chloroform was added to the solution. The mixture was washed with 1N-HCl aqueous solution, 1N-NaOH aqueous solution, and distilled water. The organic layer was dried over anhydrous sodium sulfate. The solvent was evaporated under reduced pressure, and the residue was purified by silica gel column chromatography (Kieselgel 60=160 g, ethyl acetate) to obtain the above-captioned compound ([13]-(132)-158) (9.62 g) as white crystals.

Melting point: 83.5°–85.0° C.

$^1$H-NMR (500 MHz, CDCl$_3$) δ: 3.4–4.1 (br, 8H), 7.64 (t, 1H), 7.77 (dd, 1H), 8.29 (s, 1H), 8.31 (dd, 1H)

Example 84

Preparation of 3-aminobenzoic acid morpholide ([13]-(133)-158)

The compound ([13]-(132)-158) (8.63 g) prepared in Example 83 was dissolved in ethanol (400 ml), and the solution was heated to 50° C. To the suspention, a solution of 10% Pd/C (2.25 g) in ethanol and hydrazine monohydrate (4.4 ml) were added to the solution. The mixture was stirred for 30 minutes. After the reaction was completed, the catalyst was removed by filtration through celite. The solution was concentrated, and the residue was purified by silica gel column chromatography (Kieselgel 60=120 g, ethyl acetate) to obtain the above-captioned compound ([13]-(133)-158) (7.57 g) as a white solid.

Melting point: 72.0°–74.0° C.

$^1$H-NMR (500 MHz, CDCl$_3$) δ: 3.2–4.0 (br, 8H), 6.6–6.8 (m, 3H), 7.17 (td, 1H)

Example 85

Preparation of 3-n-amylaminobenzoic acid morpholide ([13]-(134)-158)

The compound ([13]-(133)-158) (250 mg) prepared in Example 84 was dissolved in ethanol (5 ml), and 10% Pd/C (25 mg) was added to the solution. Under a hydrogen gas atmosphere, valeraldehyde (0.14 ml) was added to the mixture, and the mixture was stirred at room temperature for 3 hours. After the reaction was completed, the catalyst was removed by filtration through celite, and solution was concentrated. The residue was purified by silica gel column chromatography (Kieselgel 60=15 g, hexane/ethyl acetate=1/1) to obtain the above-captioned compound ([13]-(134)-158) (304 mg) as a white solid.

Melting point: 65.5°–67.0° C.

$^1$H-NMR (500 MHz, CDCl$_3$) δ: 0.93 (t, 3H), 1.3–1.4 (m, 4H), 1.62 (quint, 2H) 3.11 (t, 2H), 3.3–4.0 (br, 8H), 4.59 (bs, 1H), 6.1–6.5 (m, 3H), 7.17 (t, 1H)

Example 86

Preparation of 3-[N-(4-methoxycarbonylphenyl)methyl]-n-amylaminobenzoic acid morpholide ([13]-(135)-158')

The compound ([13]-(134)-158) (257 mg) prepared in Example 85 was dissolved in chloroform (7 ml), and methyl 4-bromomethylbenzoate and diisopropylethylamine (1.6 ml) were added to the solution. The mixture was heated under reflux for 3 days. After the reaction was completed, the solution was concentrated. The residue was purified by silica gel column chromatography (Kieselgel 60=39 g, ethyl acetate/hexane=1/1) to obtain the above-captioned compound ([13]-(135)-158') (395 mg) as colorless oil.

$^1$H-NMR (500 MHz, CDCl$_3$) δ: 0.90 (t, 3H), 1.3–1.4 (m, 4H), 1.66 (quint, 2H), 3.42 (t, 2H), 3.2–3.9 (br, 8H), 3.90 (s, 3H), 4.59 (s, 2H), 6.65–6.67 (m, 2H), 7.18 (t, 1H), 7.24 (d, 2H), 7.97 (d, 2H)

Example 87

Preparation of 3-[N-(4-carboxyphenyl)methyl]-n-amylaminobenzoic acid morpholide ([13]-(135)-158) (Compound No. 158)

The compound ([13]-(135)-158') (354 mg) prepared in Example 86 was dissolved in methanol (7.6 ml), and 1N NaOH aqueous solution (2 ml) was added to the solution. The mixture was stirred at room temperature for 19 hours. After the reaction was completed, the solution was adjusted to approximately pH 5 with 1N HCl aqueous solution, and extracted with ethyl acetate. After the solution was dried over anhydrous sodium sulfate, the solvent was evaporated under reduced pressure. The residue was purified by silica gel column chromatography (Kieselgel 60=10 g, chloroform/methanol=10/1) to obtain the above-captioned compound ([13]-(135)-158) (Compound No. 158) (327 mg) as light yellow foam.

Melting point: 64.0°–66.5° C.

$^1$H-NMR (500 MHz, CDCl$_3$) δ: 0.86 (t, 3H), 1.2–1.4 (m, 4H), 1.61 (quint, 2H), 3.37 (t, 2H), 3.2–4.0 (br, 8H), 4.54 (s, 2H), 6.56 (s, 1H), 6.61 (d, 2H), 7.13 (t, 1H), 7.20 (d, 2H), 7.95 (d, 2H)

Example 88

Preparation of 4-chloro-3-nitrobenzoic acid morpholide ([8]-(82)-41)

In thionyl chloride (10.0 ml), 4-chloro-3-nitrobenzoic acid (1.00 g) was dissolved, and the solution was heated at 80° C. for 5 hours. After cooling, thionyl chloride was evaporated under reduced pressure to dryness. The residue was dissolved in dichloromethane (10 ml), and morpholine (0.87 ml) was added to the solution while cooling on ice. After stirring for 1 hour on ice, distilled water (10 ml) was added to the solution. The whole was extracted with dichloromethane (20 ml). The organic layer was concentrated, and the residue was purified by silica gel column chromatography (Kieselgel 60=25 g, dichloromethane) to obtain the above-captioned compound ([8]-(82)-41) (0.966 g) as a light yellow solid.

$^1$H-NMR (500 MHz, CDCl$_3$) δ: 3.48 (bs, 2H), 3.80 (bs, 6H), 7.56 (dd, 1H), 7.63 (d, 1H), 7.94 (d, 1H)

Example 89

Preparation of 4-n-amylamino-3-nitrobenzoic acid morpholide ([8]-(83)-41)

Morpholine amide ([8]-(82)-41) (0.60 g) prepared in Example 88 was dissolved in a mixture of ethanol (5 ml) and THF (5 ml), and n-amylamine (0.52 ml) was added to the solution. The mixture was reacted at 90° C. for 19 hours. The solvent was evaporated, and the residue was extracted with chloroform (100 ml) twice. After the organic layer was dried over anhydrous sodium sulfate, the organic layer was concentrated to obtain the above-captioned compound ([8]-(83)-41) (0.708 g) as a yellow solid.

$^1$H-NMR (500 MHz, CDCl$_3$) δ: 0.92 (t, 3H), 1.36–1.55 (m, 4H), 1.75 (quint 2H), 3.33 (td, 2H), 3.67 (bs, 4H), 3.71 (bs, 4H), 6.89 (d, 1H), 7.58 (dd, 1H), 8.22 (bs, 1H), 8.29 (d, 1H)

Example 90

Preparation of 4-(N-n-amyl-N-methyl)amino-3-nitrobenzoic acid morpholide ([8]-(84)-41)

The compound ([8]-(83)-41) (3.60 g) prepared in Example 89 was dissolved in DMF (20 ml), and silver (I) oxide (12.0 g) and methyl iodide (15.0 g) were added to the solution. The mixture was stirred at room temperature for 3 days. The insolubles were filtered out through a glass filter G4. The filtrate was diluted with ethyl acetate (100 ml), and washed with 1N HCl aqueous solution. After the organic layer was concentrated, the residue was purified by silica gel column chromatography [Kieselgel 60=90 g, hexane/ethyl acetate (from 3/1 to 2/1 to 1/1)] to obtain the above-captioned compound ([8]-(84)-41) (3.00 g) as orange oil.

$^1$H-NMR (500 MHz, CDCl$_3$) δ: 0.90 (t, 3H), 1.20–1.38 (m, 4H), 1.64 (quint, 2H), 2.85 (s, 3H), 3.24 (t, 2H), 3.65 (bs, 4H), 3.71 (bs, 4H), 7.04 (d, 1H), 7.48 (dd, 1H), 7.85 (d, 1H)

Example 91

Preparation of 3-amino-4-(N-n-amyl-N-methyl)aminobenzoic acid morpholide ([8]-(85)-41)

The nitro compound ([8]-(84)-41) (1.06 g) prepared in Example 90 was dissolved in a mixture of methanol (40 ml) and distilled water (40 ml), and sodium hydrosulfite (2.79 g) was added to the solution. The mixture was stirred at room temperature for 1 hour. The reaction solution was adjusted to pH 7 with sodium carbonate, and extracted with chloroform (100 ml). After the organic layer was dried over anhydrous sodium sulfate, the residue was concentrated to obtain the above-captioned compound ([8]-(85)-41) (0.914 g) as colorless oil.

$^1$H-NMR (500 MHz, CDCl$_3$) δ: 0.88 (t, 3H), 1.25–1.35 (m, 4H) 1.49 (quint, 2H), 2.62 (s, 3H), 2.84 (t, 3H), 3.68 (bs, 8H), 4.06 (bs, 2H), 6.73 (dd, 1H), 6.77 (d, 1H), 6.98 (d, 1H)

Example 92

Preparation of 4-(N-n-amyl-N-methyl)amino-3-[(4-methoxycarbonylphenyl)methyl]aminobenzoic acid morpholide ([8]-(86)-41')

The aniline compound ([8]-(85)-41) (366 mg) prepared in Example 91 was dissolved in acetic acid (5.5 ml), and then 4-methoxycarbonylbenzaldehyde (266 mg) was added to the solution. The mixture was stirred at room temperature for 1 hour. Borane-dimethylamine complex (83 mg) was added to the reaction solution, and the mixture was stirred at the same temperature for 17 hours. Toluene was added to the reaction solution. The mixture was concentrated to remove acetic acid, and adjusted to pH 14 with 1N NaOH aqueous solution. The mixture was extracted with chloroform, and the organic layer was concentrated. Further, benzene was added to the residue, and the mixture was azeortopically distilled off. The resulting crude product was purified by preparative thin layer chromatography [Merck 5717, benzene/ethyl acetate=3/1) to obtain the above-captioned compound ([8]-(86)-41') (150 mg) as light yellow oil.

$^1$H-NMR (500 MHz, CDCl$_3$) δ: 0.86 (t, 3H), 1.20–1.33 (m, 4H), 1.48 (quint, 2H), 2.63 (s, 3H), 2.84 (t, 3H), 3.10–3.90 (br, 8H), 3.91 (s, 3H), 4.43 (d, 2H), 5.34 (t, 1H), 6.47 (d, 1H), 6.72 (dd, 1H), 7.02 (d, 1H), 7.40 (d, 2H), 8.00 (d, 2)

Example 93

Preparation of 4-(N-n-amyl-N-methyl)amino-3-[(4-carboxyphenyl)methyl]aminobenzoic acid morpholide ([8]-(86)-41) (Compound No 41)

The aniline compound ([8]-(85)-41) (5.45 g) prepared in Example 91 was dissolved in toluene (210 ml). Then, diisopropylethylamine (23.0 g) and methyl 4-bromomethylbenzoate (6.23 g) were added to the solution. The mixture was stirred at 90° C. for 48 hours under a nitrogen gas atmosphere. The reaction solution was concentrated, and the residue was purified by silica gel column chromatography (Kieselgel 60=300 g, chloroform) to obtain a fraction (4.34 g) including the above compound ([8]-(86)-41') as light yellow oil.

The resulting oil was dissolved in methanol (50 ml) and THF (50 ml), and 1N NaOH aqueous solution (15 ml) was added to the solution. The mixture was allowed to stand for 63 hours. After the reaction solution was adjusted to pH 4 with 1N HCl aqueous solution, the solution was extracted with chloroform (200 ml). After the organic layer was concentrated, the residue was purified by silica gel column chromatography (Kieselgel 60=400 g, chloroform/methanol=15/1) to obtain the above-captioned compound ([8]-(86)-41) (Compound No. 41) (2.50 g) as light yellow foam.

$^1$H-NMR (500 MHz, CDCl$_3$) δ: 0.86 (t, 3H), 1.22–1.35 (m, 4H), 1.48 (quint, 2H), 2.61 (s, 3H), 2.85 (t, 2H), 3.20–3.85 (br, 8H), 4.46 (s, 2H), 5.39 (br, 1H), 6.49 (d, 1H), 6.73 (dd, 1H), 7.03 (d, 1H), 7.43 (d, 1H), 8.05 (d, 2H)

Example 94

Preparation of 2-chloroisonicotinic acid ([9]-(92)-467)

Phosphorus oxychloride (220.7 g) was added to isonicotinic acid N-oxide (50.064 g), and the mixture was stirred on an oil bath at 120° C. for 7 hours. The reaction mixture was slowly poured into ice water with vigorously stirring to precipitate light yellow crystals. The mixture was adjusted to approximately pH 4 with 4N NaOH aqueous solution. The resulting crystals were filtered out, washed with water, and dried by vacuum heating (60° C.) to obtain the above-captioned compound ([9]-(92)-467) (37.845 g).

Melting point: 233.0°–234.0° C.

$^1$H-NMR (500 MHz, d$_6$-DMSO) δ: 7.82 (dd, 1H), 7.84 (s, 1H), 8.61 (d, 1H), 13.91 (b, 1H)

Example 95

Preparation of 2-aminoisonicotinic acid ([9]-(93)-467)

To the compound ([9]-(92)-467) (31.5 g) prepared in Example 94, 25% ammonia aqueous solution (1500 ml) was added. The reaction was performed at 190° C. for 43 hours in an autoclave (pressure resistance=41 kg/cm$^2$). The reaction mixture was concentrated to approximately 200 ml. The residue was adjusted to pH 0.8 with 6N HCl, and the precipitated crystals (unreactive starting compound=2.2 g) were filtered out. The filtrate was adjusted to pH 6 with sodium hydrogencarbonate. The precipitated crystals were filtered out, washed with water, and dried to obtain the above-captioned compound ([9]-(93)-467) (21.5 g).

Melting point: >280° C.

$^1$H-NMR (500 MHz, d$_6$-DMSO) δ: 6.22 (s, 2H), 6.87 (dd, 1H), 6.93 (s, 1H), 8.03 (d, 1H)

Example 96

Preparation of ethyl 2-aminoisonicotinate ([9]-(93)-467')

Hydrogen chloride gas was blown into a suspension of the compound ([9]-(93)-467) (5.2130 g) prepared in Example 95 in anhydrous ethanol (80 ml) for 20 minutes, and the suspension was refluxed. The resulting yellow solution was stirred at room temperature for 20 hours, and concentrated. The residue was diluted with chloroform. The solution was washed with saturated sodium hydrogencarbonate aqueous solution and saturated brine. The organic layer was dried over anhydrous sodium sulfate, and concentrated. The resulting yellow crystals (6.1162 g) were recrystallized from n-hexane/ethyl acetate to obtain the above-captioned compound ([9]-(93)-467') (4.7881 g).

Melting point: 119.0°–121.0° C.

$^1$H-NMR (500 MHz, CDCl$_3$) δ: 1.39 (t, 3H), 4.37 (q, 2H), 4.60 (bs, 2H), 7.07 (s, 1H), 7.17 (dd, 1H), 8.18 (d, 1H)

Example 97

Preparation of ethyl 2-valeramidoisonicotinate ([9]-(94)-467)

The compound ([9]-(93)-467') (2.0691 g) prepared in Example 96 was dissolved in anhydrous pyridine (25 ml), and valeryl chloride (1.5 ml) was added dropwise to the solution with stirring and cooling on ice. After stirring and cooling on ice for 1 hour, the reaction solution was poured into ice water. The solution was extracted with ethyl acetate, washed with water and saturated brine, dried over anhydrous sodium sulfate, and concentrated. The resulting light yellow oil (3.2548 g) was purified by silica gel column chromatography (Kieselgel 60=160 g, hexane/ethyl acetate=5/1) to obtain the above-captioned compound ([9]-(94)-467) (3.0820 g) as white crystals.

Melting point: 46.0°–47.0° C.

$^1$H-NMR (500 MHz, CDCl$_3$) δ: 0.96 (t, 3H), 1.41 (t, 3H), 1.43 (sext, 2H), 1.74 (quint, 2H), 2.42 (t, 2H), 4.41 (q, 2H), 7.60 (dd, 1H), 8.04 (bs, 1H), 8.38 (dd, 1H), 8.74 (s, 1H)

Example 98

Preparation of 2-valeramidoisonicotinic acid ([9]-(94)-467')

The compound ([9]-(94)-467) (14.281 g) prepared in Example 97 was dissolved in a mixture of methanol (114 ml) and tetrahydrofuran (114 ml). Then, 1N NaOH aqueous solution (114 ml) was added to the solution. The mixture was allowed to stand at room temperature for 1.5 hours. The reaction solution was adjusted to pH 3 with 1N HCl aqueous solution. The precipitated crystals were filtered out, and washed with water. The filtrate was concentrated, and the precipitated crystals were washed. The precipitated crystals and the above crystals were combined, and dried by vacuum heating (60° C.) to obtain the above-captioned compound ([9]-(94)-467') (12.335 g) as white crystals.

Melting point: 255.0°–256.0° C.

$^1$H-NMR (500 MHz, CDCl$_3$) δ: 0.89 (t, 3H), 1.32 (sext, 2H), 1.57 (quint, 2H), 2.42 (t, 2H), 7.49 (dd, 1H), 8.46 (dd, 1H), 8.59 (s, 1H), 10.64 (s, 1H), 13.58 (b, 1H)

Example 99

Preparation of 2-valeramidoisonicotinic acid morpholide ([9]-(94)-467")

The compound ([9]-(94)-467') (2.4610 g) prepared in Example 98 was dissolved in anhydrous dimethylformamide (DMF) (37 ml). Then, 1-hydroxybenzotriazole (1.9477 g), N,N'-dicyclohexylcarbodiimide (2.9739 g), and morpholine (1.3 ml) were added to the solution. The mixture was stirred at room temperature for 16 hours. The insolubles were filtered out, and the filtrate was concentrated. The resulting residue was dissolved in chloroform, washed with water and saturated brine, dried over anhydrous sodium sulfate, and concentrated to obtain yellowish brown oil (7.4981 g). The crude oil was purified by silica gel column chromatography (Kieselgel 60=230 g, chloroform/acetone=5/1) to obtain the above-captioned compound ([9]-(94)-467") (3.1756 g) as white crystals.

Melting point: 110.0°–112.0° C.

$^1$H-NMR (500 MHz, CDCl$_3$) δ: 0.88 (t, 3H), 1.34 (sext, 2H), 1.64 (quint, 2H), 2.34 (t, 2H), 3.35 (bs, 2H), 3.58 (bs, 2H), 3.71 (bs, 4H), 6.99 (dd, 1H), 8.12 (s, 1H), 8.17 (s, 1H), 8.26 (d, 1H)

Example 100

Preparation of 2-N-[[(4-methoxycarbonylphenyl) methyl]valeramido]isonicotinic acid morpholide ([9]-(95)-467')

After oil of 60% NaH (3.160 g) was removed by washing with hexane, anhydrous dimethyl sulfoxide (DMSO) (120 ml) was added to the solution. The mixture was stirred at room temperature for 15 minutes. A solution of the compound ([9]-(94)-467") (15.342 g) prepared in Example 99 in anhydrous DMSO (120 ml) was added dropwise at room temperature to obtain a yellow suspension. To the suspension, a solution of methyl 4-(bromomethyl)benzoate (14.476 g) in anhydrous DMSO (120 ml) was added dropwise. After the resulting yellowish orange suspension was stirred at room temperature for 2 hours, the reaction mixture was poured into ice water, and the whole was extracted with chloroform. The chloroform layer was washed with water and saturated brine, dried over anhydrous sodium sulfate, and concentrated to obtain yellowish brown oil (26.381 g). The crude oil was purified by silica gel column chromatography (Kieselgel 60=1.3 kg, chloroform/acetone=15/1) to obtain the above-captioned compound ([9]-(95)-467') (17.277 g) as yellow oil.

$^1$H-NMR (500 MHz, CDCl$_3$) δ: 0.85 (t, 3H), 1.27 (sext, 2H), 1.63 (quint, 2H), 2.33 (t, 2H), 3.22 (bs, 2H), 3.55 (bs, 2H), 3.75 (bs, 4H), 3.90 (s, 3H), 5.20 (s, 2H), 7.15 (dd, 1H), 7.2–7.35 (b, 1H), 7.29 (d, 2H), 7.96 (d, 2H), 8.53 (d, 1H)

Example 101

Preparation of 2-N-[[(4-carboxyphenyl)methyl] valeramido]isonicotinic acid morpholide ([9]-(95)-467) (Compound No. 467)

The compound ([9]-(95)-467') (0.9030 g) prepared in Example 100 was dissolved in a mixture of methanol (7.2 ml) and tetrahydrofuran (7.2 ml). Then, a solution of sodium hydrogencarbonate (0.2590 g) in distilled water (14.4 ml) was added to the solution. The mixture was heated under reflux on an oil bath at 100° C. for 8.5 hours. After the reaction solution was cooled, the solution was adjusted to pH 4 with 1N HCl aqueous solution (2.9 ml), and concentrated. The residue was diluted with chloroform. The solution was washed with saturated brine, dried over anhydrous sodium sulfate, and concentrated. The resulting yellowish brown oil (0.6530 g) were purified by silica gel column chromatography (Kieselgel 60=33 g, chloroform/methanol= 15/1) to obtain the above-captioned compound ([9]-(95)-467) (Compound No. 467) (0.4061 g) as white crystals.

Melting point: 152.0°–155.0° C.

$^1$H-NMR (500 MHz, CDCl$_3$) δ: 0.85 (t, 3H), 1.27 (sext, 2H), 1.63 (quint, 2H), 2.34 (t, 2H), 3.24 (bs, 2H), 3.56 (bs, 2H), 3.75 (s, 4H), 5.21 (s, 2H), 7.17 (t, 1H), 7.2–7.35 (b, 1H), 7.31 (d, 2H), 7.98 (d, 2H), 8.54 (d, 1H)

Example 102

Preparation of 2-n-amylaminoisonicotinic acid morpholide ([10]-(103)-535)

To 2-chloroisonicotinic acid morpholide (407 mg), n-amylamine (15 ml) was added, and the mixture was heated on an oil bath at 110° C. for 56 hours under a nitrogen gas atmosphere. The reaction solution was concentrated, and washed with chloroform/water. After concentration, the crude product was purified by silica gel column chromatography [LiChroprep Si 60=70 g, chloroform/methanol (from 60/1 to 40/1)] to obtain the above-captioned compound ([10]-(103)-535) (349 mg) as light yellow oil.

$^1$H-NMR (500 MHz, CDCl$_3$) δ: 0.91 (t, 3H), 1.33–1.45 (m, 4H), 1.75 (quint, 2H), 3.23 (q, 2H), 3.41 (bs, 2H), 3.77 (bs, 2H), 4.85 (bs, 4H), 6.36 (s, 1H), 6.49 (dd, 1H), 8.10 (d, 1H)

Example 103

Preparation of 2-[N-n-amyl-N-(4-methoxycarbonylphenyl)methyl]aminoisonicotinic acid morpholide ([10]-(104)-535')

The compound ([10]-(103)-535) (4.58 g) prepared in Example 102 was dissolved in toluene (100 ml). Then, diisopropylethylamine (21.3 g) and methyl 4-bromomethylbenzoate (4.16 g) were added to the solution. After the solution was degassed by sonication, the solution was heated on an oil bath at 110° C. for 24 hours under a nitrogen gas atmosphere. The reaction solution was concentrated, and extracted with chloroform. After concentration, the crude product was purified by silica gel column chromatography (Kieselgel 60=100 g, ethyl acetate) to obtain a fraction (6.10 g) including the starting compound and the desired product. Further, the fraction was purified by silica gel column chromatography [Kieselgel 60=240 g, hexane/ethyl acetate (from 1/2 to 1/1)] to obtain the above-captioned compound ([10]-(104)-535') (3.15 g) as colorless oil.

$^1$H-NMR (500 MHz, CDCl$_3$) δ: 0.89 (t, 3H), 1.25–1.37 (m, 4H), 1.61 (quint, 2H), 3.32 (bs, 2H), 3.45–3.50 (b, 4H), 3.74 (bs, 4H), 3.97 (s, 3H), 4.83 (s, 2H), 6.37 (s, 1H), 6.49 (dd, 1H), 7.23 (d, 2H), 7.96 (d, 2H), 8.19 (d, 1H)

Example 104

Preparation of 2-[N-n-amyl-N-(4-carboxyphenyl) methyl]aminoisonicotinic acid morpholide ([10]-(104)-535) (Compound No. 535)

The ester compound ([10]-(104)-535') (5.12 g) prepared in Example 103 was dissolved in a mixture of dioxane/water (1/1) (100 ml). Then, 1N NaOH aqueous solution (16 ml) was added to the solution. The mixture was allowed to stand at room temperature for 6 hours. The reaction solution was adjusted to pH 2 with 1N HCl aqueous solution, and extracted with chloroform. After the reaction solution was concentrated, the crude product was purified by silica gel column chromatography [Kieselgel 60=250 g, chloroform/methanol (from 15/1 to 10/1)] to obtain the above-captioned compound ([10]-(104)-535) (Compound No. 535) (4.34 g) as white crystals.

$^1$H-NMR (500 MHz, CDCl$_3$) δ: 0.88 (t, 3H), 1.28–1.37 (m, 4H), 1.63 (quint, 2H), 3.33 (bs, 2H), 3.48 (t, 2H), 3.52 (bs, 2H), 3.74 (bs, 4H), 4.85 (s, 2H), 6.41 (s, 1H), 6.50 (d, 1H), 7.27 (d, 2H), 7.99 (d, 2H), 8.20 (d, 1H)

Example 105

Preparation of 4-[(4-dimethylamino-3-nitrobenzene) sulfonyl]morpholine ([11]-(113)-597)

In dioxane (120 ml), 4-[(4-chloro-3-nitrobenzene) sulfonyl]morpholine ([2]-(22)-596) (10.45 g) was dissolved.

Then, triethylamine (9.50 ml) and dimethylamine hydrochloride (4.23 g) were added to the solution. The mixture was heated in a reactor made of pressure glass at 80° C. for 64 hours. The reaction solution was extracted with chloroform (100 ml) three times. The organic layer was dried over anhydrous sodium sulfate, and the solvent was evaporated to obtain the above-captioned compound ([11]-(113)-597) (10.7 g) as a yellow solid.

$^1$H-NMR (500 MHz, CDCl$_3$) δ: 3.02 (t-like, 4H), 3.06 (s, 6H), 3.76 (t-like, 4H), 7.06 (d, 1H), 7.68 (dd, 1H), 8.15 (d, 1H)

Example 106

Preparation of 4-[(3-amino-4-dimethylaminobenzene)sulfonyl]morpholine ([11]-(114)-597)

The nitro compound ([11]-(113)-597) (4.83 g) prepared in Example 105 was dissolved in a mixture of THF (80 ml) and distilled water (80 ml). Then, sodium hydrosulfite (12.7 g) was added to the solution, and stirred at room temperature for 2 hours. The reaction solution was made alkaline with sodium hydrogencarbonate, and extracted with chloroform (100 ml) twice. The organic layer was dried over anhydrous sodium sulfate, and the solvent was evaporated to obtain the above-captioned compound ([11]-(114)-597) (3.23 g) as a light yellow solid.

$^1$H-NMR (500 MHz, CDCl$_3$) δ: 2.72 (s, 6H), 3.00 (t-like, 4H), 3.74 (t-like, 4H), 4.07 (bs, 2H), 7.04 (m, 2H), 7.10 (dd, 1H)

Example 107

Preparation of 4-[(4-dimethylamino-3-valeramidobenzene)sulfonyl]morpholine ([11]-(115)-597)

The compound ([11]-(114)-597) (2.73 g) prepared in Example 106 was dissolved in anhydrous pyridine (80 ml), and the solution was cooled on ice. Valeryl chloride (1.13 ml) was added dropwise to the solution. The mixture was stirred at the same temperature for 100 minutes, and stirred at room temperature for 30 minutes. The reaction mixture was concentrated, and the residue was extracted with chloroform (100 ml) twice. The organic layer was concentrated, and pyridine was removed by azeotropically distilling off with toluene. The resulting product was purified by silica gel column chromatography (Kieselgel 60=250 g, chloroform/methanol=60/1) to obtain the above-captioned compound ([11]-(115)-597) (1.97 g) as a white solid.

$^1$H-NMR (500 MHz, CDCl$_3$) δ: 0.97 (t, 3H), 1.40–1.48 (m, 2H), 1.74 (quint, 2H), 2.44 (t, 2H), 2.71 (s, 6H), 3.06 (t-like, 4H), 3.74 (t-like, 4H), 7.23 (d, 1H), 7.41 (dd, 1H), 8.14 (bs, 1H), 8.73 (bs, 1H)

Example 108

Preparation of 4-[[4-dimethylamino-3-N-[(4-methoxycarbonylphenyl)methyl]valeramidobenzene]sulfonyl]morpholine ([11]-(116)-597')

NaH (0.36 g) (50% content) was suspended in DMSO (20 ml). A solution of the compound ([11]-(115)-597) (1.97 g) prepared in Example 107 in DMSO (23 ml) was added to the suspension. After 15 minutes, a solution of methyl 4-bromomethylbenzoate (1.50 g) in DMSO (20 ml) was added to the mixture, and the mixture was stirred at room temperature for 1.5 hours. The reaction solution was poured into 1N HCl aqueous solution (100 ml), and the whole was extracted with ethyl acetate (100 ml) twice. The organic layer was concentrated, and the resulting crude product was purified by silica gel column chromatography (Kieselgel 60=250 g, chloroform/methanol=80/1) to obtain the above-captioned compound ([11]-(116)-597') (2.26 g) as a white solid.

$^1$H-NMR (500 MHz, CDCl$_3$) δ: 0.86 (t, 3H), 1.20–1.33 (m, 2H), 1.62–1.69 (m, 2H), 1.98 (td, 1H), 2.31 (td, 1H), 2.50–2.60 (bm, 2H), 2.60–2.70 (bm, 2H), 2.98 (s, 6H), 3.55–3.63 (m, 4H), 3.87 (s, 3H), 4.04 (d, 1H), 5.80 (d, 1H), 6.87 (d, 1H), 7.00 (d, 1H), 7.21 (d, 2H), 7.51 (dd, 1H), 7.89 (d, 2H)

Example 109

Preparation of 4-[[3-N-[(4-carboxyphenyl)methyl]valeramido-4-dimethylaminobenzene]sulfonyl]morpholine ([11]-(116)-597) (Compound No. 597)

The methyl ester compound ([11]-(116)-597') (2.20 g) prepared in Example 108 was dissolved in a mixture of THF (25 ml) and methanol (25 ml). Then, 1N NaOH aqueous solution was added to the solution. The mixture was allowed to stand for 25.5 hours. The reaction solution was adjusted to pH 1 with 1N HCl aqueous solution, and the solvent was evaporated. To the residue, 1N HCl aqueous solution was added, and the whole was extracted with dichloromethane (40 ml) twice. The resulting crude product was purified by silica gel column chromatography (Kieselgel 60=125 g, from chloroform/methanol=30/1 to chloroform/methanol=20/1 to chloroform/methanol=10/1) to obtain the above-captioned compound ([11]-(116)-597) (Compound No. 597) (1.84 g) as a white solid.

$^1$H-NMR (500 MHz, CDCl$_3$) δ: 0.86 (t, 3H), 1.20–1.33 (m, 2H), 1.61–1.71 (m, 2H), 2.10 (td, 1H), 2.32 (td, 1H), 2.50–2.60 (bm, 2H), 2.60–2.70 (m, 2H), 2.99 (s, 6H), 3.60 (t-like, 4H), 4.07 (d, 1H), 5.79 (d, 1H, 6.88 (d, 1H), 7.01 (d, 1H), 7.23 (d, 2H), 7.52 (dd, 1H), 7.94 (d, 2H)

Example 110

Preparation of 4-dimethylamino-3-[N-(4-methoxycarbonylphenyl)methyl]aminobenzoic acid morpholide ([12]-(121)-225)

In acetic acid (15 ml), 4-dimethylamino-3-aminobenzoic acid morpholide ([5]-(55)-591) (1.00 g) was dissolved. Then, 4-methoxycarbonylbenzaldehyde (691 mg) was added. The solution became yellow immediately. The solution was stirred at room temperature for 4 hours. Then dimethylamine-borane complex (260 mg) was added to the solution, the mixture was stirred at room temperature for 1 hour. After the reaction was completed, distilled water was added to the solution. The solution was extracted with ethyl acetate, washed with saturated sodium hydrogencarbonate aqueous solution and distilled water, and dried over anhydrous sodium sulfate. The solvent was evaporated under reduced pressure, and the residue was purified by silica gel column chromatography (Kieselgel 60=60 g, hexane/ethyl acetate=1/1) to obtain the above-captioned compound ([12]-(121)-225) (1.44 g) as a white solid.

Melting point: 109.5°–110.0° C.

$^1$H-NMR (500 MHz, CDCl$_3$) δ: 2.69 (s, 6H), 3.0–3.9 (br, 8H), 3.91 (s, 3H), 4.44 (d, 1H), 5.21 (t, 1H), 6.47 (d, 1H), 6.74 (dd, 1H), 7.02 (d, 1H), 7.44 (d, 2H), 8.00 (d, 2H)

Example 111

Preparation of 4-dimethylamino-3-[1-(4-methoxycarbonylphenyl)methyl-3-propyl]ureidobenzoic acid morpholide ([12]-(122)-225')

The compound ([12]-(121)-225) (250 mg) prepared in Example 110 was dissolved in toluene (5 ml). Then, n-propyl isocyanate (0.118 ml) was added dropwise. The mixture was refluxed for 2 days. After the reaction was completed, the solvent was evaporated under reduced pressure. The residue was purified by silica gel column chromatography (LiChroprep Si 60=25 g, hexane/ethyl acetate=3/20) to obtain the above-captioned compound ([12]-(122)-225') (239 mg) as a white solid.

Melting point: 141.0°–142.0° C.

$^1$H-NMR (500 MHz, CDCl$_3$) δ: 0.84 (t, 3H), 1.45 (sext, 2H), 2.90 (s, 6H), 3.0–3.8 (br, 10H), 3.88 (s, 3H), 4.2–4.4 (br, 1H), 4.62 (t, 1H), 5.4–5.7 (br, 1H), 6.64 (d, 1H), 6.98 (d, 1H), 7.22 (d, 2H), 7.28 (dd, 1H), 7.85 (d, 2H)

Example 112

Preparation of 4-dimethylamino-3-[1-(4-carboxyphenyl)methyl-3-propyl]ureidobenzoic acid morpholine ([12]-(122)-225) (Compound No. 225)

The ester compound ([12]-(122)-225') (102 mg) prepared in Example 111 was dissolved in methanol (2 ml), and 1N NaOH aqueous solution (0.5 ml) was added to the solution. The mixture was stirred at room temperature for 2 days. After the reaction was completed, the solution was adjusted to pH 2-3 with 1N HCl aqueous solution. The solution was extracted with ethyl acetate, and dried over anhydrous sodium sulfate. The solvent was evaporated under reduced pressure. The residue was purified by preparative thin layer chromatography (Merck 13872, chloroform/methanol=20/3), and further recrystallized from chloroform/hexane to obtain the above-captioned compound ([12]-(122)-225) (Compound No. 225) (66 mg) as white plate crystals.

Melting point: 127.0°–130.5° C.

$^1$H-NMR (500 MHz, CDCl$_3$) δ: 0.76 (t, 3H), 1.37 (sext, 2H), 2.82 (s, 6H), 2.9–3.8 (br, 10H), 4.0–4.3 (br, 1H), 4.66 (t, 1H), 5.4–5.7 (br, 1H), 6.59 (d, 1H), 6.90 (d, 1H), 7.16 (d, 2H), 7.21 (dd, 1H), 7.80 (d, 2H)

Example 113

Acute Toxicity

Five-week-old ICR female mice (5 mice per group) were bred for acclimation for a week. Then, the compounds of the present invention were dissolved or dispersed in an aqueous solution of 0.5% methylcellulose, and orally administered to the mice in a single dosage (500 mg/kg). The number of deaths was observed for 6 days after the administration. The results are shown in Table 22.

TABLE 22

| Compound No. | Number of deaths/number of survivals |
|---|---|
| 1 | 0/5 |
| 41 | 0/5 |
| 90 | 0/5 |
| 158 | 0/5 |
| 184 | 0/5 |
| 225 | 0/5 |
| 252 | 0/5 |
| 278 | 0/5 |
| 372 | 0/5 |
| 467 | 0/5 |
| 535 | 0/5 |
| 585 | 0/5 |
| 586 | 0/5 |
| 587 | 0/5 |
| 591 | 0/5 |

TABLE 22-continued

| Compound No. | Number of deaths/number of survivals |
|---|---|
| 592 | 0/5 |
| 593 | 0/5 |
| 594 | 0/5 |
| 595 | 0/5 |
| 596 | 0/5 |
| 598 | 0/5 |
| 599 | 0/5 |
| 604 | 0/5 |

Example 114

Binding to Receptors

In this Example, the affinity to the angiotensin II receptor subtype 1 or subtype 2 was evaluated by a binding assay in accordance with the method described in Biochem. Pharmacol., 33, 4057–4062 (1984).

Specifically, the measurement of the total binding in the presence of each drug was performed as follows:

A mixture (final volume=0.25 ml) of a drug in a given concentration (the drug was dissolved in DMSO, and diluted to a double volume with a buffer attached to a drug discovery system to prepare sample for the assay; 0.025 ml), a tracer (0.025 ml), and receptors (0.2 ml) was incubated [in the case of the angiotensin II receptor subtype 1 (AT$_1$), at room temperature for 3 hours, and in the case of the subtype 2 (AT$_2$), at 37° C. for 1 hour]. Then, the reaction mixture was filtered with suction (GF/C filter was used in AT$_1$, and GF/B filter was used in AT$_2$). The filter papers after filtration with suction (the tracer bound to the receptors) were counted by a γ-well counter (ARC-500, Aloka). The non-specific bindings were measured by repeating the above method, except that a large excess amount of a displacer was added. The specific binding of the drug in the given concentration was calculated by subtracting the non-specific binding from the total binding, respectively.

In AT$_1$ and AT$_2$, the percentages to inhibit the bindings of radioactive ligands (tracer) to receptors by the drugs to be tested (IC$_{50}$ value of concentration to show 50% inhibition, or binding inhibition % in 100 μM) were measured, using the drugs to be tested and control drugs in the given concentration. The results are shown in Table 23.

TABLE 23

| Compound No. | IC$_{50}$ AT$_1$ (nM) | Binding inhibition % in 100 μm | |
|---|---|---|---|
| | | AT$_1$ | AT$_2$ |
| 1 | | 33 | 0 |
| 41 | | 26 | 0 |
| 75 | | 15 | 0 |
| 90 | | 30 | 0 |
| 158 | | 18 | 0 |
| 184 | | 0 | 0 |
| 225 | | 4 | 0 |
| 252 | | 34 | 0 |
| 278 | | 4 | 0 |
| 372 | | 2 | 0 |
| 467 | | 16 | 0 |
| 535 | 3800 | | 0 |
| 585 | 1700 | | 0 |
| 586 | 1200 | | 0 |
| 587 | 7900 | | 0 |
| 591 | | 35 | 0 |

TABLE 23-continued

| Compound No. | IC$_{50}$ AT$_1$ (nM) | Binding inhibition % in 100 μm | |
|---|---|---|---|
| | | AT$_1$ | AT$_2$ |
| 592 | 4900 | | 0 |
| 593 | | 36 | 0 |
| 594 | 32000 | | 0 |
| 595 | | 41 | 0 |
| 596 | | 22 | 0 |
| 597 | | 0 | 0 |
| 598 | | 36 | 0 |
| 599 | | 38 | 0 |
| 604 | | 15 | 0 |
| DuP753 | 20 | | 0 |

In AT$_1$,
receptor: from adrenal glands in rabbits
tracer: $^3$H-angiotensin II
control drug: DuP753
(displacer): DuP753
In AT$_2$,
receptor: from cerebellar cortex in bovine
tracer: $^{125}$I-Tyr$^4$-angiotensin II
control drug: angiotensin II (human)
(displacer): angiotensin II (human)

As clear from Table 23, IC$_{50}$ values of the compounds of the present invention to the angiotensin II subtype 1 receptor were not less than 1000 nM, whereas IC$_{50}$ value of DuP753 used as a control substance was 20 nM. Therefore, it can be said that the compounds of the present invention having IC$_{50}$ values of not less than 1000 nM exhibit no inhibitory effect on the subtype 1 receptor. The fact that the compounds of the present invention exhibit no binding activity to the subtype 1 receptor shows that such compounds are completely different from conventional ACE inhibitors or angiotensin II antagonists in action mechanism.

Example 115

Action to Depress Blood Pressure

The compounds of the present invention and the reference substance were forcedly administered per os to kidney disease model rats, and the action to depress blood pressure was observed. The kidney disease model rats were prepared by ligature of branches of renal artery in accordance with the conventional method, that is, the left hilum renalis of Sprague-Dawley female rats was exposed under anesthesia, and one of four secondary branches of renal artery was left unligated, while the remaining three branches were ligated, respectively. After a week, the hilum renalis (artery, vein, and ureter) of the right kidney were further ligated to thereby prepare the rats whose renal function was lowered to approximately ⅛ of the normal function. Each group consisted of eight rats. The drugs to be tested (20 mg/kg) were administered to each administering group, and only water was administered to control group. After two days from the administration, the systolic blood pressure was measured by the tail cuff method using a blood pressure measuring apparatus (UR5000; Ueda). The average of the blood pressures is shown in Table 24.

TABLE 24

| Compound No. | Blood pressure (mmHg) |
|---|---|
| 1 | 196 |
| 41 | 195 |
| 90 | 194 |

TABLE 24-continued

| Compound No. | Blood pressure (mmHg) |
|---|---|
| 158 | 190 |
| 184 | 195 |
| 225 | 195 |
| 252 | 200 |
| 278 | 198 |
| 372 | 190 |
| 467 | 200 |
| 535 | 195 |
| 585 | 196 |
| 586 | 198 |
| 587 | 201 |
| 591 | 199 |
| 592 | 202 |
| 593 | 200 |
| 594 | 194 |
| 595 | 198 |
| 596 | 198 |
| 598 | 202 |
| 599 | 200 |
| 604 | 200 |
| control | 203 |
| DuP753 | 135 |

In comparison with the control group, the reference substance (DuP753) clearly showed the action to depress the blood pressure. On the contrary, influence on the blood pressure was not substantially shown in the compounds of this invention.

Example 116

Renal Function Indicatory Value (Action to Kidney Diseases)

The kidney disease model rats were prepared as in Example 115. Twenty-five groups (8 rats per group) were sleeked in a manner so that there were no major differences between each group in the serum creatinine value and the urea nitrogen value indicating renal function. The rats in each group were allowed to freely take up feed and water. To the rats in the administering group, the compounds of this invention or the reference substance (DuP753) were forcedly administered per os at the dose of 20 mg/kg/day every day. To the rats in the control group, only water was forcedly administered per os every day. After two weeks, 0.2 ml of blood was collected from the carotid artery of the rat under anesthesia, and centrifuged to obtain serum. Using 25 μl of the serum, serum creatinine (Scr) was measured by a creatinine analytical instrument (Beckman). Using 10 μl of the serum, urea nitrogen (BUN) was measured by a BUN analytical instrument (Beckman). Creatinine clearance was evaluated as follows:

After serum creatinine measurement, rats were placed in urinary metabolic cages for 24 hours to collect urine. Urinary creatine concentration (Ucr) was measured by a creatinine analytical instrument, and total volume of urination (Uvol) was also measured. Creatinine clearance (CCr) was calculated by the following formula:

$$CCr\ (ml/min) = \frac{Ucr\ (mg/dl) \times Uvol\ (ml)}{Scr\ (mg/dl) \times 24 \times 60\ (min)}$$

The results are shown in Table 25.

TABLE 25

| Compound No. | Creatinine mg/dl | Urea nitrogen mg/dl | Creatinine clearance ml/min |
|---|---|---|---|
| 1 | 1.6 | 75 | 0.34 |
| 41 | 1.6 | 72 | 0.36 |
| 90 | 1.5 | 70 | 0.38 |
| 158 | 1.7 | 74 | 0.37 |
| 184 | 1.5 | 70 | 0.38 |
| 225 | 1.8 | 73 | 0.25 |
| 252 | 1.7 | 73 | 0.28 |
| 278 | 1.8 | 73 | 0.36 |
| 372 | 1.7 | 72 | 0.36 |
| 467 | 1.8 | 74 | 0.25 |
| 535 | 1.5 | 72 | 0.38 |
| 585 | 1.6 | 72 | 0.35 |
| 586 | 1.7 | 76 | 0.33 |
| 587 | 1.7 | 77 | 0.34 |
| 591 | 1.6 | 76 | 0.33 |
| 592 | 1.7 | 76 | 0.33 |
| 593 | 1.6 | 80 | 0.31 |
| 594 | 1.7 | 77 | 0.30 |
| 595 | 1.5 | 73 | 0.38 |
| 596 | 1.6 | 78 | 0.34 |
| 598 | 1.6 | 80 | 0.35 |
| 599 | 1.5 | 73 | 0.35 |
| 604 | 1.8 | 75 | 0.28 |
| control | 2.0 | 100 | 0.20 |
| DuP753 | 1.6 | 80 | 0.32 |

When the compounds of the present invention were administered, the serum creatinine value and the urea nitrogen value which increase with aggravation of renal failure gen value clearly became lower values and creatinine clearance indicating renal function was clearly improved in comparison with the control substance. The pharmacological effects were comparable to those of the reference substance, and it was shown that the compounds of the present invention do not substantially exhibit conventional angiotensin II receptor antagonism and blood pressure depression action, but improve kidney diseases.

Example 117

Action to Survival Time of Kidney Diseased Animals

The kidney disease model rats were prepared as in Example 115. Twenty-five groups (8 rats per group) were prepared in a manner so that there was no major difference between the groups in the serum creatinine value and the urea nitrogen value indicating renal function. The rats in each group were allowed to freely take up feed and water. To the rats in the administering group, the compounds of the present invention or the reference substance (DuP753) were forcedly administered per os at the dose of 20 mg/kg/day every day. To the rats in the control group, only water was forcedly administered per os every day. If kidney diseases are aggravated, the rat will die of uremia. Thus, the survival time was observed as comprehensive indication of the improvement effect on the kidney diseases. The results are shown in Table 26. The observation period was eight weeks. Thus if all rats survived, the average survival time is eight weeks and it is an upper limit.

TABLE 26

| Compound No. | Average survival time (weeks) |
|---|---|
| 1 | 7.1 |
| 41 | 7.6 |
| 90 | 7.6 |
| 158 | 7.2 |
| 184 | 7.6 |
| 225 | 7.0 |
| 252 | 7.0 |
| 278 | 7.0 |
| 372 | 7.6 |
| 467 | 7.0 |
| 535 | 7.6 |
| 585 | 7.3 |
| 586 | 6.8 |
| 587 | 7.0 |
| 591 | 7.3 |
| 592 | 7.0 |
| 593 | 7.1 |
| 594 | 6.5 |
| 595 | 7.6 |
| 596 | 6.0 |
| 598 | 7.2 |
| 599 | 7.0 |
| 604 | 7.0 |
| control | 5.0 |
| DuP753 | 6.9 |

The compounds of the present invention clearly prolonged the survival time of the kidney disease model rats. The effect was comparable or superior to that of the reference substance. It was shown that the compounds of this invention do not substantially exhibit known angiotensin II receptor antagonism and blood pressure depression action, but prolonged the survival time of the rats which died of kidney diseases.

Example 118

The Compound No. 1 (10 mg), lactose (36 mg), corn starch (150 mg), microcrystalline cellulose (29 mg), and magnesium stearate (5 mg) were mixed, and tableted to prepare tablets (230 mg/tablet).

Although the present invention has been described with reference to specific embodiments, various changes and modifications obvious to those skilled in the art are deemed to be within the spirit, scope, and concept of the invention.

We claim:

1. A benzene derivative of the formula (I):

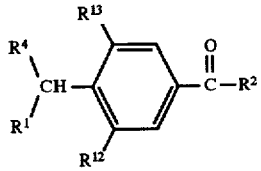

(I)

wherein $R^1$ is hydrogen, alkyl of 1 to 6 carbon atoms or haloalkyl of 1 to 6 carbon atoms; $R^2$ is hydroxyl, —$OR^{22}$, three-membered to seven-membered saturated cycloaliphatic amino group which may be interrupted by one or more nitrogen, oxygen or sulfur atoms, —$NHR^{23}$, —$N(R^{24})_2$ or —$NH_2$; $R^4$ is hydrogen or alkyl of 1 to 6 carbon atoms; $R^{12}$ is —$R^{11}$—$R^5$—; $R^{11}$ is —NH—, —$N(R^{26})$—, —$N(C(=O)R^{27})$—, —$N(C(=O)NH_2)$— or —$N(C(=O)NHR^{28})$—; $R^{13}$ is hydrogen atom, alkyl of 1 to 6 carbon atoms or haloalkyl of 1 to 6 carbon atoms; $R^5$ is —$CH_2C_6H_4COOH$, —$CH_2C_6H_4COOR^{31}$, —$CH_2C_6H_4OH$, —$CH_2C_6H_4OR^{32}$, —$CH_2C_6H_4NH_2$, —$CH_2C_6H_4N(R^{33})_2$, —$CH_2C_6H_4$-azole or —$CH_2C_6H_4NHR^{34}$; and $R^{22}$, $R^{23}$ $R^{24}$, $R^{26}$, $R^{27}$, $R^{28}$, $R^{31}$, $R^{32}$, $R^{33}$ and $R^{34}$ are independently an alkyl of 1 to 6 carbon atoms or haloalkyl group of 1 to 6 carbon atoms; or a salt thereof.

2. The benzene derivative of claim 1, wherein $R^1$ is hydrogen, alkyl of 1 to 5 carbon atoms or haloalkyl of 1 to 5 carbon atoms; $R^4$ is hydrogen or alkyl of 1 to 4 carbon atoms; $R^{13}$ is hydrogen, alkyl of 1 to 4 carbon atoms or haloalkyl of 1 to 4 carbon atoms; and $R^{22}$, $R^{23}$, $R^{24}$, $R^{26}$, $R^{27}$, $R^{28}$, $R^{31}$, $R^{32}$, $R^{33}$ and $R^{34}$ are independently an alkyl of 1 to 4 carbon atoms or haloalkyl group of 1 to 4 carbon atoms.

3. The benzene derivative according to claim 1, wherein $R^5$ is —$CH_2C_6H_4COOH$, or a salt thereof.

4. The benzene derivative according to claim 1, wherein $R^5$ is —$CH_2C_6H_4$-4-$COOH$, or a salt thereof.

5. A pharmaceutical composition comprising a benzene derivative of the formula (I):

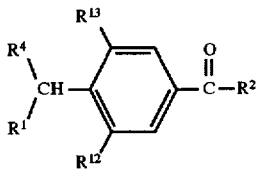

(I)

wherein $R^1$ is hydrogen, alkyl of 1 to 6 carbon atoms or haloalkyl of 1 to 6 carbon atoms; $R^2$ is hydroxyl, —$OR^{22}$, three-membered to seven-membered saturated cycloaliphatic amino group which may be interrupted by one or more nitrogen, oxygen or sulfur atoms, —$NHR^{23}$, —$N(R^{24})_2$ or —$NH_2$; $R^4$ is hydrogen or alkyl of 1 to 6 carbon atoms; $R^{12}$ is —$R^{11}$—$R^5$—; $R^{11}$ is —NH—, —$N(R^{26})$—, —$N(C(=O)R^{27})$—, —$N(C(=O)NH_2)$— or —$N(C(=O)NHR^{28})$—; $R^{13}$ is hydrogen atom, alkyl of 1 to 6 carbon atoms or haloalkyl of 1 to 6 carbon atoms; $R^5$ is —$CH_2C_6H_4COOH$, —$CH_2C_6H_4COOR^{31}$, —$CH_2C_6H_4OH$, —$CH_2C_6H_4OR^{32}$, —$CH_2C_6H_4NH_2$, —$CH_2C_6H_4N(R^{33})_2$, —$CH_2C_6H_4$-azole or —$CH_2C_6H_4NHR^{34}$; and $R^{22}$, $R^{23}$, $R^{24}$, $R^{26}$, $R^{27}$, $R^{28}$, $R^{31}$, $R^{32}$, $R^{33}$ and $R^{34}$ are independently an alkyl of 1 to 6 carbon atoms or haloalkyl group of 1 to 6 carbon atoms; or a salt thereof.

6. The composition of claim 5, wherein $R^1$ is hydrogen, alkyl of 1 to 5 carbon atoms or haloalkyl of 1 to 5 carbon atoms; $R^4$ is hydrogen or alkyl of 1 to 4 carbon atoms; $R^{13}$ is hydrogen, alkyl of 1 to 4 carbon atoms or haloalkyl of 1 to 4 carbon atoms; and $R^{22}$, $R^{23}$, $R^{24}$, $R^{26}$, $R^{27}$, $R^{28}$, $R^{31}$, $R^{32}$, $R^{33}$ and $R^{34}$ are independently an alkyl of 1 to 4 carbon atoms or haloalkyl group of 1 to 4 carbon atoms.

7. A method for treating kidney disease comprising administering to a patient in need of treatment an effective amount of a composition comprising a benzene derivative of the formula (I):

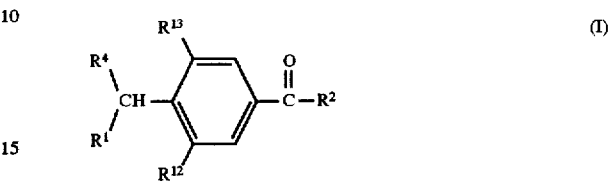

(I)

wherein $R^1$ is hydrogen, alkyl of 1 to 6 carbon atoms or haloalkyl of 1 to 6 carbon atoms; $R^2$ is hydroxyl, —$OR^{22}$, three-membered to seven-membered saturated cycloaliphatic amino group which may be interrupted by one or more nitrogen, oxygen or sulfur atoms, —$NHR^{23}$, —$N(R^{24})_2$ or —$NH_2$; $R^4$ is hydrogen or alkyl of 1 to 6 carbon atoms; $R^{12}$ is —$R^{11}$—$R^5$—; $R^{11}$ is —NH—, —$N(R^{26})$—, —$N(C(=O)R^{27})$—, —$N(C(=O)NH_2)$— or —$N(C(=O)NHR^{28})$—; $R^{13}$ is hydrogen atom, alkyl of 1 to 6 carbon atoms or haloalkyl of 1 to 6 carbon atoms; $R^5$ is —$CH_2C_6H_4COOH$, —$CH_2C_6H_4COOR^{31}$, —$CH_2C_6H_4OH$, —$CH_2C_6H_4OR^{32}$, —$CH_2C_6H_4NH_2$, —$CH_2C_6H_4N(R^{33})_2$, —$CH_2C_6H_4$-azole or —$CH_2C_6H_4NHR^{34}$; and $R^{22}$, $R^{23}$, $R^{24}$, $R^{26}$, $R^{27}$, $R^{28}$, $R^{31}$, $R^{32}$, $R^{33}$ and $R^{34}$ are independently an alkyl of 1 to 6 carbon atoms or haloalkyl group of 1 to 6 carbon atoms; or a salt thereof and a pharmaceutically acceptable carrier.

8. The method of claim 7, wherein $R^1$ is hydrogen, alkyl of 1 to 5 carbon atoms or haloalkyl of 1 to 5 carbon atoms; $R^4$ is hydrogen or alkyl of 1 to 4 carbon atoms; $R^{13}$ is hydrogen, alkyl of 1 to 4 carbon atoms or haloalkyl of 1 to 4 carbon atoms; and $R^{22}$, $R^{23}$, $R^{24}$, $R^{26}$, $R^{27}$, $R^{28}$, $R^{31}$, $R^{32}$, $R^{33}$ and $R^{34}$ are independently an alkyl of 1 to 4 carbon atoms or haloalkyl group of 1 to 4 carbon atoms.

* * * * *